United States Patent
Smith et al.

(10) Patent No.: US 8,535,219 B2
(45) Date of Patent: Sep. 17, 2013

(54) FLUID MANIFOLD FOR ENDOSCOPE SYSTEM

(75) Inventors: David Smith, Needham, MA (US); Richard Joseph Clark, Norfolk, MA (US); Michael S. Banik, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 17 days.

(21) Appl. No.: 12/751,029

(22) Filed: Mar. 31, 2010

(65) Prior Publication Data

US 2010/0256448 A1  Oct. 7, 2010

Related U.S. Application Data

(63) Continuation of application No. 10/955,950, filed on Sep. 30, 2004, now abandoned, which is a continuation-in-part of application No. 10/811,781, filed on Mar. 29, 2004, now Pat. No. 7,413,543, which is a continuation-in-part of application No. 10/406,149, filed on Apr. 1, 2003, now abandoned.

(51) Int. Cl.
*A61B 1/12* (2006.01)
*A61B 1/00* (2006.01)
*A61B 1/04* (2006.01)
*A61B 1/06* (2006.01)

(52) U.S. Cl.
USPC ............ 600/156; 600/127; 600/129; 600/179

(58) Field of Classification Search
USPC .......................................... 600/153, 155–157
See application file for complete search history.

(56) References Cited

U.S. PATENT DOCUMENTS

| | | | |
|---|---|---|---|
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 4,108,211 A | 8/1978 | Tanaka | |
| 4,286,585 A | 9/1981 | Ogawa | |
| 4,294,162 A | 10/1981 | Fowler et al. | |
| 4,311,134 A | 1/1982 | Mitsui et al. | |
| 4,315,309 A | 2/1982 | Coli | |
| 4,351,323 A | 9/1982 | Ouchi et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. |

(Continued)

FOREIGN PATENT DOCUMENTS

| | | |
|---|---|---|
| DE | 87 14 480 | 4/1988 |
| EP | 0 075 153 | 3/1983 |

(Continued)

*Primary Examiner* — Alireza Nia
(74) *Attorney, Agent, or Firm* — Bookoff McAndrews, PLLC

(57) ABSTRACT

A video endoscope system includes a reusable control cabinet and an endoscope that is connectable thereto. The endoscope may be used with a single patient and then disposed. The endoscope includes an illumination mechanism, an image sensor, and an elongate shaft having one or more lumens located therein. An articulation joint at the distal end of the endoscope allows the distal end to be oriented by the actuators in the control cabinet or actuators in a control handle of the endoscope. Fluidics, electrical, navigation, image, display and data entry controls are integrated into the system along with other accessories.

17 Claims, 68 Drawing Sheets

(56) References Cited

U.S. PATENT DOCUMENTS

| | | | |
|---|---|---|---|
| 4,488,039 A | 12/1984 | Sato et al. | |
| 4,491,865 A | 1/1985 | Danna et al. | |
| 4,493,537 A | 1/1985 | Nakahashi | |
| 4,495,134 A | 1/1985 | Ouchi et al. | |
| 4,499,895 A | 2/1985 | Takayama | |
| 4,503,842 A | 3/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,552,130 A | 11/1985 | Kinoshita | |
| 4,559,928 A | 12/1985 | Takayama | |
| 4,566,437 A | 1/1986 | Yamaguchi | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,618,884 A | 10/1986 | Nagasaki | |
| 4,621,618 A | 11/1986 | Omagari | |
| 4,622,584 A | 11/1986 | Nagasaki et al. | |
| 4,625,714 A | 12/1986 | Toyota et al. | |
| 4,631,582 A | 12/1986 | Nagasaki et al. | |
| 4,633,303 A | 12/1986 | Nagasaki et al. | |
| 4,633,304 A | 12/1986 | Nagasaki | |
| 4,643,170 A | 2/1987 | Miyazaki et al. | |
| 4,646,723 A | 3/1987 | Arakawa | |
| 4,649,904 A | 3/1987 | Krauter et al. | |
| 4,651,202 A | 3/1987 | Arakawa | |
| 4,652,093 A | 3/1987 | Stephen et al. | |
| 4,654,701 A | 3/1987 | Yabe | |
| RE32,421 E | 5/1987 | Hattori | |
| 4,662,725 A | 5/1987 | Nisioka | |
| 4,663,657 A | 5/1987 | Nagasaki et al. | |
| 4,667,655 A | 5/1987 | Ogiu et al. | |
| 4,674,844 A | 6/1987 | Nishioka et al. | |
| 4,686,963 A | 8/1987 | Cohen et al. | |
| 4,697,210 A | 9/1987 | Toyota et al. | |
| 4,700,693 A | 10/1987 | Lia et al. | |
| 4,713,051 A | 12/1987 | Steppe et al. | |
| 4,714,075 A | 12/1987 | Krauter et al. | |
| 4,716,457 A | 12/1987 | Matsuo | |
| 4,719,508 A | 1/1988 | Sasaki et al. | |
| 4,727,417 A | 2/1988 | Kanno et al. | |
| 4,727,418 A | 2/1988 | Kato et al. | |
| 4,745,470 A | 5/1988 | Yabe et al. | |
| 4,745,471 A | 5/1988 | Takamura et al. | |
| 4,746,974 A | 5/1988 | Matsuo | |
| 4,748,970 A | 6/1988 | Nakajima | |
| 4,755,029 A | 7/1988 | Okabe | |
| 4,758,238 A | 7/1988 | Sundblom et al. | |
| 4,762,119 A | 8/1988 | Allred et al. | |
| 4,765,312 A | 8/1988 | Sasa et al. | |
| 4,766,489 A | 8/1988 | Kato | |
| 4,787,369 A | 11/1988 | Allred et al. | |
| 4,790,294 A | 12/1988 | Allred et al. | |
| 4,794,913 A | 1/1989 | Shimonaka et al. | |
| 4,796,607 A | 1/1989 | Allred et al. | |
| 4,800,869 A | 1/1989 | Nakajima | |
| 4,805,596 A | 2/1989 | Hatori | |
| 4,806,011 A | 2/1989 | Bettinger | |
| 4,816,909 A | 3/1989 | Kimura et al. | |
| 4,819,065 A | 4/1989 | Eino | |
| 4,819,077 A | 4/1989 | Kikuchi et al. | |
| 4,821,116 A | 4/1989 | Nagasaki et al. | |
| 4,824,225 A | 4/1989 | Nishioka | |
| 4,831,437 A | 5/1989 | Nishioka et al. | |
| 4,834,069 A | 5/1989 | Umeda | |
| 4,836,187 A * | 6/1989 | Iwakoshi et al. | 600/157 |
| 4,844,052 A | 7/1989 | Iwakoshi et al. | |
| 4,844,071 A | 7/1989 | Chen et al. | |
| 4,845,553 A | 7/1989 | Konomura et al. | |
| 4,845,555 A | 7/1989 | Yabe et al. | |
| 4,847,694 A | 7/1989 | Nishihara | |
| 4,853,772 A | 8/1989 | Kikuchi | |
| 4,860,731 A | 8/1989 | Matsuura | |
| 4,867,546 A | 9/1989 | Nishioka et al. | |
| 4,868,647 A | 9/1989 | Uehara et al. | |
| 4,869,237 A | 9/1989 | Eino et al. | |
| 4,873,965 A | 10/1989 | Danieli | |
| 4,875,468 A | 10/1989 | Krauter et al. | |
| 4,877,314 A | 10/1989 | Kanamori | |
| 4,882,623 A | 11/1989 | Uchikubo | |
| 4,884,134 A | 11/1989 | Tsuji et al. | |
| 4,885,634 A | 12/1989 | Yabe | |
| 4,890,159 A | 12/1989 | Ogiu | |
| 4,894,715 A | 1/1990 | Uchikubo et al. | |
| 4,895,431 A | 1/1990 | Tsujiuchi et al. | |
| 4,897,789 A | 1/1990 | King et al. | |
| 4,899,731 A | 2/1990 | Takayama et al. | |
| 4,899,732 A | 2/1990 | Cohen | |
| 4,899,787 A | 2/1990 | Ouchi et al. | |
| 4,905,666 A | 3/1990 | Fukuda | |
| 4,918,521 A | 4/1990 | Yabe et al. | |
| 4,919,112 A | 4/1990 | Siegmund | |
| 4,919,114 A | 4/1990 | Miyazaki | |
| 4,920,980 A | 5/1990 | Jackowski | |
| 4,928,172 A | 5/1990 | Uehara et al. | |
| 4,930,494 A | 6/1990 | Takehana et al. | |
| 4,931,867 A | 6/1990 | Kikuchi | |
| 4,941,454 A | 7/1990 | Wood et al. | |
| 4,941,456 A | 7/1990 | Wood et al. | |
| 4,951,134 A | 8/1990 | Nakasima et al. | |
| 4,951,135 A | 8/1990 | Sasagawa et al. | |
| 4,952,040 A | 8/1990 | Igarashi | |
| 4,959,710 A | 9/1990 | Uehara et al. | |
| 4,960,127 A | 10/1990 | Noce et al. | |
| 4,961,110 A | 10/1990 | Nakamura | |
| 4,967,269 A | 10/1990 | Sasagawa et al. | |
| 4,971,034 A | 11/1990 | Doi et al. | |
| 4,973,311 A | 11/1990 | Iwakoshi et al. | |
| 4,979,497 A | 12/1990 | Matsuura et al. | |
| 4,982,725 A | 1/1991 | Hibino et al. | |
| 4,984,878 A | 1/1991 | Miyano | |
| 4,986,642 A | 1/1991 | Yokota et al. | |
| 4,987,884 A | 1/1991 | Nishioka et al. | |
| 4,989,075 A | 1/1991 | Ito | |
| 4,989,581 A | 2/1991 | Tamburrino et al. | |
| 4,996,974 A | 3/1991 | Ciarlei | |
| 4,996,975 A | 3/1991 | Nakamura | |
| 5,001,556 A | 3/1991 | Nakamura et al. | |
| 5,005,558 A | 4/1991 | Aomori | |
| 5,005,957 A | 4/1991 | Kanamori et al. | |
| 5,007,408 A | 4/1991 | Ieoka | |
| 5,018,509 A | 5/1991 | Suzuki et al. | |
| 5,022,382 A | 6/1991 | Ohshoji et al. | |
| 5,029,016 A | 7/1991 | Hiyama et al. | |
| 5,034,888 A | 7/1991 | Uehara et al. | |
| 5,036,242 A * | 7/1991 | Huber et al. | 313/35 |
| 5,040,069 A | 8/1991 | Matsumoto et al. | |
| RE33,689 E | 9/1991 | Nishioka | |
| 5,045,935 A | 9/1991 | Kikuchi | |
| 5,049,989 A | 9/1991 | Tsuji | |
| 5,050,584 A | 9/1991 | Matsuura | |
| 5,050,974 A | 9/1991 | Takasugi et al. | |
| 5,056,503 A | 10/1991 | Nagasaki et al. | |
| 5,061,994 A | 10/1991 | Takahashi | |
| 5,068,719 A | 11/1991 | Tsuji | |
| 5,074,861 A | 12/1991 | Schneider et al. | |
| 5,081,524 A | 1/1992 | Tsuruoka et al. | |
| 5,087,989 A | 2/1992 | Igarashi | |
| 5,110,645 A | 5/1992 | Matsumoto et al. | |
| 5,111,281 A | 5/1992 | Sekiguchi | |
| 5,111,306 A | 5/1992 | Kanno et al. | |
| 5,111,804 A | 5/1992 | Funakoshi | |
| 5,113,254 A | 5/1992 | Kanno et al. | |
| 5,119,238 A | 6/1992 | Igarashi | |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |
| 5,170,775 A | 12/1992 | Tagami | |
| 5,172,225 A | 12/1992 | Takahashi | |

| Patent | Date | Name |
|---|---|---|
| 5,174,293 A | 12/1992 | Hagiwara |
| 5,176,629 A | 1/1993 | Kullas et al. |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,275,152 A | 1/1994 | Krauter et al. |
| 5,291,010 A | 3/1994 | Tsuji |
| 5,299,559 A | 4/1994 | Bruce et al. |
| 5,311,858 A | 5/1994 | Adair |
| 5,324,422 A | 6/1994 | Colleran et al. |
| 5,325,845 A | 7/1994 | Adair |
| 5,331,551 A | 7/1994 | Tsuruoka et al. |
| 5,342,299 A | 8/1994 | Snoke et al. |
| 5,347,989 A | 9/1994 | Monroe et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matumoto |
| 5,436,640 A | 7/1995 | Reeves |
| 5,436,767 A | 7/1995 | Suzuki et al. |
| 5,440,341 A | 8/1995 | Suzuki et al. |
| 5,447,148 A * | 9/1995 | Oneda et al. .................. 600/131 |
| 5,448,989 A | 9/1995 | Heckele |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,483,951 A | 1/1996 | Frassica et al. |
| 5,484,407 A | 1/1996 | Osypka |
| 5,485,316 A | 1/1996 | Mori et al. |
| 5,496,260 A | 3/1996 | Krauter et al. |
| 5,515,449 A | 5/1996 | Tsuruoka et al. |
| 5,518,501 A | 5/1996 | Oneda et al. |
| 5,518,502 A | 5/1996 | Kaplan et al. |
| 5,543,831 A | 8/1996 | Tsuji et al. |
| 5,569,158 A | 10/1996 | Suzuki et al. |
| 5,569,159 A | 10/1996 | Anderson et al. |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,609,561 A | 3/1997 | Uehara et al. |
| 5,619,380 A | 4/1997 | Ogasawara et al. |
| 5,622,528 A | 4/1997 | Hamano et al. |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | van Muiden et al. |
| 5,679,216 A | 10/1997 | Takayama et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,702,754 A | 12/1997 | Zhong |
| 5,703,724 A | 12/1997 | Miyano |
| 5,704,371 A | 1/1998 | Shepard |
| 5,704,896 A | 1/1998 | Fukunishi et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,739,811 A | 4/1998 | Rosenberg et al. |
| 5,740,801 A | 4/1998 | Branson |
| 5,741,429 A | 4/1998 | Donadio et al. |
| 5,746,696 A | 5/1998 | Kondo |
| 5,749,828 A | 5/1998 | Solomon et al. |
| 5,764,809 A | 6/1998 | Nomami et al. |
| 5,767,839 A | 6/1998 | Rosenberg |
| 5,779,686 A | 7/1998 | Sato et al. |
| 5,781,172 A | 7/1998 | Engel et al. |
| 5,787,897 A | 8/1998 | Kieturakis |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,003 A * | 11/1998 | Ginsburg ...................... 607/106 |
| 5,837,023 A | 11/1998 | Koike et al. |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,963 A | 1/1999 | Pelchy et al. |
| 5,857,964 A | 1/1999 | Konstorum et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,916,147 A | 6/1999 | Boury |
| 5,923,018 A | 7/1999 | Kameda et al. |
| 5,928,136 A | 7/1999 | Barry |
| 5,929,607 A | 7/1999 | Rosenberg et al. |
| 5,929,846 A | 7/1999 | Rosenberg et al. |
| 5,929,900 A | 7/1999 | Yamanaka et al. |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |

| | | | |
|---|---|---|---|
| 5,956,416 A | 9/1999 | Tsuruoka et al. |
| 5,956,689 A | 9/1999 | Everhart, III |
| 5,956,690 A | 9/1999 | Haggerson et al. |
| 5,959,613 A | 9/1999 | Rosenberg et al. |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,482 A | 12/1999 | Madni et al. |
| 6,007,531 A | 12/1999 | Snoke et al. |
| 6,009,925 A | 1/2000 | Hall et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Rosenberg et al. |
| 6,059,719 A | 5/2000 | Yamamoto et al. |
| 6,061,004 A | 5/2000 | Rosenberg |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |
| 6,078,876 A | 6/2000 | Rosenberg et al. |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A * | 8/2000 | Takahashi ............ 600/159 |
| 6,099,465 A | 8/2000 | Inoue |
| 6,100,874 A | 8/2000 | Schena et al. |
| 6,104,382 A | 8/2000 | Martin et al. |
| 6,107,004 A | 8/2000 | Donadio, III |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamuka |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,210,337 B1 | 4/2001 | Dunham et al. |
| 6,211,904 B1 | 4/2001 | Adair et al. |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,238,799 B1 | 5/2001 | Opolski |
| 6,241,668 B1 | 6/2001 | Herzog |
| 6,260,994 B1 | 7/2001 | Matsumoto et al. |
| 6,270,453 B1 | 8/2001 | Sakai |
| 6,272,470 B1 | 8/2001 | Teshima |
| 6,275,255 B1 | 8/2001 | Adair et al. |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,364,828 B1 | 4/2002 | Yeung et al. |
| 6,365,828 B1 | 4/2002 | Kinoshita et al. |
| 6,366,799 B1 | 4/2002 | Acker et al. |
| 6,381,029 B1 | 4/2002 | Tipirneni |
| 6,398,724 B1 | 6/2002 | May et al. |
| 6,408,889 B1 | 6/2002 | Komachi |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,480,389 B1 | 11/2002 | Shie et al. |
| 6,482,149 B1 | 11/2002 | Torii |
| 6,489,987 B1 | 12/2002 | Higuchi et al. |
| 6,496,737 B2 | 12/2002 | Rudie et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,503,195 B1 | 1/2003 | Keller et al. |
| 6,511,454 B1 | 1/2003 | Nakao et al. |
| 6,520,908 B1 | 2/2003 | Ikeda et al. |
| 6,524,234 B2 | 2/2003 | Ouchi |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B1 | 4/2003 | Kortenbach et al. |
| 6,545,703 B1 | 4/2003 | Takahashi et al. |
| 6,551,239 B2 | 4/2003 | Renner et al. |
| 6,551,240 B2 | 4/2003 | Henzler |
| 6,558,317 B2 | 5/2003 | Takahashi et al. |
| 6,561,971 B2 | 5/2003 | Akiba |
| 6,565,507 B2 | 5/2003 | Kamata et al. |
| 6,569,086 B2 | 5/2003 | Ono et al. |
| 6,574,629 B1 | 6/2003 | Kaufman et al. |
| 6,589,162 B2 | 7/2003 | Nakashima et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B1 | 8/2003 | Sugimoto et al. |
| 6,605,035 B2 | 8/2003 | Ando et al. |
| 6,609,135 B2 | 8/2003 | Omori et al. |
| 6,611,846 B1 | 8/2003 | Stoodley |
| 6,614,969 B2 | 9/2003 | Eichelberger et al. |
| 6,616,601 B2 | 9/2003 | Hayakawa |
| 6,623,424 B2 | 9/2003 | Hayakawa et al. |
| 6,638,214 B2 * | 10/2003 | Akiba ............ 600/157 |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,673,012 B2 | 1/2004 | Fujii et al. |
| 6,677,984 B2 | 1/2004 | Kobayashi et al. |
| 6,678,397 B1 | 1/2004 | Ohmori et al. |
| 6,682,479 B1 | 1/2004 | Takahashi et al. |
| 6,682,493 B2 | 1/2004 | Mirigian |
| 6,685,631 B2 | 2/2004 | Minami |
| 6,686,949 B2 | 2/2004 | Kobayashi et al. |
| 6,690,409 B1 | 2/2004 | Takahashi |

| | | |
|---|---|---|
| 6,690,963 B2 | 2/2004 | Ben-Haim et al. |
| 6,692,251 B1 | 2/2004 | Logan et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hino et al. |
| 6,711,426 B2 | 3/2004 | Benaron et al. |
| 6,715,068 B1 | 3/2004 | Abe |
| 6,716,162 B2 | 4/2004 | Hakamata |
| 6,726,675 B1 | 4/2004 | Beyar |
| 6,728,599 B2 | 4/2004 | Wright et al. |
| 6,730,018 B2 | 5/2004 | Takase |
| 6,734,893 B1 | 5/2004 | Hess et al. |
| 6,736,773 B2 | 5/2004 | Wendlandt et al. |
| 6,743,239 B1 | 6/2004 | Kuehn et al. |
| 6,743,240 B2 | 6/2004 | Smith et al. |
| 6,749,559 B1 | 6/2004 | Kraas et al. |
| 6,749,560 B1 | 6/2004 | Konstorum et al. |
| 6,749,561 B2 | 6/2004 | Kazakevich |
| 6,749,601 B2 | 6/2004 | Chin |
| 6,752,758 B2 | 6/2004 | Motoki et al. |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,414 B1 | 8/2004 | McStravick et al. |
| 6,785,593 B2 | 8/2004 | Wang et al. |
| 6,793,622 B2 | 9/2004 | Konomura et al. |
| 6,796,938 B2 | 9/2004 | Sendai |
| 6,796,939 B1 | 9/2004 | Konomura et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,811,532 B2 | 11/2004 | Ogura et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang |
| 6,842,196 B1 | 1/2005 | Swift et al. |
| 6,846,285 B2 | 1/2005 | Hasegawa et al. |
| 6,846,286 B2 | 1/2005 | Hashiyama et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,856,436 B2 | 2/2005 | Brukilacchio et al. |
| 6,858,004 B1 | 2/2005 | Ozawa et al. |
| 6,858,005 B2 | 2/2005 | Ohline et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo, Jr. et al. |
| 6,868,195 B2 | 3/2005 | Fujita |
| 6,871,086 B2 | 3/2005 | Nevo et al. |
| 6,871,993 B2 | 3/2005 | Hecht |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,889,672 B2 | 5/2005 | Criddle et al. |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma et al. |
| 6,908,307 B2 | 6/2005 | Schick |
| 6,908,427 B2 | 6/2005 | Fleener et al. |
| 6,908,429 B2 | 6/2005 | Heimberger |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,821 B2 | 9/2005 | Abe et al. |
| 6,943,822 B2 | 9/2005 | Iida et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami |
| 6,949,068 B2 | 9/2005 | Taniguchi et al. |
| 6,950,248 B2 | 9/2005 | Rudischhauser et al. |
| 6,950,691 B2 | 9/2005 | Uchikubo |
| 6,954,311 B2 | 10/2005 | Amanai |
| 6,955,671 B2 | 10/2005 | Uchikubo |
| 6,956,703 B2 | 10/2005 | Saito |
| 6,960,161 B2 | 11/2005 | Amling et al. |
| 6,961,187 B2 | 11/2005 | Amanai |
| 6,962,564 B2 | 11/2005 | Hickle |
| 6,963,175 B2 | 11/2005 | Archenhold et al. |
| 6,964,662 B2 | 11/2005 | Kidooka |
| 6,967,673 B2 | 11/2005 | Ozawa et al. |
| 6,974,466 B2 | 12/2005 | Ahmed et al. |
| 6,975,968 B2 | 12/2005 | Nakamitsu et al. |
| 6,976,954 B2 | 12/2005 | Takahashi |
| 6,977,053 B2 | 12/2005 | Mukasa et al. |
| 6,977,670 B2 | 12/2005 | Takahashi et al. |
| 6,980,227 B2 | 12/2005 | Iida et al. |
| 6,980,921 B2 | 12/2005 | Anderson et al. |
| 6,981,945 B1 | 1/2006 | Sarvazyan et al. |
| 6,982,740 B2 | 1/2006 | Adair et al. |
| 6,984,206 B2 | 1/2006 | Kumei et al. |
| 6,985,183 B2 | 1/2006 | Jan et al. |
| 6,986,686 B2 | 1/2006 | Shibata et al. |
| 6,994,668 B2 | 2/2006 | Miyano |
| 6,994,704 B2 | 2/2006 | Qin et al. |
| 7,001,330 B2 | 2/2006 | Kobayashi |
| 7,008,376 B2 | 3/2006 | Ikeda et al. |
| 7,024,573 B2 | 4/2006 | Patel et al. |
| 7,090,637 B2 | 8/2006 | Danitz et al. |
| 7,169,167 B2 | 1/2007 | Chu |
| 7,591,783 B2 | 9/2009 | Boulais et al. |
| 7,637,905 B2 | 12/2009 | Saadat et al. |
| 2001/0025135 A1 | 9/2001 | Naito et al. |
| 2001/0031912 A1 | 10/2001 | Adler |
| 2001/0039370 A1 | 11/2001 | Takahashi et al. |
| 2001/0041887 A1* | 11/2001 | Crowley .................... 606/14 |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0147481 A1 | 10/2002 | Brugger et al. |
| 2002/0163575 A1 | 11/2002 | Ayame et al. |
| 2002/0165432 A1 | 11/2002 | Matsui |
| 2002/0193662 A1 | 12/2002 | Belson |
| 2002/0193664 A1 | 12/2002 | Ross et al. |
| 2003/0032860 A1 | 2/2003 | Avni et al. |
| 2003/0032863 A1 | 2/2003 | Kazakevich |
| 2003/0045778 A1 | 3/2003 | Ohline et al. |
| 2003/0065250 A1 | 4/2003 | Chiel et al. |
| 2003/0069897 A1 | 4/2003 | Roy et al. |
| 2003/0083550 A1 | 5/2003 | Miyagi |

| | | |
|---|---|---|
| 2003/0125606 A1 | 7/2003 | Amling et al. |
| 2003/0149338 A1 | 8/2003 | Francois et al. |
| 2003/0163025 A1 | 8/2003 | Kaji |
| 2003/0181905 A1 | 9/2003 | Long |
| 2004/0015079 A1 | 1/2004 | Berger et al. |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0124157 A1 | 7/2004 | Briggs et al. |
| 2004/0143159 A1 | 7/2004 | Wendlandt |
| 2004/0147809 A1 | 7/2004 | Kazakevich |
| 2004/0167379 A1 | 8/2004 | Akiba |
| 2004/0170017 A1 | 9/2004 | Zhan et al. |
| 2004/0186349 A1 | 9/2004 | Ewers et al. |
| 2004/0190305 A1 | 9/2004 | Arik et al. |
| 2004/0193016 A1 | 9/2004 | Root et al. |
| 2004/0249247 A1 | 12/2004 | Iddan |
| 2004/0257608 A1 | 12/2004 | Tipirneni |
| 2005/0030754 A1 | 2/2005 | Licht |
| 2005/0075538 A1 | 4/2005 | Banik et al. |
| 2005/0137459 A1 | 6/2005 | Chin et al. |
| 2005/0180136 A9 | 8/2005 | Popovich |
| 2005/0192476 A1 | 9/2005 | Homan et al. |
| 2005/0197861 A1 | 9/2005 | Omori et al. |
| 2005/0200698 A1 | 9/2005 | Amling et al. |
| 2005/0203341 A1 | 9/2005 | Welker et al. |
| 2005/0203418 A1 | 9/2005 | Yamada et al. |
| 2005/0205958 A1 | 9/2005 | Taniguchi et al. |
| 2005/0207645 A1 | 9/2005 | Nishimura et al. |
| 2005/0209509 A1 | 9/2005 | Belson |
| 2005/0225872 A1 | 10/2005 | Uzawa et al. |
| 2005/0226508 A1 | 10/2005 | Gotohda |
| 2005/0228221 A1 | 10/2005 | Hirakawa |
| 2005/0228222 A1 | 10/2005 | Furumi |
| 2005/0228227 A1 | 10/2005 | Weber |
| 2005/0228697 A1 | 10/2005 | Funahashi |
| 2005/0231591 A1 | 10/2005 | Abe |
| 2005/0234507 A1 | 10/2005 | Geske et al. |
| 2005/0243169 A1 | 11/2005 | Ono et al. |
| 2005/0247081 A1 | 11/2005 | Sakata et al. |
| 2005/0250983 A1 | 11/2005 | Tremaglio et al. |
| 2005/0251112 A1 | 11/2005 | Danitz et al. |
| 2005/0251998 A1 | 11/2005 | Bar-Or et al. |
| 2005/0253044 A1 | 11/2005 | Kuriyama |
| 2005/0256370 A1 | 11/2005 | Fujita |
| 2005/0256373 A1 | 11/2005 | Bar-Or et al. |
| 2005/0256377 A1 | 11/2005 | Deppmeier et al. |
| 2005/0256424 A1 | 11/2005 | Zimmon |
| 2005/0264687 A1 | 12/2005 | Murayama |
| 2005/0267417 A1 | 12/2005 | Secrest et al. |
| 2005/0271340 A1 | 12/2005 | Weisberg et al. |
| 2005/0272978 A1 | 12/2005 | Brunnen et al. |
| 2005/0273085 A1 | 12/2005 | Hinman et al. |
| 2005/0288545 A1 | 12/2005 | Matsumoto et al. |
| 2005/0288553 A1 | 12/2005 | Sugimoto |
| 2006/0015008 A1 | 1/2006 | Kennedy |

FOREIGN PATENT DOCUMENTS

| | | |
|---|---|---|
| EP | 0 437 229 | 7/1991 |
| EP | 0 689 851 | 1/1996 |
| EP | 0 728 487 | 8/1996 |
| EP | 1 300 883 | 4/2003 |
| EP | 1 433 412 | 6/2004 |
| JP | 58-78635 | 5/1983 |
| JP | 4-12725 | 1/1992 |
| JP | 4-28335 | 1/1992 |
| JP | 05-31071 | 2/1993 |
| JP | 05-091972 | 4/1993 |
| JP | 06-105800 | 4/1994 |
| JP | 3372273 | 4/1994 |
| JP | 06-254048 | 9/1994 |
| JP | 3219521 | 9/1994 |
| JP | 07-8441 | 1/1995 |
| JP | 7-12102 | 2/1995 |
| JP | 3482238 | 12/1995 |
| JP | 10-113330 | 5/1998 |
| JP | 10-286221 | 10/1998 |
| JP | 11-216113 | 8/1999 |
| JP | 2001 128933 | 5/2001 |
| JP | 2002 078675 | 3/2002 |
| JP | 2002-102152 | 4/2002 |
| JP | 2002-177197 | 6/2002 |
| JP | 2002-185873 | 6/2002 |
| JP | 2002-253481 | 9/2002 |
| JP | 2003-75113 | 3/2003 |
| JP | 2002 007134 | 7/2003 |
| JP | 2003-348454 | 12/2003 |
| WO | WO 93/13704 | 7/1993 |
| WO | WO 03/097156 | 11/2003 |
| WO | WO 2004/016310 | 2/2004 |
| WO | WO 2005/023082 | 3/2005 |

* cited by examiner

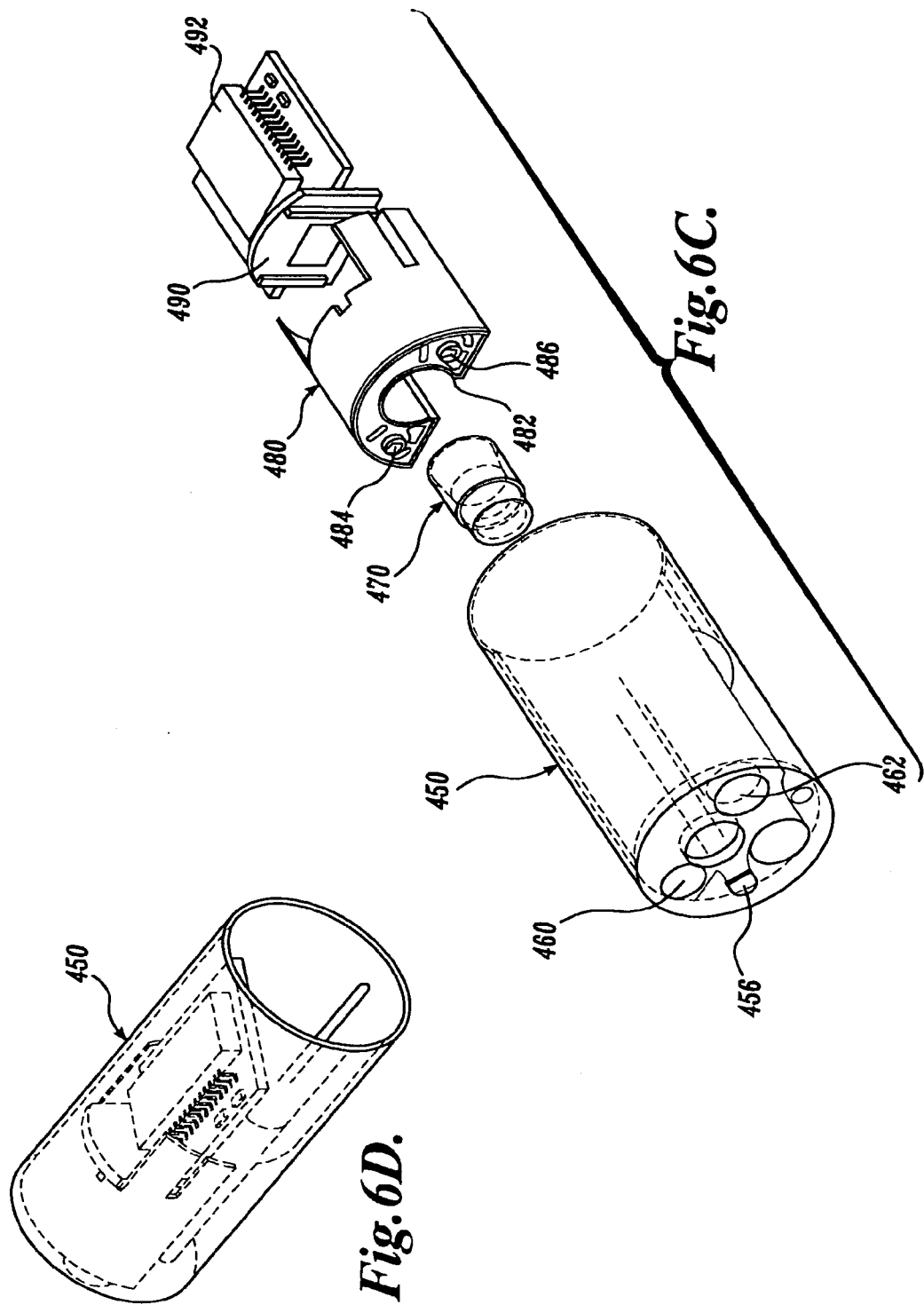

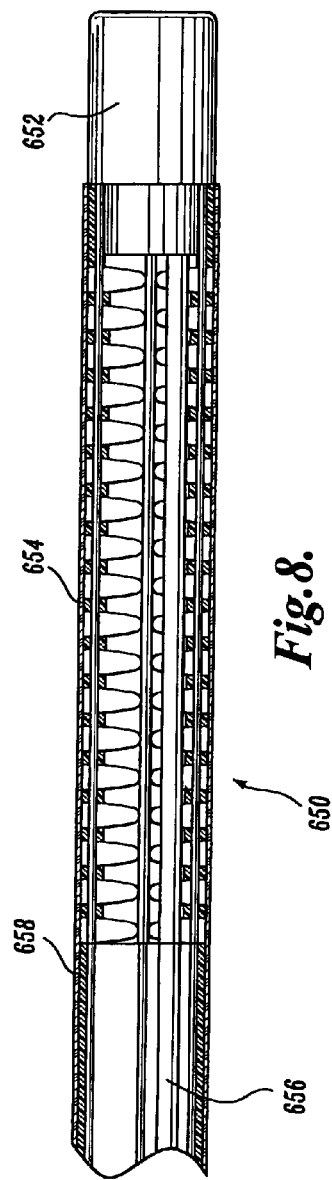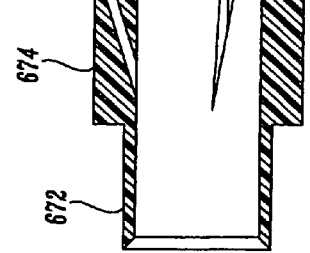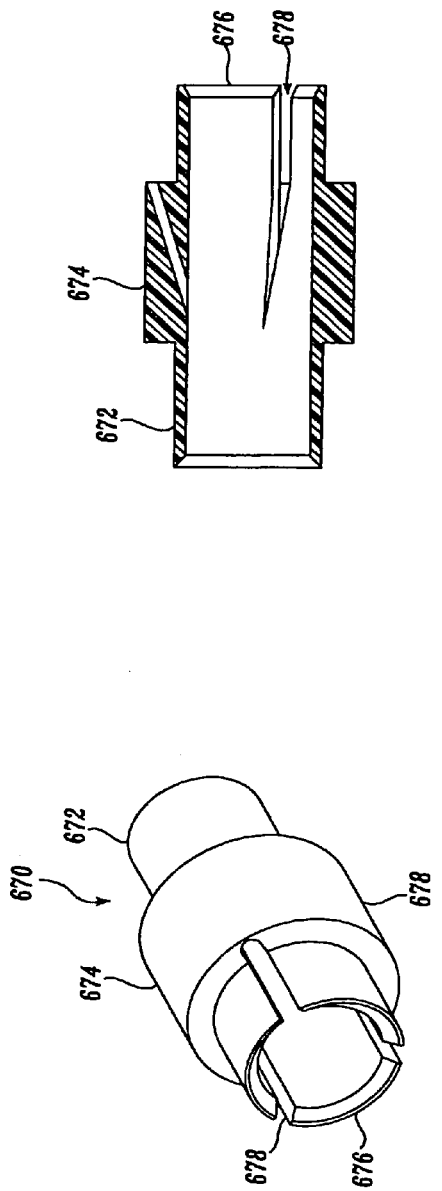

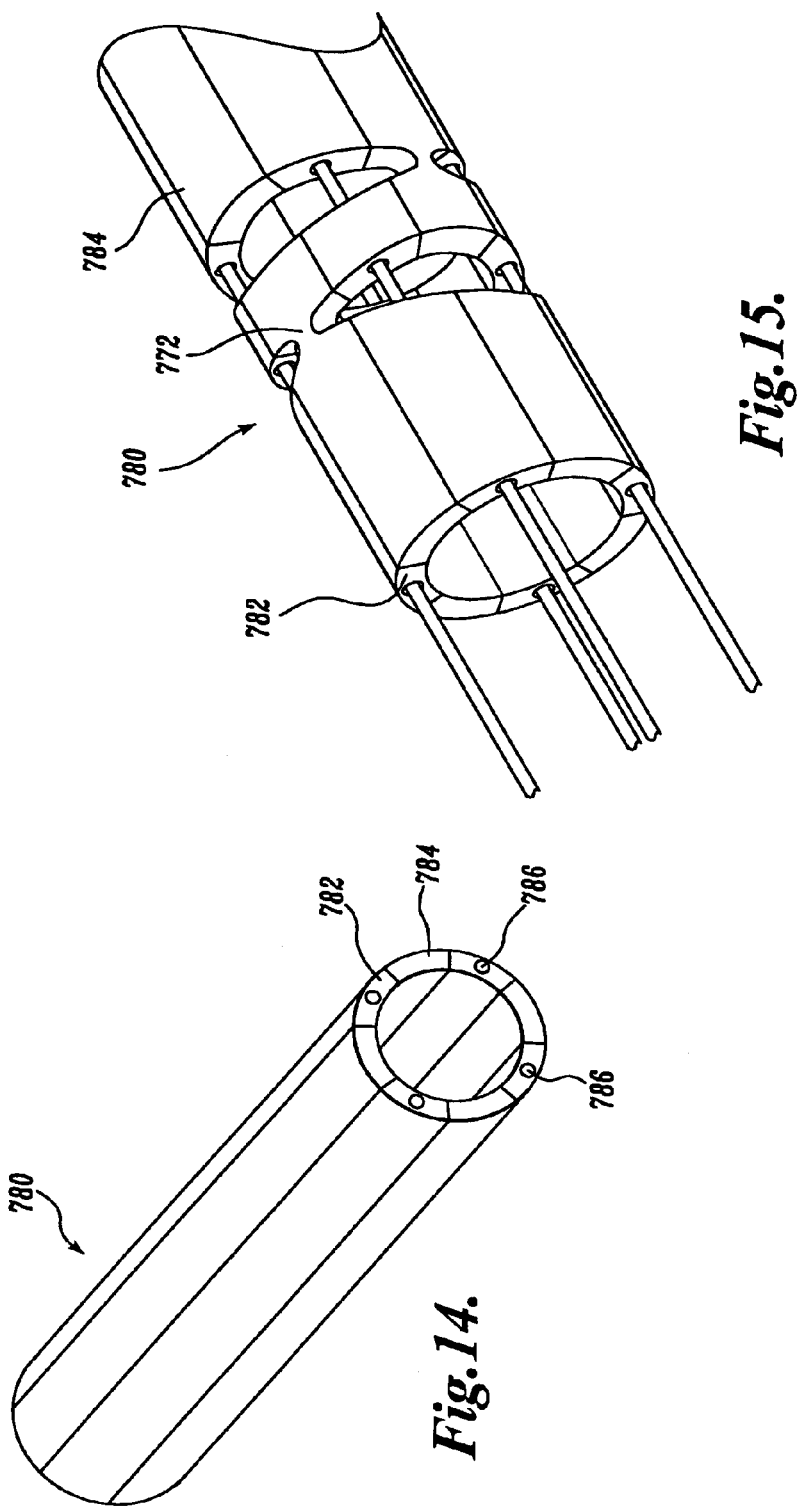

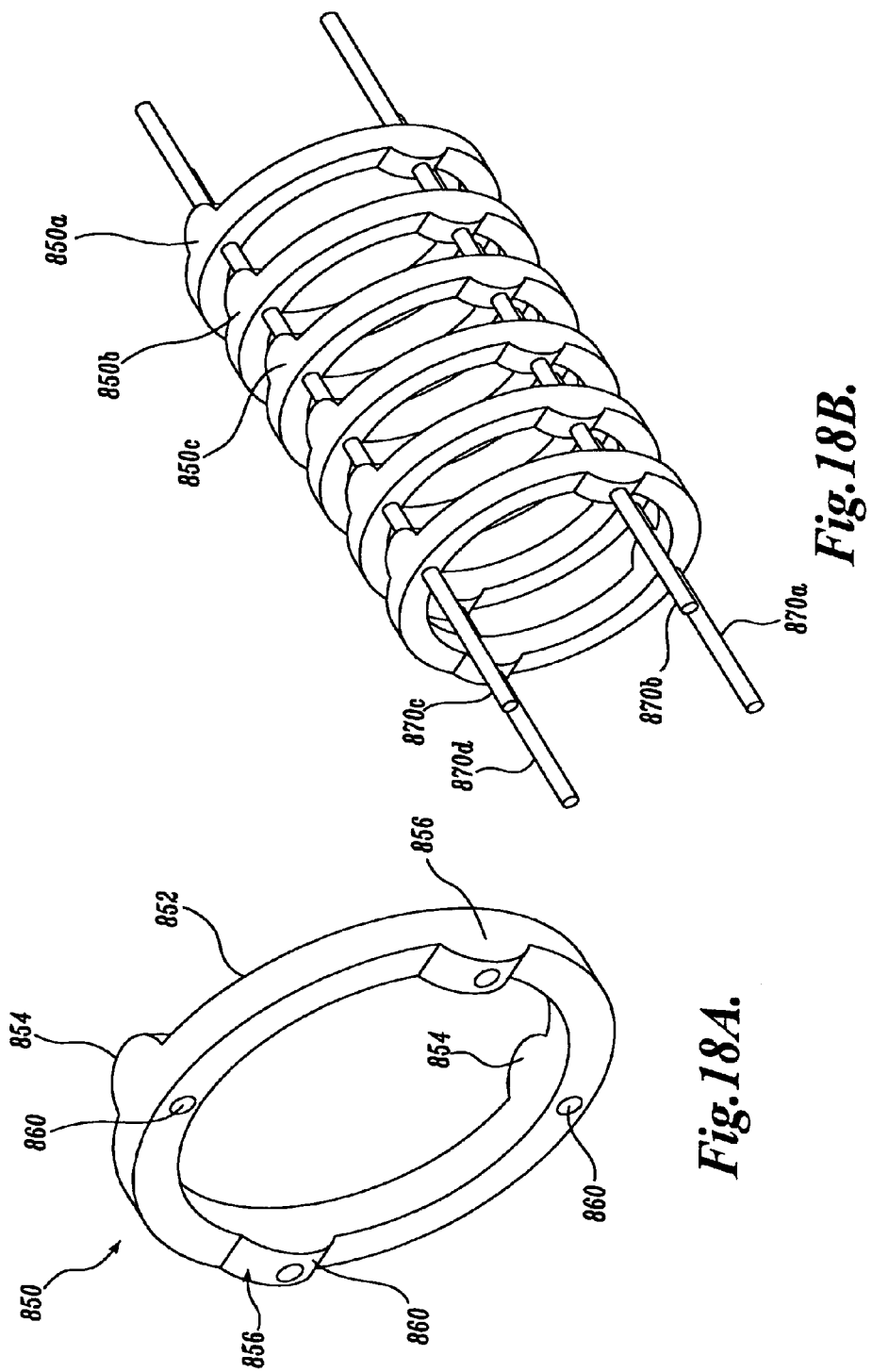

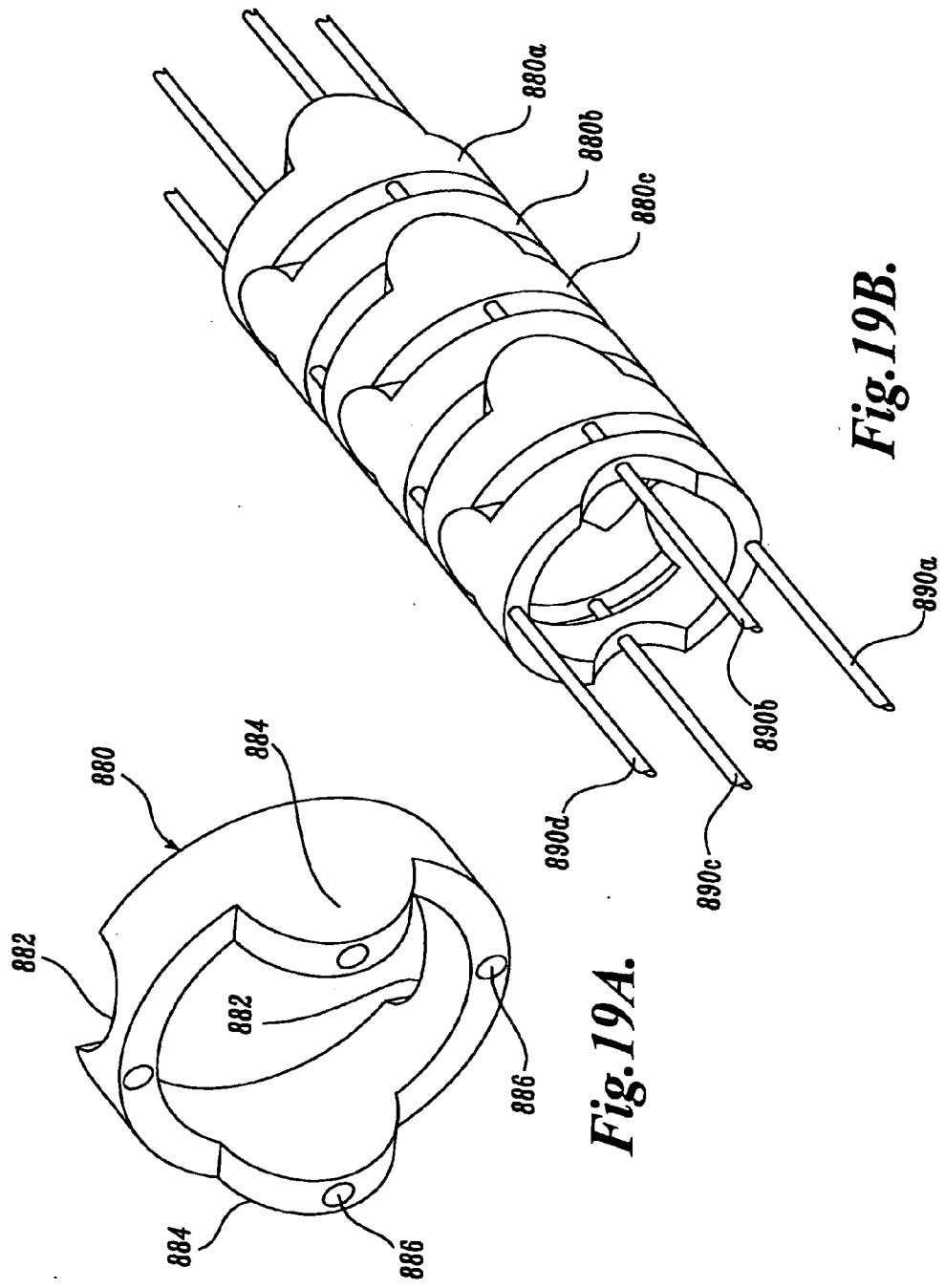

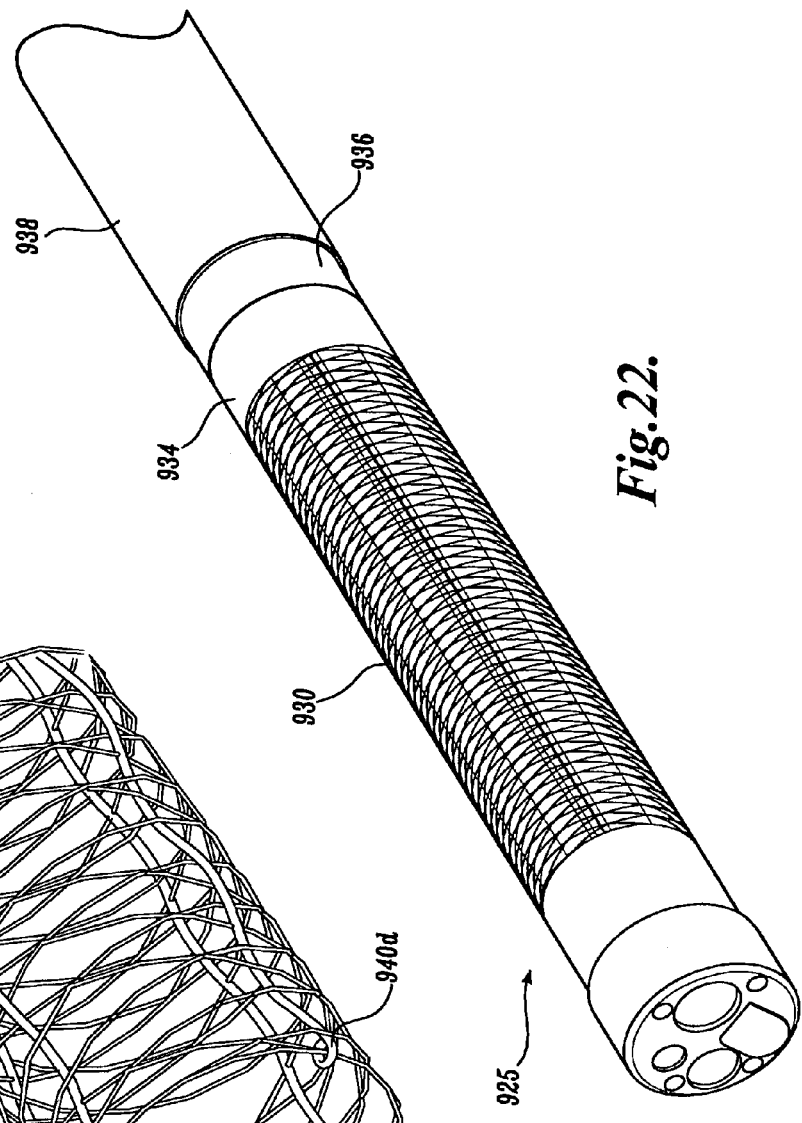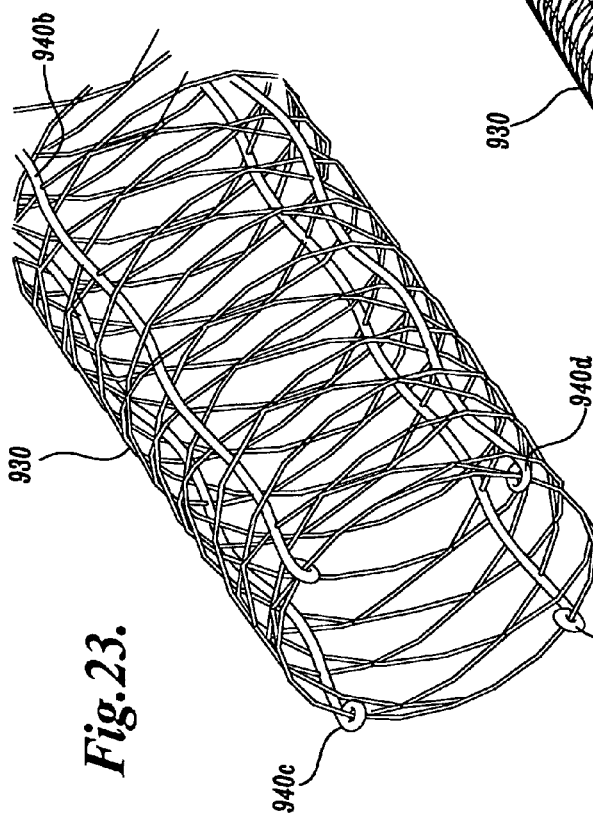
Fig.22.
Fig.23.

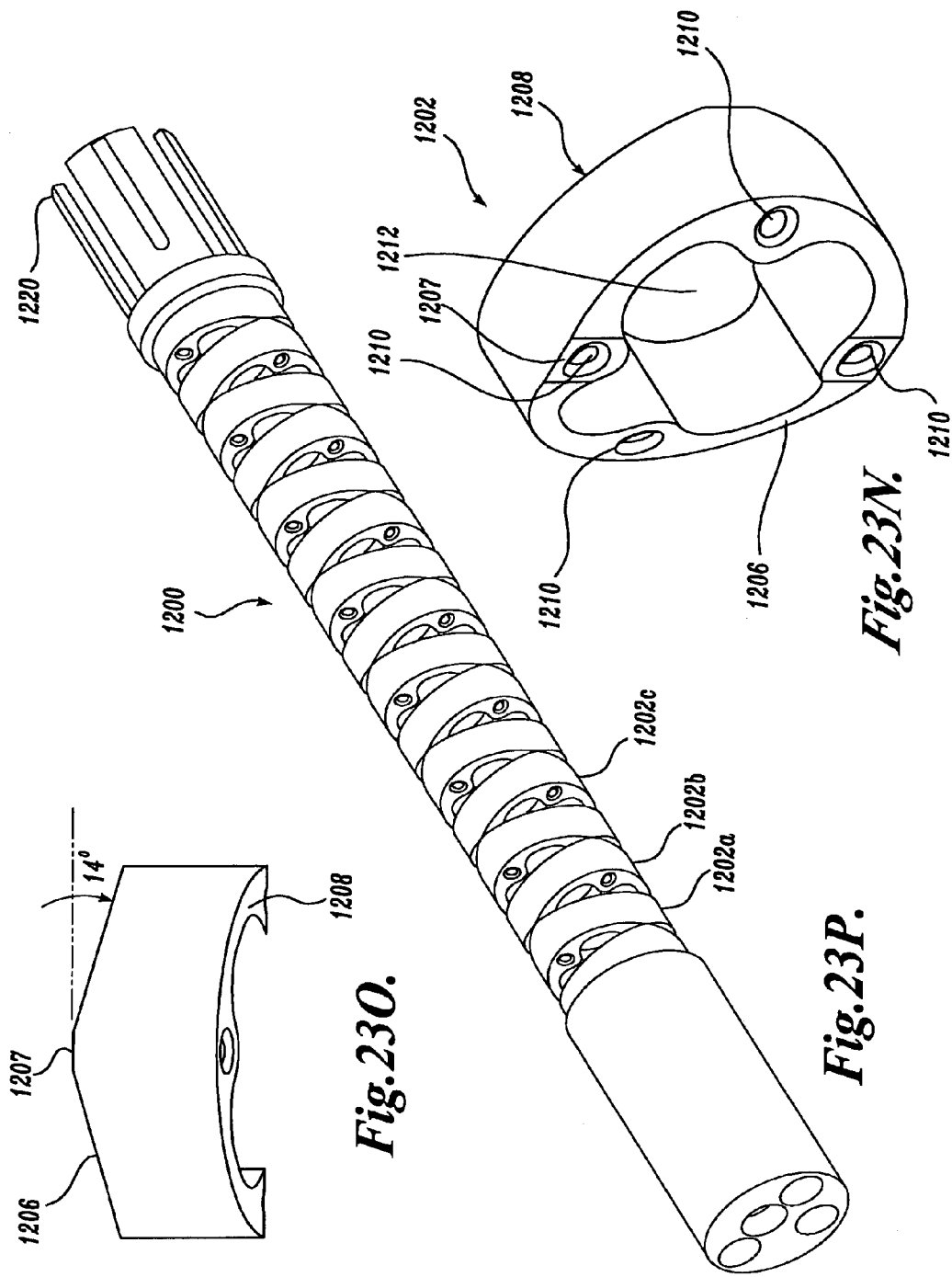

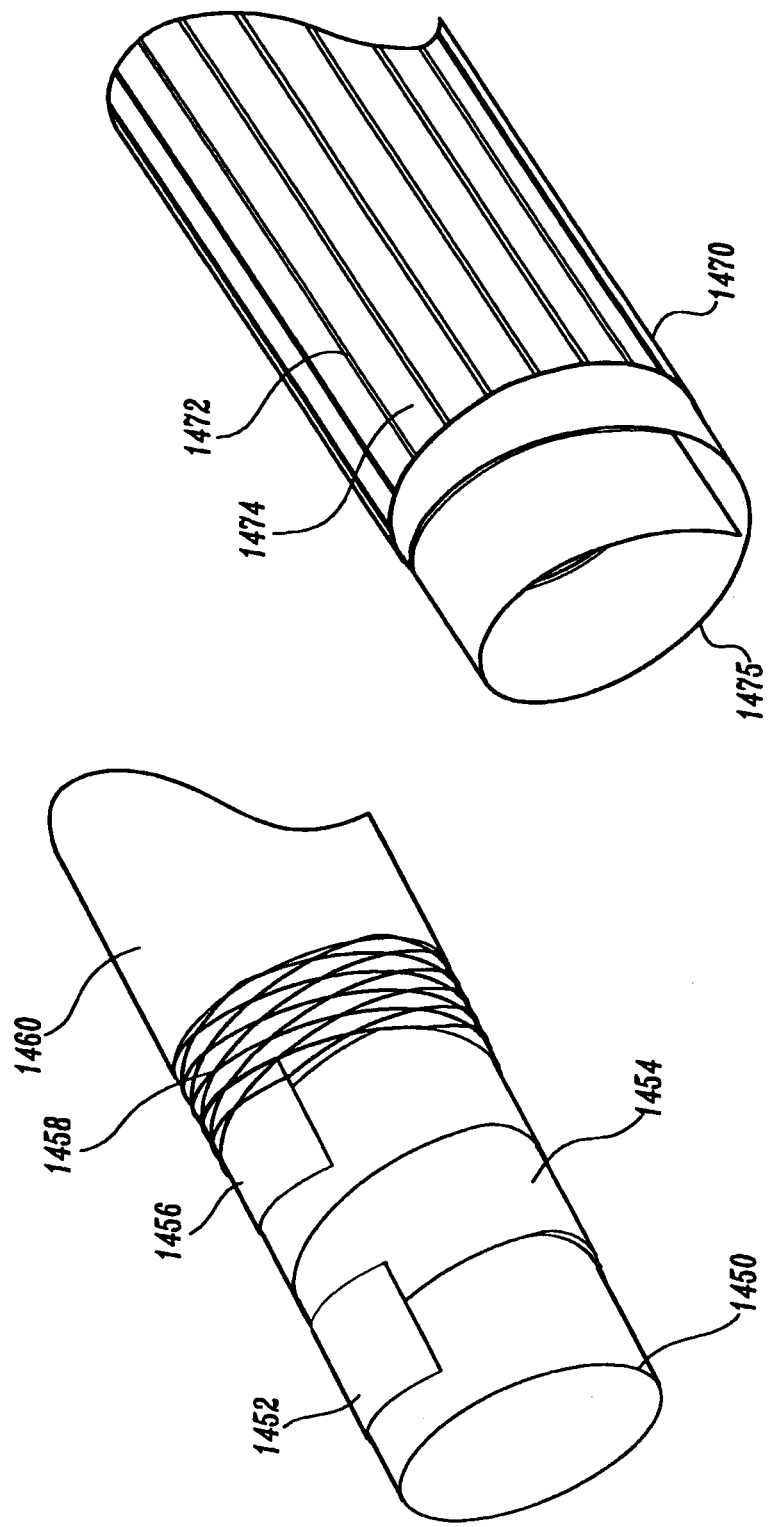

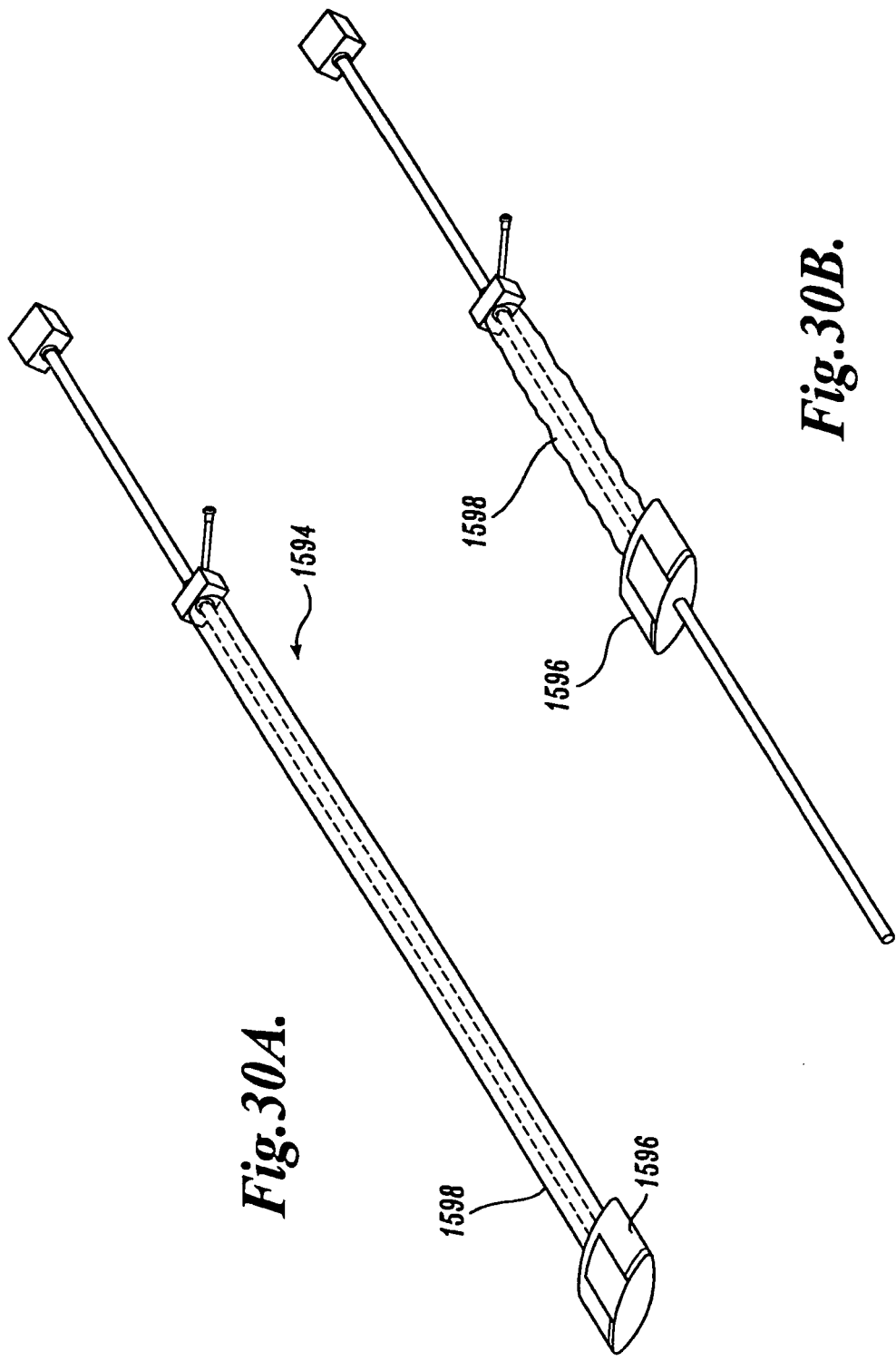

FLUID MANIFOLD FOR ENDOSCOPE SYSTEM

CROSS-REFERENCE TO RELATED APPLICATION

The present application is a continuation of U.S. patent application Ser. No. 10/955,950, filed Sep. 30, 2004, now abandoned which is a continuation-in-part of U.S. patent application Ser. No. 10/811,781, filed Mar. 29, 2004 (now U.S. Pat. No. 7,413,543), which is a continuation-in-part of U.S. patent application Ser. No. 10/406,149, filed Apr. 1, 2003 (now abandoned), the benefits of which are claimed under 35 U.S.C. §120 and are herein incorporated by reference.

FIELD OF THE INVENTION

The present invention relates to medical devices in general and therapeutic and diagnostic endoscopes in particular.

BACKGROUND OF THE INVENTION

It has become well established that there are major public health benefits from regular endoscopic examinations as an aid to the early detection and treatment of disease of internal structures such as the alimentary and excretory canals and airways, e.g., the colon, esophagus, stomach, urethra, bladder, ureter, kidney, lungs, bronchi, uterus and other organ systems. A conventional imaging endoscope used for such procedures comprises a flexible tube with a fiber optic light guide that directs illuminating light from an external light source to the distal tip where it illuminates the region (i.e., tissue, occlusive objects) to be examined. Frequently, additional optical components are incorporated to adjust the spread of the light exiting the fiber bundle and the distal tip. An objective lens and fiber optic imaging light guide communicating with a camera at the proximal end of the endoscope, or an imaging camera chip at the distal tip, produce an image that is displayed to the operator. In addition, most endoscopes include one or more working channels through which medical devices such as biopsy forceps, snares, fulguration probes, and other tools may be passed.

Navigation of the endoscope through complex and tortuous paths is critical to success of the examination with minimum pain, side effects, risk, or sedation to the patient. To this end, modem endoscopes include means for deflecting the distal tip of the endoscope to follow the pathway of the structure under examination, with minimum deflection or friction force upon the surrounding tissue, and to survey targeted examination sites. Control cables similar to bicycle brake cables are carried within the endoscope body in order to connect a flexible portion of the distal end to a set of control knobs at the proximal endoscope handle. By manipulating the control knobs, the operator is able to steer the endoscope during insertion and direct it to a region of interest, in spite of the limitations of such traditional control systems, which may be bulky, somewhat non-intuitive, and friction-limited. Common operator complaints about traditional endoscopes include their limited flexibility, limited column strength, and limited operator control of stiffness along the endoscope length.

For example, conventional, flexible endoscopes are expensive medical devices costing in the range of $25,000, and much more with the associated operator console. The endoscope is expensive because it includes expensive piece parts and requires laborious hand assembly. Because of the expense, these endoscopes are built to withstand repeated disinfections and use upon many patients. Conventional endoscopes are generally built of strong composite structures typically containing metals and plastics that do not degrade under reprocessing. These material structures decrease the flexibility of the endoscope and can compromise patient comfort. Furthermore, conventional endoscopes are complex and fragile instruments that frequently need expensive repair as a result of damage during use or during a disinfection procedure.

To overcome these and other problems, the development of a low cost endoscope would allow endoscopes to be used for a single procedure and then disposed, eliminating the need for preparation and cleaning and increasing the total volume of endoscopes required. This larger volume would enable the manufacturer to achieve economies of scale and to incorporate manufacturing methods that are not economical when used in current volumes and are only economical in large volumes (100,000 units/per year). The low cost endoscope should be packaged sterile or disinfected and be capable of being used for a single procedure without endoscope preparation and then discarded. The endoscope should include one or more of the following features: better navigation and tracking, a superior interface with the operator, improved access by reduced frictional forces upon the lumenal tissue, increased patient comfort, greater clinical productivity and patient throughput than is currently available with a conventional endoscope, a lower risk of cross-contamination and the ability to be used across more procedures.

SUMMARY OF THE INVENTION

To address these and other problems in the prior art, the present invention is a video endoscope system. In one aspect, the system includes a control cabinet, a number of manual or electronic actuators that control the orientation of an endoscope and an imaging system to produce images collected by an image sensor at the distal end of the endoscope. The endoscope is connectable with the control cabinet and used to examine and/or treat a patient. After the examination procedure, the endoscope is disconnected from the control cabinet and may be disposed saving the cost and labor of cleaning and resterilization inherent in traditional reusable endoscopes.

The endoscope of the present invention includes a flexible elongate tube or shaft and an illumination source that directs light onto an examination site. An image sensor and objective lens assembly at or adjacent the distal end of the endoscope captures reflected light to produce an image of the illuminated scene. Images produced by the sensor are transmitted to a display device to be viewed by an operator. In one embodiment, an imaging assembly at the distal end of the endoscope includes an inexpensive mass-produceable assembly of components that house one or more light emitting diodes (LEDs), an image sensor such as a CMOS solid state image sensor and low cost (e.g., plastic) lens assembly. The LEDs may be thermally coupled to a heat exchanger, and air or liquid cooled in order to remove any excess heat generated by the LEDs.

The endoscope of the present invention also includes a steering mechanism such as a number of tensile control cables, which allow the distal end of the endoscope to be deflected in a desired direction. In one embodiment of the invention, the proximal end of the tensile control cables is connected to a mechanical control mechanism (e.g., knobs) mounted in a proximal control handle. In another embodiment, the cables communicate with actuators within the control cabinet. In the latter, a directional controller generates electrical control signals which are sent via a processor within the control cabinet, which generates control signals to drive the actuators in order to orient the distal end of the endoscope in the direction desired by the operator. In another embodiment of the invention, the distal end of the endoscope is automatically steered, based on analysis of images from the image sensor. A joystick or other directional controller may include tactile, haptic or other sensory feedback to reflect the force against a tissue wall or to alert the operator that the endoscope may be looped. The distal tip housing provides a high degree of integration of parts—for example, clear windows for the LEDs are insert molded into the distal tip housing to eliminate any secondary window sealing operations and to ensure a hermetic seal. In one embodiment of the invention, the endoscope includes an articulation joint that is comprised of a number of low cost (e.g., machine formed, stamped or molded parts), easily mass produced components that allow the distal end of the endoscope to be bent in a desired direction by the control cables. In one embodiment of the invention, the articulation joint exerts a restoring force such that upon release of a tensioning force, the distal end of the endoscope will straighten.

In another embodiment of the invention, the endoscope has a variation in stiffness along its length that allows the distal end to be relatively flexible while the more proximal regions of the endoscope have increased column strength and torque fidelity so that an operator can navigate the endoscope with greater ease and accuracy and precision through tortuous, compliant anatomy with fewer false advances ("loops"). A preset variation in mechanical properties (e.g., column strength, bending modulus or strength, torsion) along the length can be provided, for example, by varying the durometer rating or types or dimensions of materials that comprise a shaft of the endoscope. Operator-controlled variable stiffness can be provided by control cables that can be tightened, loosened or torqued to adjust the stiffness of the shaft. In yet another embodiment, the spacing between the components that comprise the articulation joint is selected to provide a preset variation in stiffness along the length of the articulation joint.

In yet another embodiment of the invention, the endoscope is covered with a retractable sleeve that uncovers the distal end of the endoscope during use and extends over the distal end after the endoscope is removed from a patient.

In another embodiment of the invention, the endoscope surface includes a material such as a hydrophilic coating, to reduce the coefficient of friction of the endoscope. Other coatings may be used to, for example, improve the device performance, provide an indication of prior use or contamination or deliver therapeutic agents.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 6B-6I illustrate an embodiment of an imaging assembly for use with an endoscope of the present invention;

FIG. 8 illustrates an endoscope having control cables that are routed through lumens in the walls of an endoscope shaft in accordance with an embodiment of the present invention;

FIGS. 9A and 9B illustrate a transition guide that routes control cables from a central lumen of an endoscope shaft to control cable lumens in an articulation joint in accordance with an embodiment of the present invention;

FIGS. 14 and 15 illustrate an extrusion having areas of a different durometer that is used to form an articulation joint in accordance with another embodiment of the present invention;

FIGS. 18A-18B illustrate an articulation joint formed of a number of stacked discs in accordance with another embodiment of the present invention;

FIGS. 19A-19B illustrate a disc used to form an articulation joint in accordance with another embodiment of the present invention;

FIG. 22 illustrates an endoscope having a braided member as an articulation joint in accordance with another embodiment of the present invention;

FIG. 24 illustrates an endoscope shaft having one or more memory reducing wraps in accordance with another embodiment of the present invention;

FIG. 25 illustrates an endoscope shaft including longitudinal stripes of a high durometer material in accordance with another embodiment of the present invention;

FIGS. 30A and 30B illustrate a retractable sleeve that selectively covers an endoscope in accordance with another embodiment of the present invention;

DETAILED DESCRIPTION OF THE PREFERRED EMBODIMENT

As indicated above, the present invention is a video endoscope system that allows an operator to access, and view internal body anatomy of a patient as well as to insert surgical instruments into the patient's body. In addition, the endoscope may include integrated diagnostic and therapeutic capabilities to allow the operator to treat the patient in a single procedure. An endoscope of the present invention can be sufficiently inexpensive to manufacture such that the endoscope can be considered a single use, disposable item.

Figure 1A:
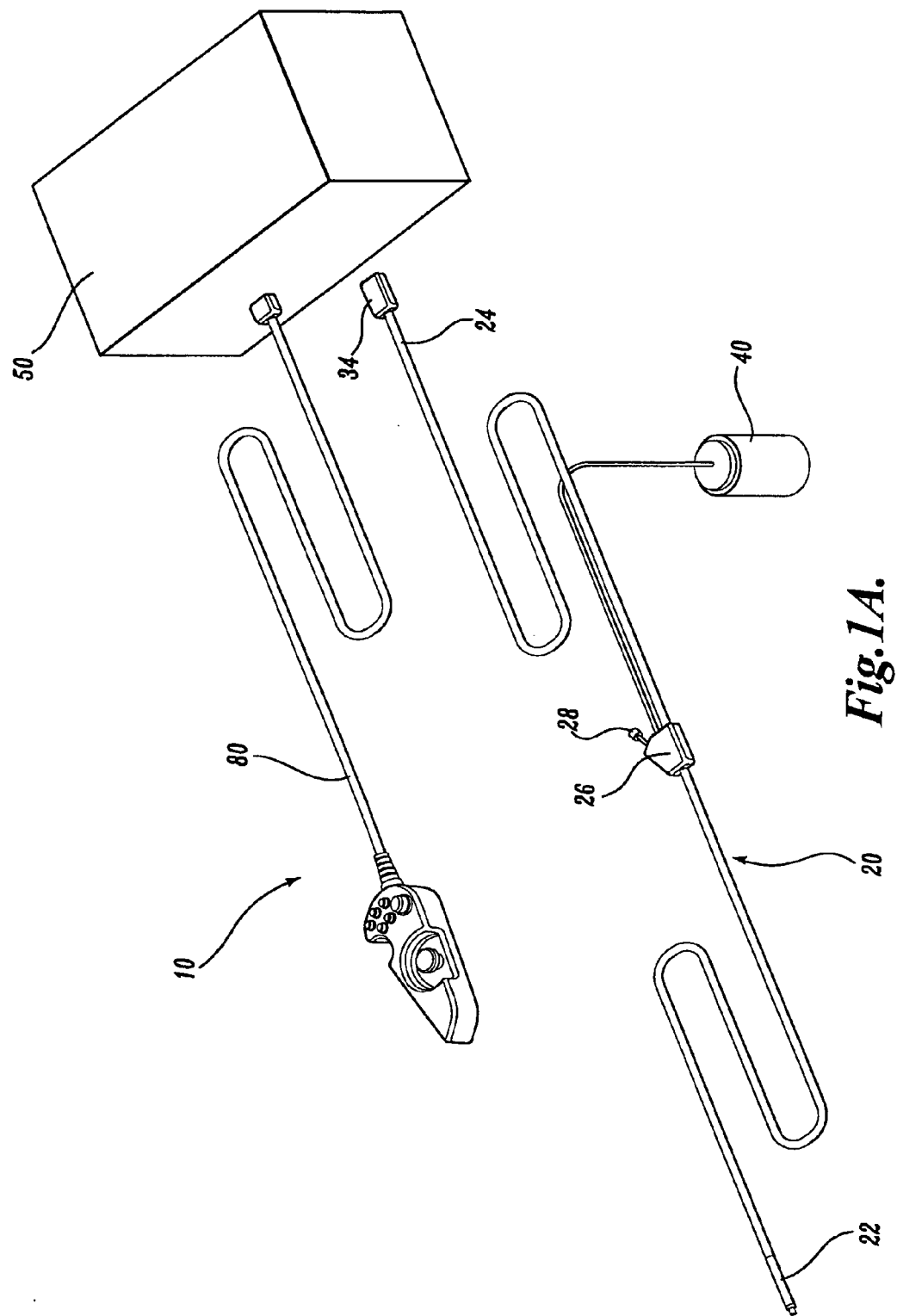
FIGS. 1A and 1B are schematic illustrations of a video endoscope system in accordance with exemplary embodiments of the present invention.

As shown in FIG. 1A, a video endoscope system 10 according to one embodiment of the present invention includes an endoscope 20, a control cabinet 50 and a handheld controller 80. The endoscope 20 has a distal tip 22 that is advanced into a patient's body cavity and a proximal end 24 that is connected to the control cabinet 50. As will be explained in further detail below, the control cabinet 50 includes a number of actuators that control a steering mechanism within the endoscope 20 in order to change the orientation of the distal tip 22. A physician or assistant uses the handheld controller 80 to input control signals that move the distal tip 22 of the endoscope 20. In addition, the control cabinet 50 may include connections to sources of air/gas and a flushing liquid such as water for clearing the endoscope 20, drugs or contrast agents. The control cabinet may also include a network connection (not shown) for allowing the control cabinet to communicate with other control cabinets, computers or the Internet. One or more external monitors, PDAs, printers, video recording systems, storage devices and storage area networks, servers, and hospital information networks or other medical devices can be connected to the control cabinet if desired. The control cabinet 50 also includes imaging electronics to process and/or transfer signals received from an image sensor, signals controlling the image sensor, and patient data to a video display (not shown) for viewing by a physician or technician.

In the embodiment shown, the endoscope 20 also includes a breakout box 26 that is positioned approximately midway along the length of the endoscope. The breakout box 26 provides an entrance to a working channel and may include an attachment point for a vacuum collection bottle 40 that collects liquids, debris or specimens received from a lumen within the endoscope. The vacuum collection bottle 40 is controlled by a vacuum valve (not shown) that is positioned on the breakout box 26. Alternatively, the valve can be positioned within or connected to the control cabinet 50 and controlled from the handheld controller 80 (see, e.g., FIG. 3D).

If desired, the handheld controller 80 can be secured to or incorporated into the breakout box 26 such that the two units can be moved as one. Upon completion of a patient examination procedure, the endoscope 20 is disconnected from the control cabinet 50 and disposed of. A new endoscope 20 is then connected to the control cabinet 50 for the next examination procedure to be performed.

Figure 1B:
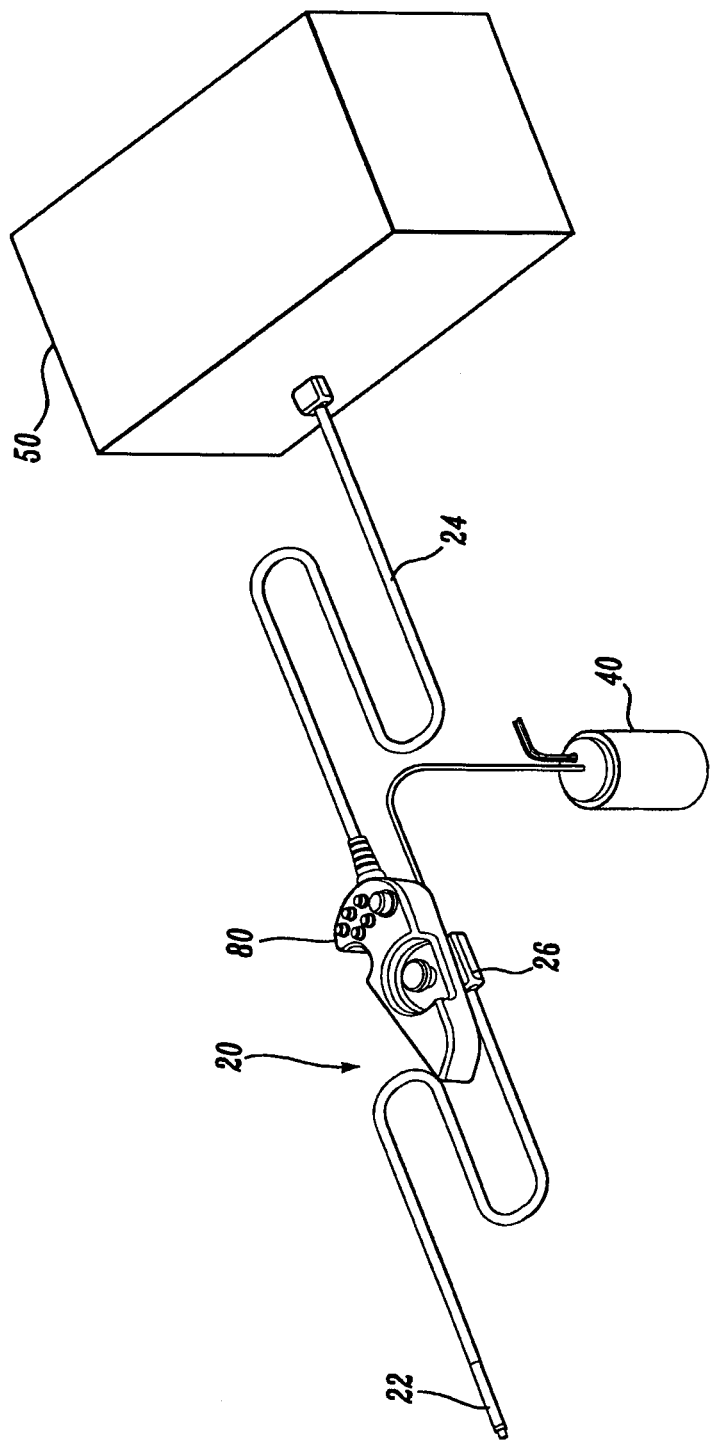

The embodiment shown in FIG. 1A is a "parallel" configuration whereby the endoscope 20 and handheld controller 80 are separately plugged into different connectors of the control cabinet 50. This parallel configuration allows one operator to handle the endoscope while another operator can manipulate the handheld controller 80. Alternatively, the handheld controller 80 may be secured to the endoscope 20 such that a single operator can control both. FIG. 1B illustrates a "serial" configuration of the invention. Here, the endoscope 20 is connected to the control cabinet 50 through the handheld controller 80. In one embodiment, the handheld controller includes one or more manually driven actuators that pull or release control cables within the endoscope that are connected to the distal tip in a manner similar to those found in conventional endoscopes. By tensioning the control cables, the operator is able to selectively orient the tip of the endoscope. In addition, the handle contains one or more switches that activate electronics in the control cabinet for the delivery of air or liquid to the endoscope as well as to control the imaging functions. In yet another embodiment, the handle may include an operator control that causes actuators in the control cabinet to drive the control cables.

Figure 1C:
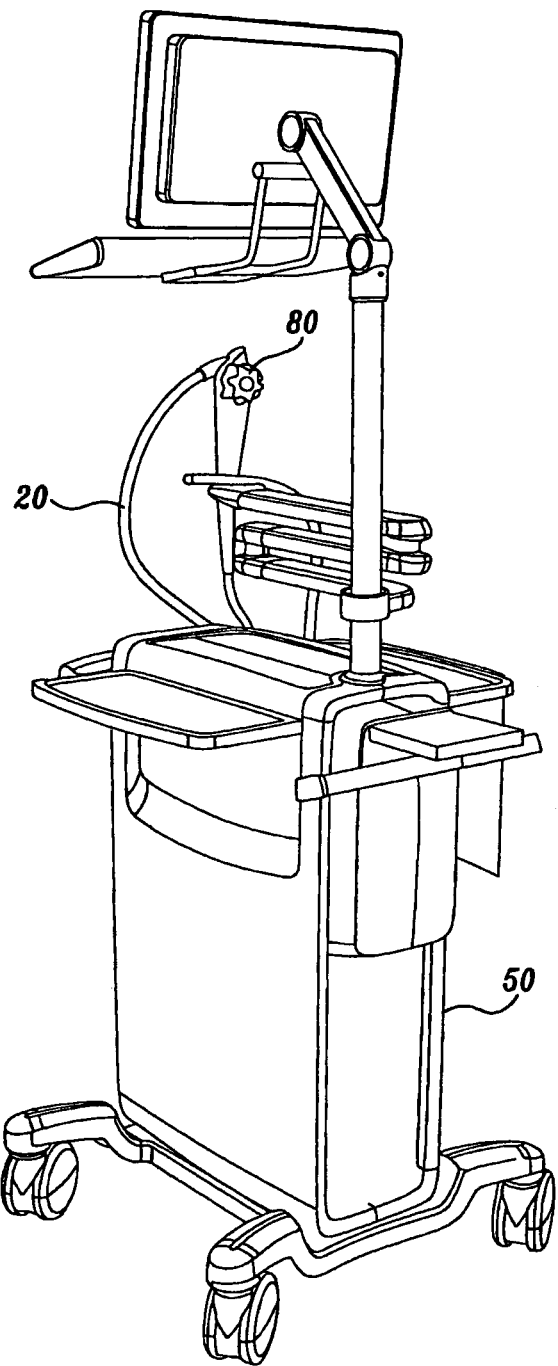
FIGS. 1C and 1D illustrate a more detailed view of an embodiment of the video endoscope of the present invention.
Figure 1D:
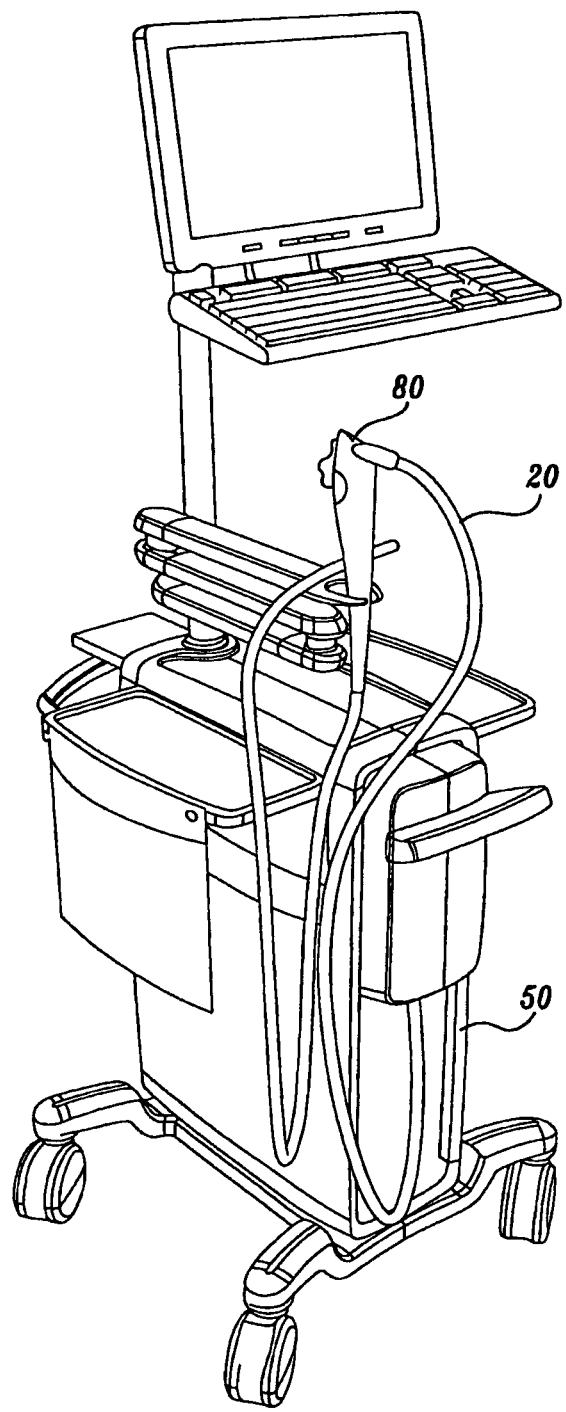

FIGS. 1C and 1D illustrate further detail of an embodiment of the video endoscope system of the present invention. The control cabinet is mounted on lockable wheels to be easily moved from place to place. In addition, the control cabinet supports a video monitor for displaying images of an examination area and other patient data. A keyboard, or touch sensor, or multi-positional switch allows the operator to enter data into a patient file and/or records of the procedure. An endoscope 20 is removably secured to the control cabinet 50. In the embodiment shown, the handheld controller is part of the endoscope and includes manual actuators to move the distal tip as well as switches to activate various functions of the system.

Figure 2:
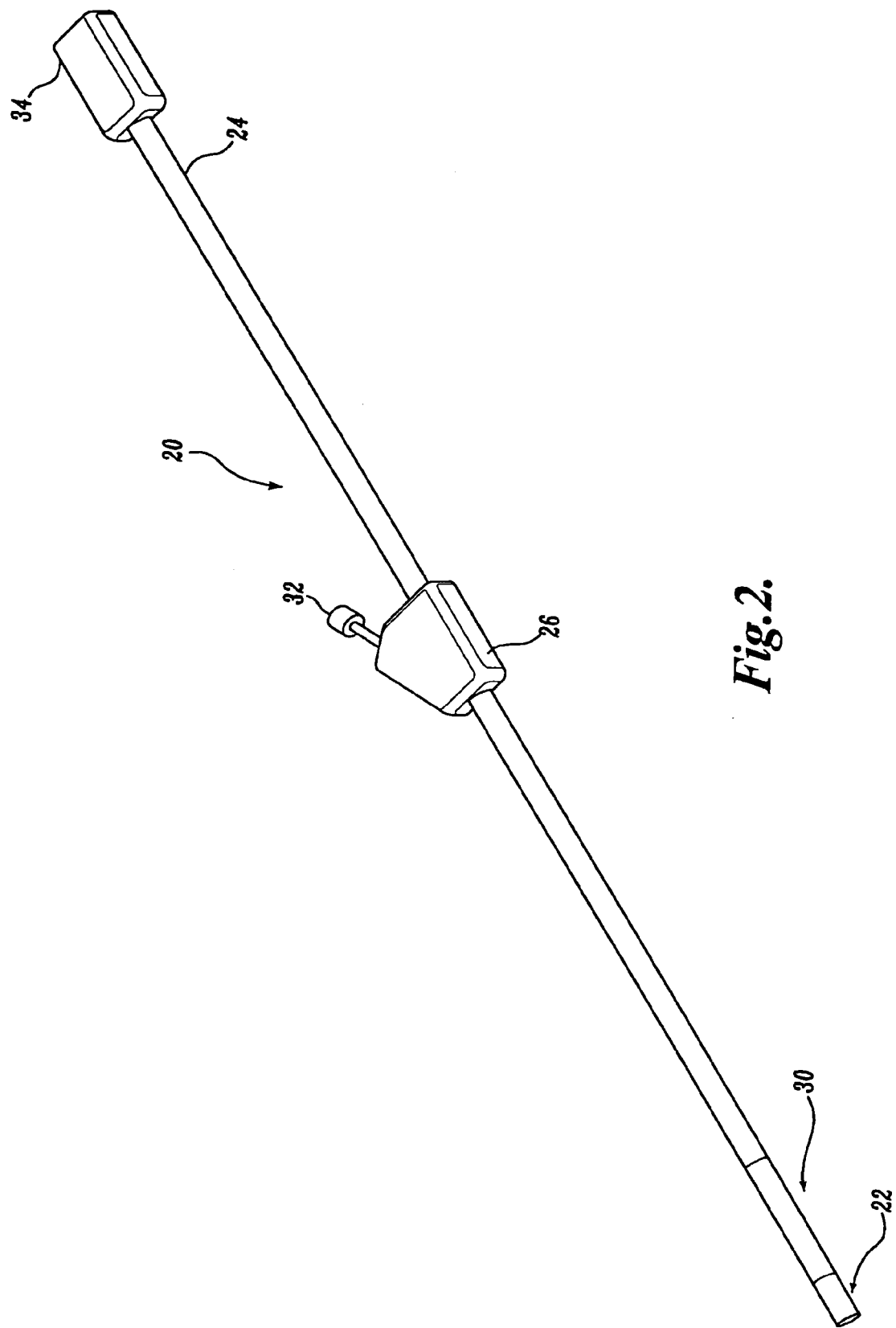
FIG. 2 illustrates further detail of an endoscope used in the video endoscope system shown in FIG. 1A.

FIG. 2 shows further detail of one embodiment of the endoscope 20. At the proximal end of the endoscope is a shaft 24, which has a lower torsional stiffness and a connector 34 that connects the endoscope 20 to the control cabinet (not shown). Distal to the breakout box 26, the shaft has a higher torsional stiffness. At the distal end of the endoscope 20 is the distal tip 22 that includes a light illumination port, an image sensor, an opening to a working channel 32 and a flushing port (not shown). Proximal to the distal tip 22 is an articulation joint 30 that provides sufficient flexibility to the distal section of the shaft such that the distal tip 22 can be directed over the required deflection range (180° or more) by the steering mechanism and can be directed to bend in any direction desired about the circumference of the distal tip. That is, the operator can select both the amount of bend or articulation and the direction of the bend.

As discussed above, the endoscope 20 in accordance with one embodiment of the invention, has a higher torque shaft at the distal section of the endoscope and a lower torque shaft at its proximal end. The breakout box 26 positioned along the length of the endoscope shaft can be used as a handle or gripper to impart rotation of the distal end of the endoscope during a medical examination procedure. The higher torque portion of the shaft transfers rotational motion that is imparted at a location near the distal tip in order to guide the distal tip of the endoscope. The lower torque shaft portion of the endoscope intentionally does not transfer torque as well for ease of manipulation and can twist when rotational motion is applied and may include one or more rotatable couplers to aid such rotation.

In use, the operator can insert a medical device such as a biopsy forceps, snare, etc., into an entrance to the working channel 32 of the endoscope found on the breakout box 26. In alternate embodiments, the medical devices may be integrally formed into the endoscope or secured, for example, on the outside thereof. In other alternative embodiments, the entrance to the working channel lumen may be positioned further towards the proximal end of the endoscope or the endoscope may include more than one working channel having entrances located at different positions along the endoscope.

Figure 3A:
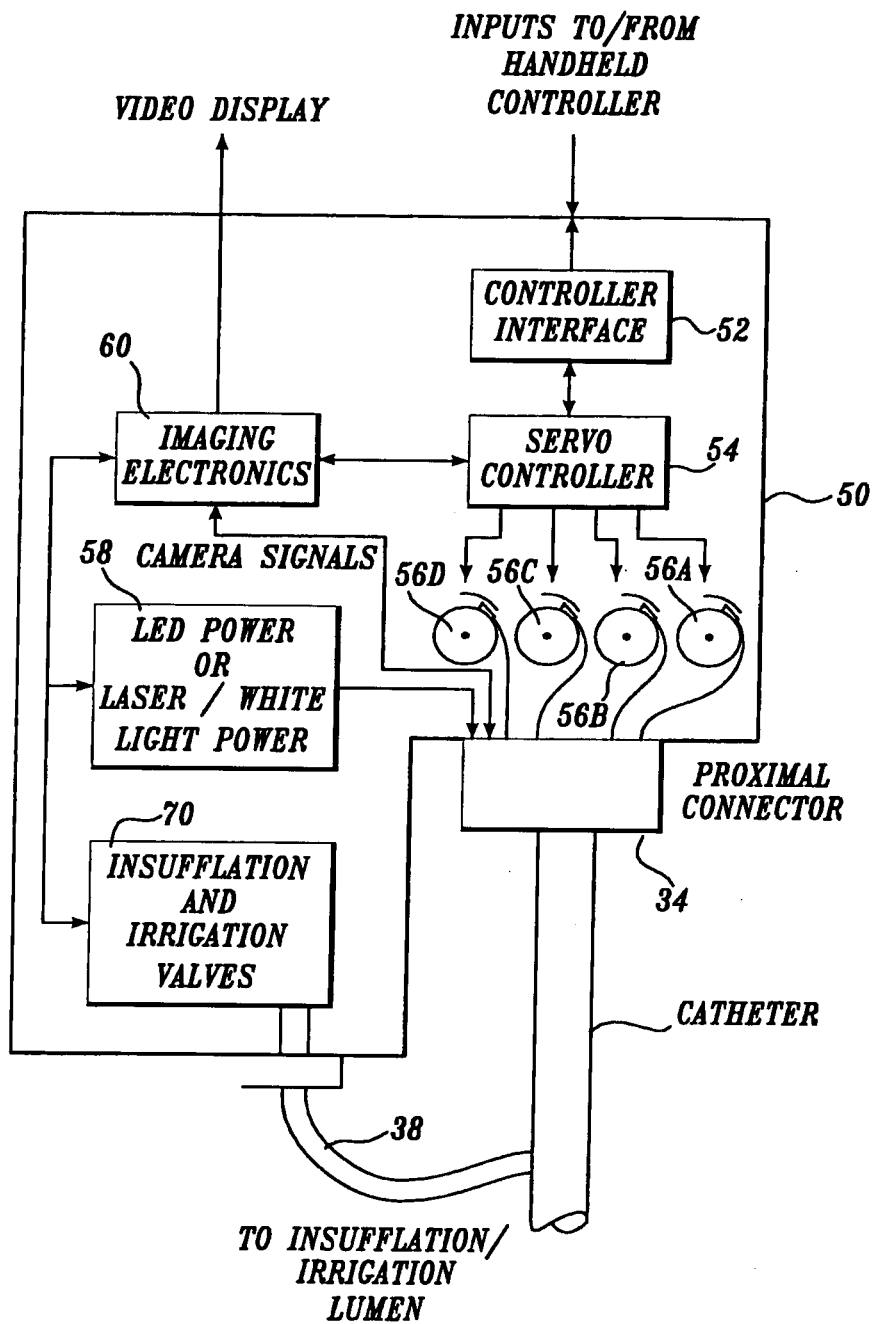
FIG. 3A is a block diagram of a control cabinet that interfaces with an endoscope in accordance with an embodiment of the present invention.

FIG. 3A is a block diagram of the major components included within one embodiment of the control cabinet 50. As indicated above and shown in FIGS. 1C and 1D, the control cabinet 50 is preferably mounted on lockable wheels so that it can easily be placed near a patient prior to an examination procedure. The control cabinet is connected to a source of electrical power, either a.c. mains or a battery, as well as to a source of insufflation gas and irrigation liquid. Inside the control cabinet 50 is a controller interface 52 that is connected to the handheld controller 80 and receives control signals therefrom. To change the orientation of the distal tip of the endoscope, the control signals are received from a directional switch in the handheld controller 80. The control signals are supplied to a servo motor controller 54 that in turn controls a number of actuators, such as servo motors 56a, 56b, 56c, 56d. Each of the servo motors 56a-56d is connected to one or more control cables within the endoscope. Motion of the servo motors 56a-56d pulls or releases the control cables in order to change the orientation of the distal tip 22 of the endoscope 20. Although the embodiment shown in FIG. 3A shows four servo motors and control cables, it will be appreciated that fewer or more servo motors and corresponding control cables could be used to move the distal tip. For example, some endoscopes may use three control cables and three associated servo motors or two motors with four control cables. Similarly, a manual handle may be equipped with a control knob or other mechanism to tension two or more control cables in order to orient the tip of the endoscope.

An imaging electronics subsystem 60 receives signals transmitted from the distal tip through the proximal connector 34 (not shown) and its associated electronics at the distal end of the endoscope. In one embodiment, the image data is brought up from the distal tip in a serial communication link, and the signal is reconstituted to produce a formatted image, in this case a 640×480 pixel image. This deserialization reconstructs the image into an array of 10 bit deep pixels—however, other bit depths could be used. The reconstructed image is an array of pixels corresponding to individual pixels at the imager. Each pixel at the imager is typically filtered by an R, G or B (red, green, blue) filter. Other filtering schemes such as subtractive color filters or the well-known Bayer pattern are also possible. Once reconstituted, the full color image is demosaiced using well known demosaicing techniques yielding a full 640×480×30 bit deep RGB color image. This image can then be converted to other video standard formats such at Y-Cb-Cr-422, NTSC, PAL, S-video, etc.

The imaging electronics subsystem 60 can enhance the images received or can provide video effects such as zoom, color changes, the incorporation of overlays, color balancing, gamma adjustment, highlighting, etc., or the addition of functionality such as a graphical user interface prior to display of the images on a video display (not shown). Images of the tissue may also be analyzed by the imaging electronics subsystem 60 and/or a separate processing circuit to produce control signals that are supplied to the servo motor controller 54 in order to automatically steer the distal tip of the endoscope as will be discussed in further detail below. Images produced by the imaging electronics subsystem 60 may also be printed on a digital printer, sent to a network server or store, saved to a computer readable media such as a floppy disc, CD, DVD, etc., or a video tape for later retrieval and analysis by a physician.

The imaging electronics subsystem 60 also provides electrical power to a light source such as a number of light emitting diodes (LEDs) at the distal end 22 of the imaging endoscope. The gain of the imager or the intensity of the LEDs can be altered to provide for proper exposure onto the imager. One manner of achieving appropriate exposure is to monitor the number of saturated pixels and adjust the light source intensity so that the number of saturated pixels is below a minimum threshold. Another approach is to adjust the light source so that the average pixel output is a set percentage, perhaps 50%. Still another is to use AGC algorithms that are common to the TV or video industry. Proper exposure can also be obtained either independently or in conjunction with adjusting the light source by changing the gains and/or the integration period of the imager itself. If desired, control signals from the imaging electronics subsystem 60 can adjust parameters of the imager to adjust its overall gain, color balance, and sensitivity.

The LED light source is easily modulatable allowing one to effect the exposure control by adjusting the current to the LEDs and hence their light output. Since the output of the LEDs can be readily controlled, one is also able to flicker the light source, by modulating the current to the LEDs, so as to increase its visibility. This effect, which is well known in the field of visual perception and to common experience, allows one to determine the location of the distal tip inside the body by observing the light that passes through the body to the outside world. This is called transillumination. By substantially modulating the output of the LEDs at a frequency of 8-14 Hz, the visibility of the tip is maintained using less power or greatly enhanced using the same power. Alternatively, the LEDs can be replaced with small incandescent bulbs or solid state devices such as a laser.

By pulsing the illumination sources, it is possible to visually detect the location of the distal tip of the endoscope without fluoroscopy or other external imaging means. If the image sensor is operating when the light source is pulsed, then the corresponding video display may flicker and distract the operator or impede the ability to see the distal tip. Therefore, during transillumination, it is desirable to prevent flicker on the video display by displaying a static image or disabling the image sensor or image processor in order to increase the visibility of the distal tip. If the endoscope utilizes an external light source, then the control cabinet can include a high intensity light source such as a laser or halogen lamp source that supplies light to a fiber optic illumination guide within the imaging endoscope 20 in order to illuminate an internal body organ or desired viewing area. Either power source 58 may be controlled by signals received from the handheld controller 80 when the user desires to activate the light source or adjust the intensity of light produced.

Finally, the control cabinet 50 includes valves 70 that control the delivery of insufflation air/gas to insufflate a patient's body cavity and an irrigation liquid to flush out a body cavity and/or clean one or more of the components of the optical assembly (such as the lens or cover window) at the distal end of the endoscope. The insufflation air/gas and irrigation liquid are connected to the endoscope via a connector 38 that connects to an irrigation/insufflation lumen of the endoscope 20. In one embodiment of the invention, the irrigation and insufflation functions are provided by the same lumen. However, it will be appreciated that separate irrigation and insufflation lumens could be provided if desired and if space in the endoscope permits. Furthermore, additional lumens or the irrigation and insufflation lumens may be used to deliver therapeutic or contrast substances to the patient.

Figure 3B:
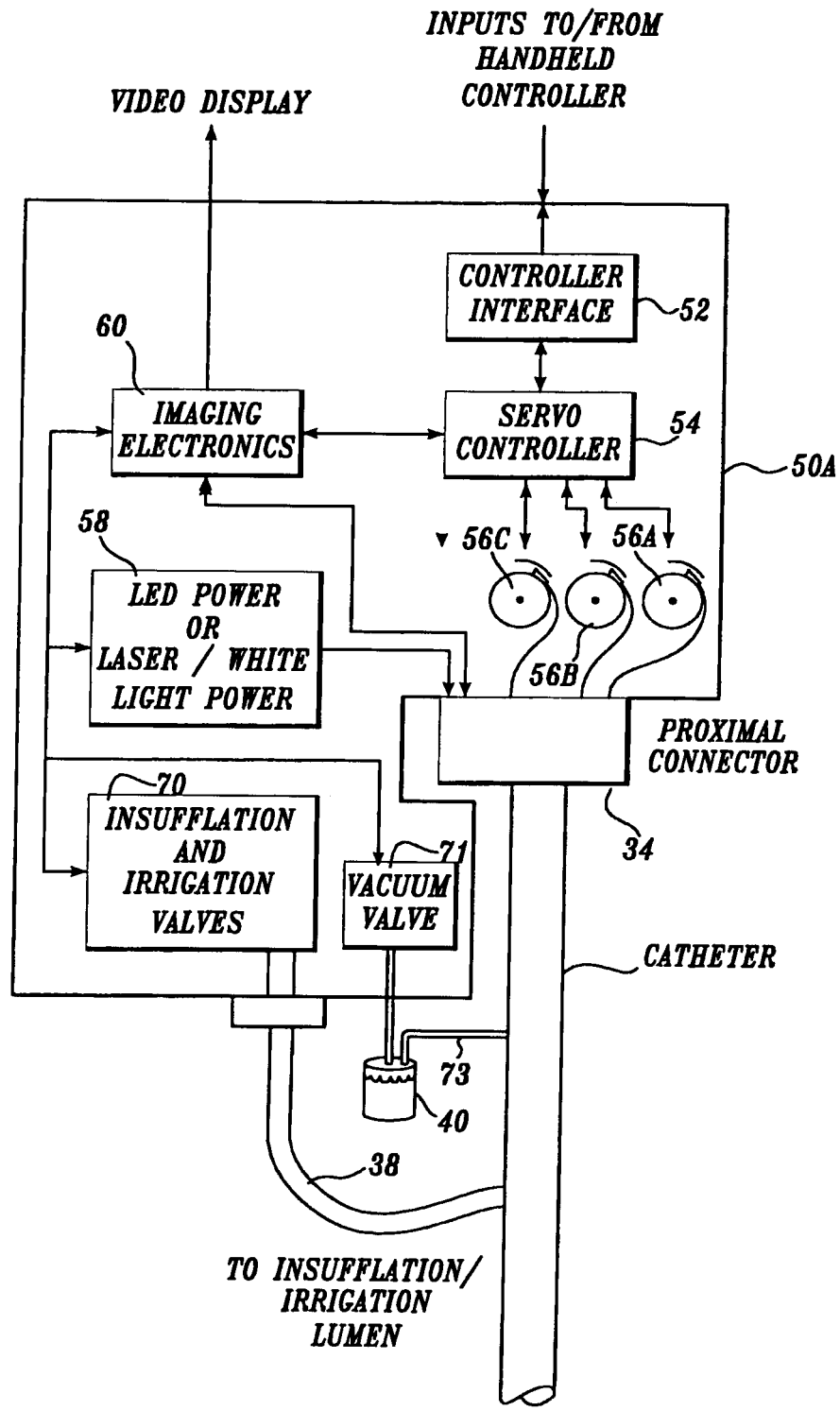
FIG. 3B is a block diagram of a control cabinet that interfaces with an endoscope in accordance with another embodiment of the present invention.

FIG. 3B illustrates another embodiment of a control cabinet 50A that is similar to the cabinet shown in FIG. 3A. The control cabinet 50A includes a vacuum valve 71 that controls vacuum delivered to a vacuum collection bottle 40. A vacuum line 73 connects to a vacuum lumen within the imaging endoscope 20. The vacuum valve 71 is controlled from the handheld controller 80. Valving and control of the valves for liquid delivery and vacuum can be together or separate and can be located inside or outside of the cabinet or along the endoscope etc.

Figure 3C:
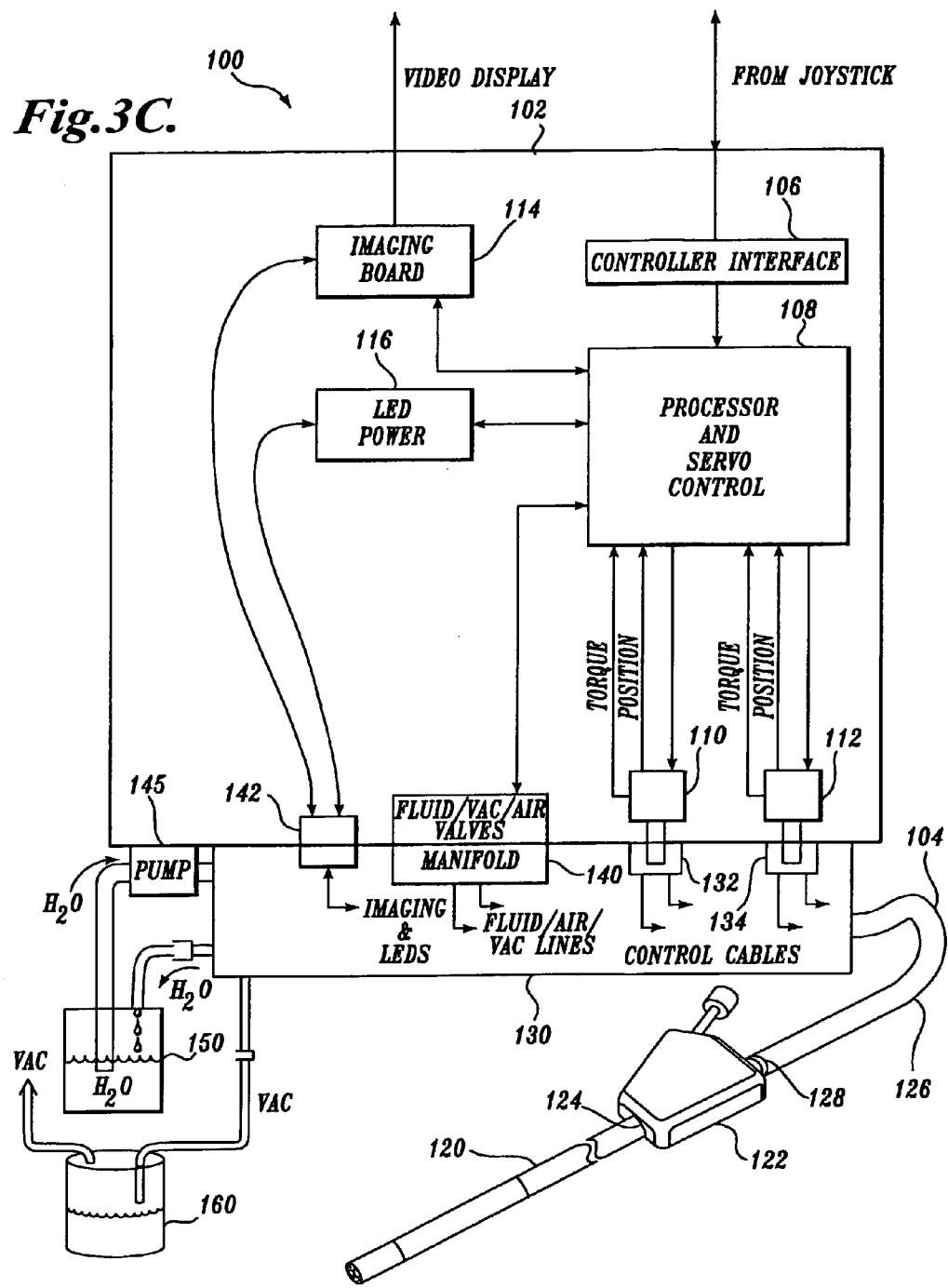
FIG. 3C is a block diagram of a control cabinet and an endoscope in accordance with another embodiment of the present invention.

FIG. 3C illustrates another embodiment of an endoscope system in accordance with the present invention. The endoscope system 100 includes a control cabinet 102 that operates to control the orientation and functions of an endoscope 104. The control cabinet 102 includes a controller interface 106 that receives commands from an input device such as a joystick, that is used by the operator to control the operation of the endoscope. Other examples of input devices include voice control, head mounted controls, touch pads, track balls, membrane switches, foot switches, etc. Commands from the joystick are supplied to a programmable processor such as a digital signal processor that controls the overall operation of the imaging system and a servo control unit 108. The processor and servo control unit control the operation of a pair of servo motors 110, 112 that in turn drive control cables within the endoscope 104. The orientation of the distal tip is controlled in response to directional signals received from the user input device as well as feedback signals obtained from sensors that measure the position and torque of each of the servo motors 110, 112. In some instances the servo motors 110, 112 may be connected to the control cables through a manually or automatically controlled clutch (not shown). The clutch allows the servo motors to be disengaged from the control cables if desired.

In one embodiment of the invention, the processor and servo control unit 108 implement a position-to-rate control that varies the speed at which the distal tip is moved as a function of the position of the directional switch on the user input device. However, other control algorithms such as position-to-position or position-to-force could also be implemented. The servo control can also be used to vary the position of or articulate instruments that are within the endoscope.

Another function that may be performed by the processor and servo control 108 is to generate a graphical indication of the approximate articulation of the tip that is shown to the user on the video display. The processor receives feedback signals regarding the position of the servo motors from which the length of control cable shortening is determined as well as the torque required to move the cables. From these values, an approximation is made of the amount of articulation at the distal tip of the endoscope. The approximate articulation amount and the direction of articulation are displayed to the physician along with the images received from the image sensor, patient data, and/or other operating parameters of the video endoscope system.

The processor and servo control unit 108 also implement a variable braking function that allows the servo motors 110, 112 to be driven under automatic or semi-automatic control by the operator moving the distal tip within the patient's body. The variable braking is accomplished by having the operator or the processor select a variable braking force that is between 0 and the maximum torque that can be supplied by the motors. When the physician moves the endoscope, the torque on the motors is detected to see if it is greater than or equal to a variable braking threshold. If so, the processor and servo control unit 108 controls one or both of the servo motors 110, 112 such that the tip is moved to a new position so that the torque readings from the motors are less than the variable braking threshold.

In some instances, such as near delicate portions of the patient's anatomy. the variable braking threshold will be set to a low value so that little pressure is required to back-drive the motors. In other instances, the braking threshold can be set high where it is desired to maintain the shape of the endoscope for navigation, etc.

In the manual control version, a variable friction brake may also be used. The user can select the brake force required be adjusting the position of a lever or dial on the manual controller similar to conventional scopes. One embodiment might involve a separate brake for each axis or alternatively, one brake may be used for both axes.

The control cabinet 102 also includes an imaging subsystem 114 that produces images from the signals that are received from the image sensor at the distal end of the endoscope 104. The imaging subsystem 114 deserializes the digital video signal from the CMOS image sensor and performs the necessary algorithms such as demosaicing, gain control and white balance to produce a quality color image. The gain control of the system is implemented by adjusting the intensity of the illumination (current supplied to the LEDs) and adjusting the gains applied to the signals by the CMOS imager. The imaging subsystem 114 also includes isolation circuitry to prevent unacceptable radio frequency susceptibility, emissions and interference, as well as unacceptable leakage currents in the event of an electrical failure in any circuit within the control cabinet 102. The imaging subsystem 114 also includes circuitry for transmitting control signals to the image sensor and for receiving image signals from the image sensor. In one embodiment of the invention, the imaging subsystem 114 is provided on a standard "PCI" circuit board to allow the use of standard computer hardware and software.

In the embodiment shown in FIG. 3C, the endoscope 104 has a distal shaft portion 120 that is connected to the breakout box 122 with a swivel connection 124. In addition, the proximal portion 126 of the shaft is connected to the breakout box 122 with a second swivel connection 128. The swivel connections 124, 128 allow the distal and proximal ends of the endoscope to rotate with respect to the breakout box 122 and without twisting the breakout box 122 in the hands of the operator.

In the embodiment shown, the endoscope 104 is connected to the control cabinet 102 with a connector 130. Within the connector 130 are a pair of spools 132, 134 that are engageable with the driveshafts of the servo motors 110, 112. Each spool 132, 134 drives a pair of control cables in opposite directions. One pair of control cables drives the distal tip of the endoscope in the up and down direction, while the other pair of control cables drives the distal tip of the endoscope in the left and right direction. Alternatively, a single control cable can be wrapped around a spool such that a single wire controls movement in a plane.

The connector 130 also includes a manifold 140 that controls the supply of fluid, air and vacuum to various tubes or lumens within the endoscope 104. In addition, the connector 130 includes an electrical connector 142 that mates with the corresponding electrical connector on the control cabinet 102. The connector 142 transfers signals to and from the image sensor and a thermal sensor as well as power to the illumination LEDs. Water is supplied to the endoscope with a pump 145. The pump 145 is preferably a peristaltic or isolated chamber pump that moves water though a flexible tube that extends into the proximal connector 130. Peristaltic pumps are preferred because the pump driving components do not need to come into contact with the water or other fluids within the endoscope, thus allowing the wetted component to be single use. A water reservoir 150 connected to the pump 145 or fixedly secured to the proximal connector supplies water to cool the illumination LEDs as well as to irrigate the region of examination. The water supplied to cool the LEDs is returned to the reservoir 150 in a closed loop. Waste water or other debris are removed from the patient with a vacuum line that empties into a collection bottle 160. Control of the vacuum to the collection bottle 160 is provided by a pinch valve within the proximal connector 130.

Figure 3D:
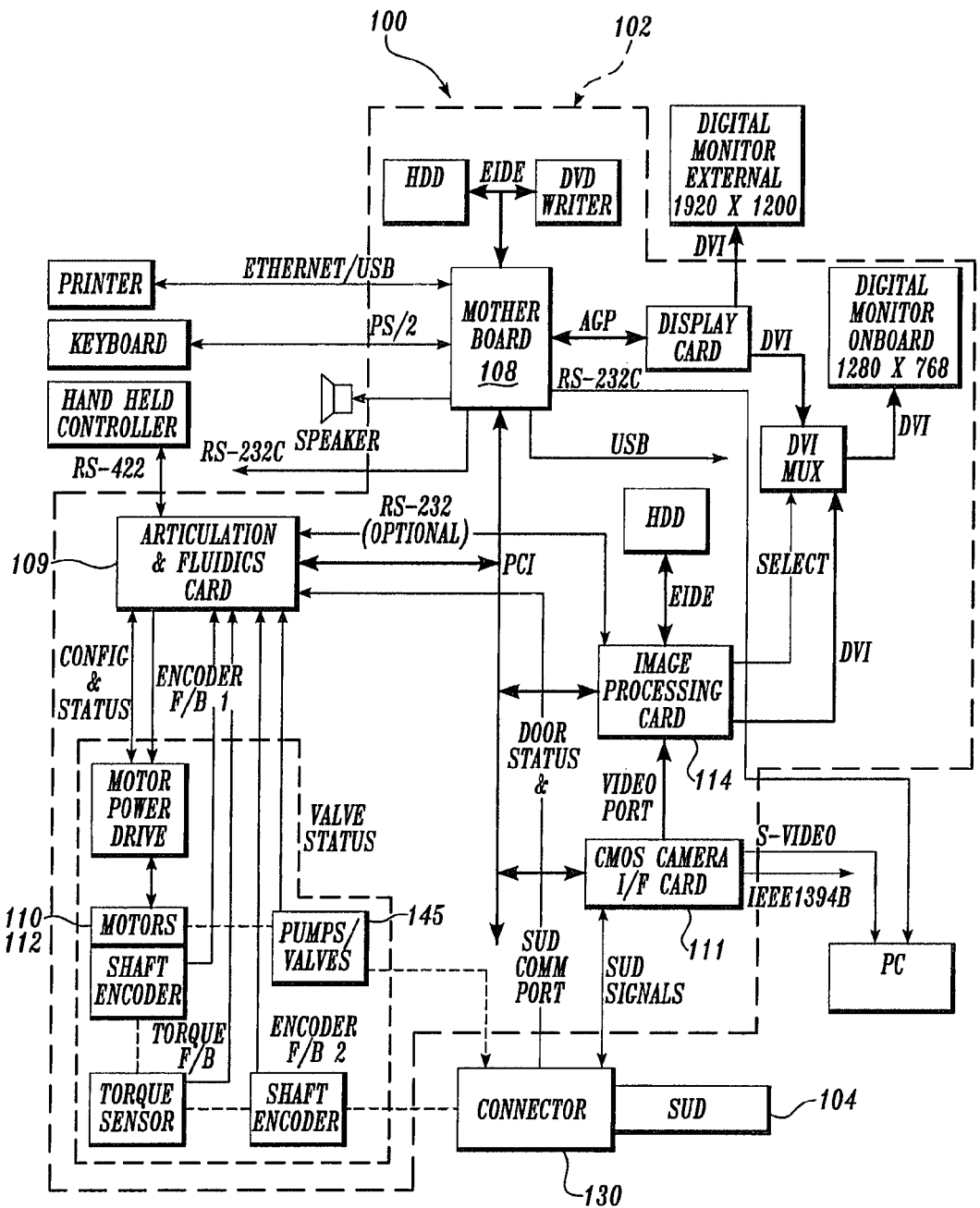
FIG. 3D is a more detailed block diagram of the components within a control cabinet and their interface to an endoscope in accordance with another embodiment of the present invention.

FIG. 3D shows further detail of a control cabinet for use with an embodiment of a video endoscope system of the present invention. Within the control cabinet 102 is a motherboard 108 that is connected by a PCI data bus to an articulation and fluids card 109, a camera card III and an imaging processing card 114. The image processing card 114 has its own hard drive connected by a EIDE connection. In addition, the mother board 108 has its own hard drive and data storage unit such as a DVD writer that are connected by an EIDE connection or similar interface. The articulation and fluidics card 109 provides signals to a power motor drive that in turn drives the servomotors 110, 112, and receives signals from the shaft encoders and torque sensors to provided feedback regarding the amount of force required to move the distal tip of the endoscope. The pumps and valves 145 are also controlled by the articulation and fluidics card 109 to supply insufflation air/gas and irrigation fluids, as well as vacuum, to the endoscope 104 via the proximal connector 130.

Images of the examination area produced by the image sensor within the endoscope 104 are displayed on a digital monitor. The digital monitor is driven through a multiplexer so that additional data such as patient name, address, date, other physiological parameters, heart rate, blood pressure, etc., or previously obtained images can be multiplexed onto the display for view by the operator. In addition, an external digital monitor may be coupled to the system, if desired.

The motherboard 108 also interfaces with a printer via an ethernet/USB or parallel connection, and a keyboard by a conventional PS/2 or USB connection. The handheld controller is connected to the articulation and fluidics card 109 via an RS-422 connection. A speaker is also coupled to the motherboard 108 to provide audible alarms or status signals to the operator.

The control cabinet 102 preferably made using a standard off-the-shelf computing platform that includes a motherboard, hard drive, video card, processor, memory, etc. Each of the control cards (camera card III, articulation and fluidics card 198, and the image processing card 114) for the system is plugged into the motherboard in a PCI slot. The motherboard also provides the standard PC type connectors: serial ports, parallel port, Ethernet port, USB ports, microphone in, sound out, etc. The two digital monitors such as LCD display panels on the control cabinet are connected to a video card that resides in the motherboard in an AGP slot. Essentially, the control cabinet includes a generic computing platform. This allows exam information to be captured electronically in a single integrated system. The types of exam information that may be captured in this integrated system includes: still images, video clips, voice recordings for annotation purposes, voice input for voice recognition, voice input for voice command and GUI navigation, text labels applied to images, drawing annotations on images, exam report information, patient discharge information, letter to the referring physician, medications given to the patient, patient vital signs, etc. The exam report can typically include entry for data elements such as the patient demographics, indication for examination, procedure(s) performed, scope(s) used in exam, instruments used in exam, procedure technique, extent of exam, complications, visualization, tolerance, findings, diagnosis, recommendations, procedure codes, diagnosis codes, interventions performed, pathology specimens collected, etc.

Patient vital signs are preferably recorded via an electronic interface. Vital sign monitors currently allow this type of digital information exchange over serial ports and Ethernet connections. As indicated, information that is typically collected is systolic blood pressure, diastolic blood pressure, mean arterial pressure, pulse from the blood pressure measurements, heart rate from an EKG, oxygen saturation, and temperature. In addition, the control cabinet can include means for electronic transfer and display of the "waveform" data that would allow the display of waveform signals such as the EKG, respiration, and oxygen saturation. This data is typically provided as a calibrated analog voltage output. An analog to digital converter (not shown) is used to digitize the waveform data for display on the screens.

The system allows the operator to navigate the system in a number of ways, such as keyboard, touch screen, and a multi-position GUI navigation control switch on the endoscope handle. Any of these navigation means may be used before or during an exam to allow the operator (nurse, physician, or technician) to enter exam-related information into the control cabinet during the exam. If all of the desired information is not entered during the course of the exam, the system allows the operator to complete the exam record at the end of the exam.

The control cabinet may also contain a barcode scanner or radio frequency identification (RFID) scanner. This would allow the identification of tools that are inserted into the working channel of the endoscope or otherwise used as part of the procedure. This allows tracking of the equipment or tools that were actually used during the exam. It also allows for intelligent prompting for the user through the GUI to record relevant information about the use of the items that were scanned. For example, the nurse scans a biopsy forceps before it is inserted into the working channel of the endoscope. The control cabinet GUI then automatically prompts the user with the typical interventions performed with the type of forceps that were inserted. The system would also prompt the user to enter information about the biopsy specimen(s) (location, description, pathology to be evaluated) such that information is entered in an automated fashion for a pathology requisition. The system could also prompt the user with default operating parameters for the instruments.

Figure 3E:
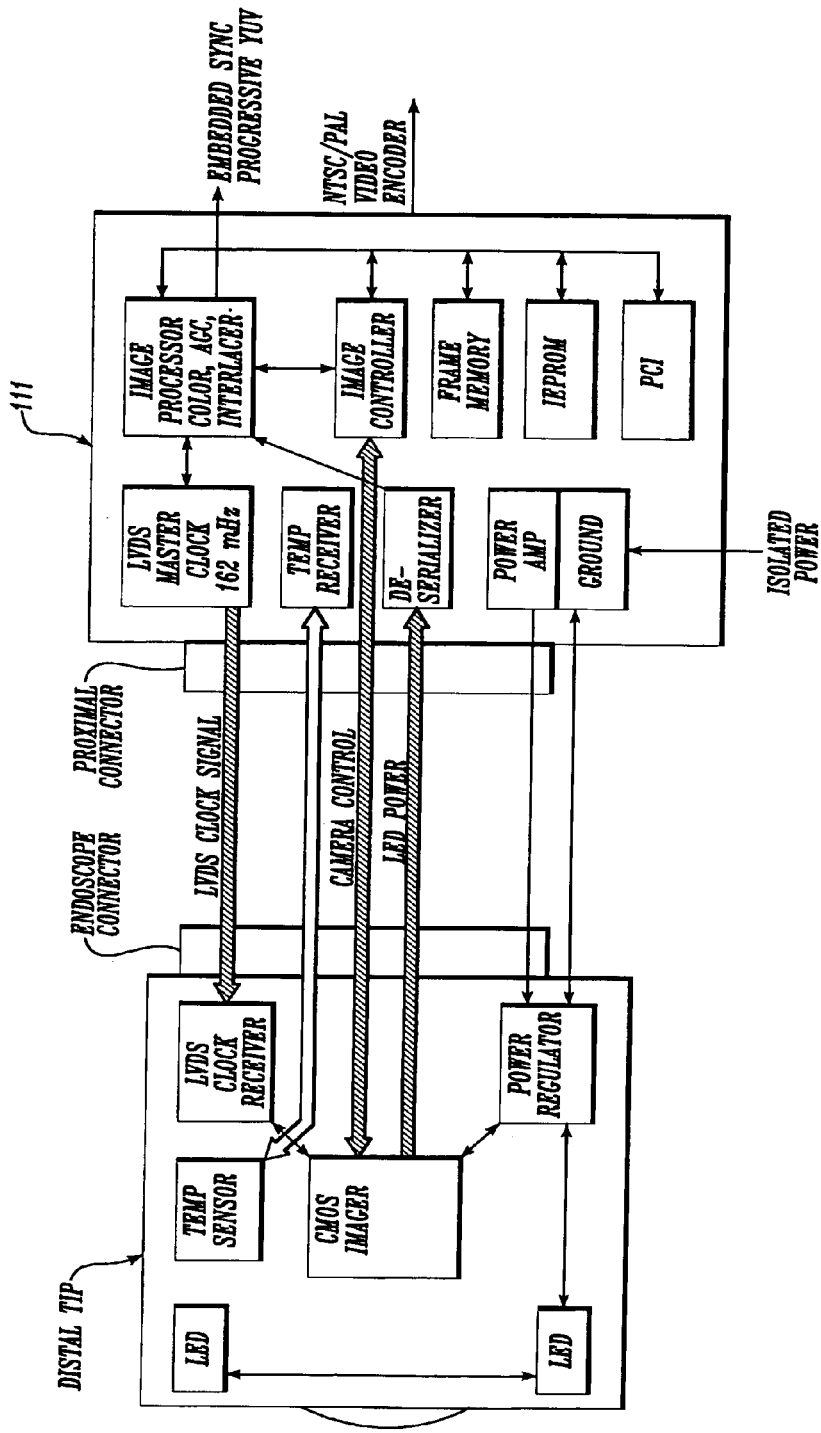
FIG. 3E illustrates the communication of data and control signals between a camera control card in the control cabinet and a remote image sensor at the distal tip of the endoscope in accordance with another embodiment of the present invention.

FIG. 3E shows the signals that may be transmitted from the camera card 111 to the image sensor and associated devices at the distal tip of the endoscope. The camera card 111 receives isolated power and contains conventional circuitry for a sync and color space conversion, automatic gain control, white balance initialization, pixel correction interlacer and a frame memory. Circuits are provided for low voltage differential signaling (LVDS). The camera card III contains an amplifier that drives the illumination light sources, such as LEDs. The camera card 111 provides an LVDS master clock signal to an LVDS clock receiver that is coupled to the CMOS image sensor at the distal end of the endoscope. By not including the master clock at the distal end of the endoscope, the cost of the imaging electronics for each endoscope is further reduced. The camera card 111 receives video and sync signals transmitted at 162 Mbps LVDS signaling, which are deserialized and provided to the on-board processor. In addition, the camera card receives thermistor signals received from a thermistor or other temperature sensor at the distal end of the endoscope. The camera card produces NTSC/PAL video signals that can be output to displays or other devices. In addition, the board provides embedded sync signals and progressive YUV Signals. The camera card 111 includes its own EPROM for storing firmware that may be updated, if necessary, and a frame memory for storing video frames.

Figure 3F:
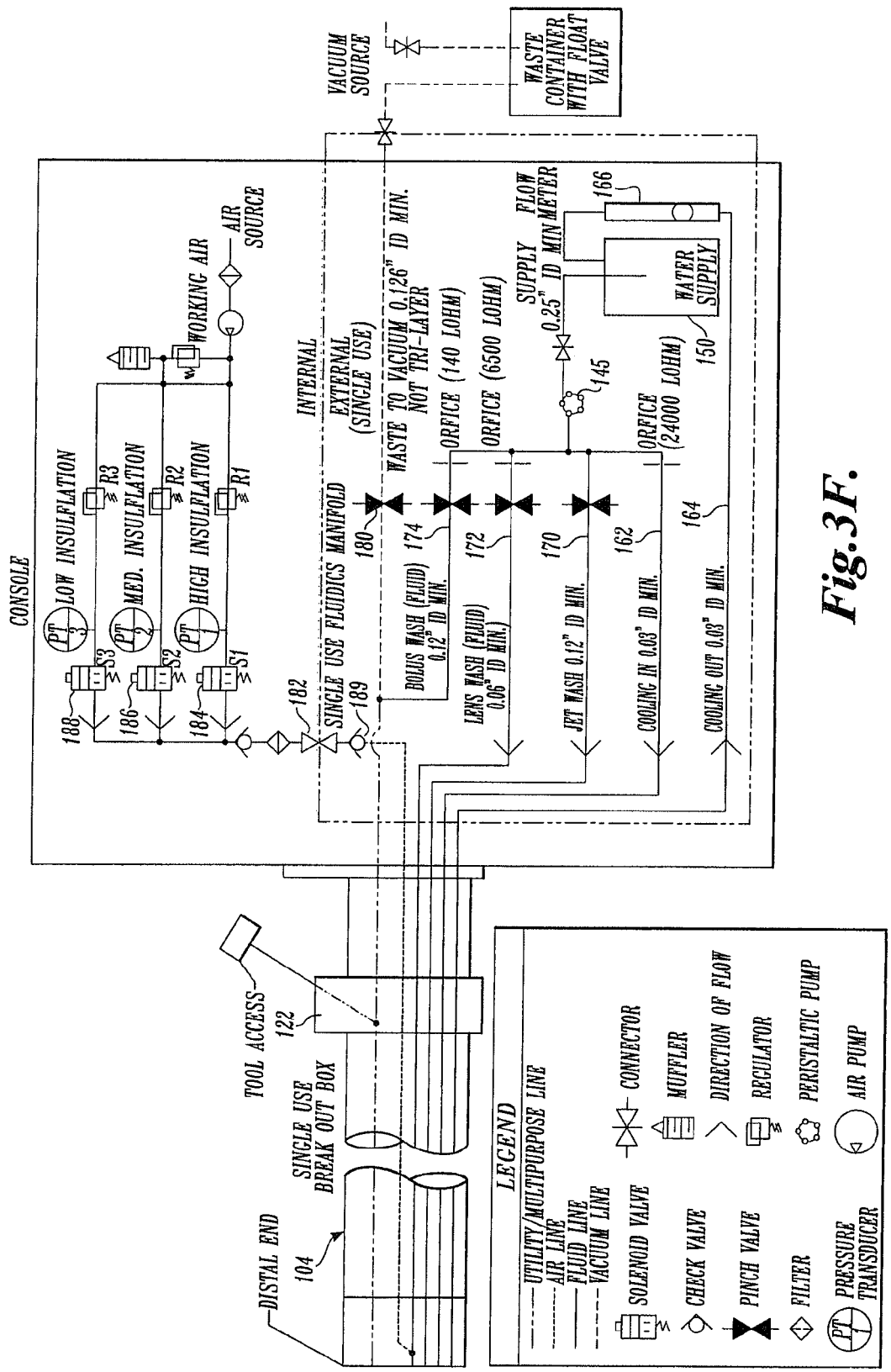
FIG. 3F is a fluidics diagram of a video endoscope shown in FIG. 3C.

FIG. 3F is a fluidics diagram of an embodiment of the endoscope 104 as shown in FIGS. 3C and 3D. As indicated above, a water supply 150, such as a plastic fluid reservoir containing a fluid such as sterilized water or saline, is used to supply water to the endoscope with a peristaltic pump 145. The water is pumped into a tube or lumen 162 that delivers the water to a heat exchanger coupled to the LED illumination source. Water returning from the heat exchanger is received in a tube 164 and passed through a flow meter 166 back to the reservoir 150. In this embodiment of the invention, water is continually pumped through the heat exchanger to prevent the illumination sources from becoming too hot. The flow meter 166 provides a signal if water is not being pumped through the heat exchanger so that the operator may be warned to remove the endoscope from the patient and/or the LEDs may be turned off or their output intensity lowered to prevent a thermal hazard to the patient. In addition, the fluid reservoir may include electronic sensors, movable floats, windows, alarms, etc., to indicate the level of cooling fluid available and whether an additional supply of liquid should be provided. A temperature monitor, such as a thermistor, in the distal tip can provide warning of a potential thermal hazard.

In addition to providing cooling, water can be selectively applied to a tube 170 that provides a high pressure lavage for irrigating a patient lumen, as well as a lens wash tube 172 that cleans contaminants from the front of an imaging lens at the distal end of the endoscope. Water can also be selectively applied to a tube 174 that is connected to a working channel tube of the endoscope to clean the working channel, if necessary. The flow of water in each of the tubes 170, 172, 174 is selectively controlled by an associated valve which allows water to be pumped through the tube if desired. A valve 180 controls the application of vacuum to a working channel tube in the endoscope to remove irrigation liquid, debris, or other contaminants from the patient, if desired. A valve 182 controls the supply of air or other bio-compatible gas to an insufflation lumen, which in an embodiment of the invention is the same tube as the lens wash tube 172 at the distal end of the endoscope. The air can be provided to the patient under a variety of pressures using solenoid valves 184, 186, 188 in line with regulators or an electronically controlled regulator or programmable array of regulators that provide air at different pressures and are connected in parallel to an air or gas source. The pressure of air delivered to the lens wash tube 172 can be adjusted by selectively opening a combination of the valves 184, 186, 188. A check or anti-siphon valve 189 is in line with the air supply line to prevent any back flow of air or liquids from the endoscope into the air delivery mechanism.

Figure 3G:
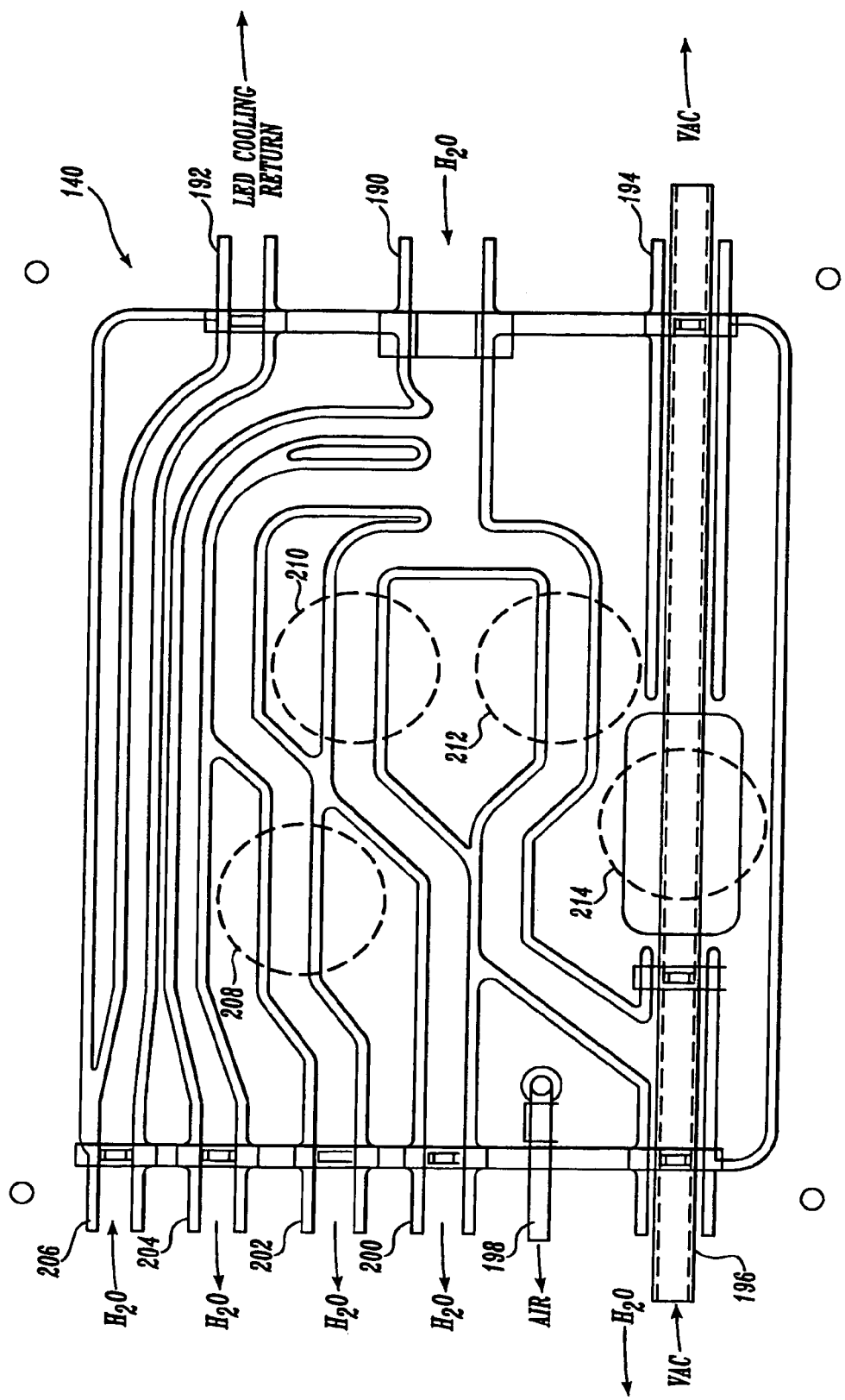
FIGS. 3G and 3H illustrate flexible manifolds for use in an embodiment of an endoscope of the present invention.

FIG. 3G shows one embodiment of a manifold 140 that directs air, water and/or vacuum to the various tubes or lumens within the endoscope. In one embodiment of the invention, the manifold is formed of two sheets of a thermoplastic material such as polyurethane that are RF welded or otherwise bonded to form a series of passages or channels between the sheets. Pinch valves or side clamps may be used on the vacuum line to prevent uncontrolled vacuum when connecting or disconnecting the connector to the control cabinet. Pinch valves are placed over the passages or channels and are selectively opened or closed to control the delivery of fluids, air or vacuum to the different tubes in the endoscope. In one embodiment, the manifold 140 has three connectors on one side and six connectors on the other side. On one side, a connector 190 receives water from the water reservoir 150. A connector 192 is connected to a tube that returns the water from the heat exchanger at the distal tip to the water reservoir 150, and a connector 194 is connected to a collection jar 160 that is in-line with the vacuum source. Pinch valves are preferred because the valve actuator components do not need to come into contact with the water or other fluids within the endoscope and they allow the wetted component to be single use. In addition, pinch valves provide for a simple valveless design.

In the embodiment shown, a connector 196 is connected to the working channel to supply water to or apply vacuum to the working channel. A connector 198 is connected to the insufflation tube. A connector 200 is connected to the high pressure lavage tube in the endoscope. Connectors 204 and 206 are connected to the tubes that supply water to and return water from the heat exchanger that cools the LED illumination sources.

Water entering the manifold at the connector 190 is allowed to flow in four different paths. Fluid flow through three of the paths is selectively controlled with solenoid valves that pinch the manifold 140 at locations 208, 210, 212 that are over the passages in the manifold. In one embodiment of the invention, water is always pumped through the heat exchanger that cools the LED illumination sources. By selectively activating the solenoid valves at the locations 208, 210, 212, water can be supplied to the other tubes in the endoscope.

In addition, the manifold 140 includes a support tube or other straw-like structure that maintains the passage open between the connectors 196 and 194 such that vacuum does not collapse the manifold 140 when a solenoid valve that is at a location 214 between the connectors 194 and 196 is released. The tube or straw also includes at least one perforation (not shown) to allow liquid to flow into the working channel if desired.

After use, the manifold 140 is removed from the tubes that supply water and vacuum, etc., and is disposed of along with the rest of the endoscope. The flexible manifold bag 140 forms an inexpensive device for controlling the application of fluids or air to the endoscope while preventing the fluids from coming in contact with non-disposable portions of the video endoscope system itself.

Figure 3H:
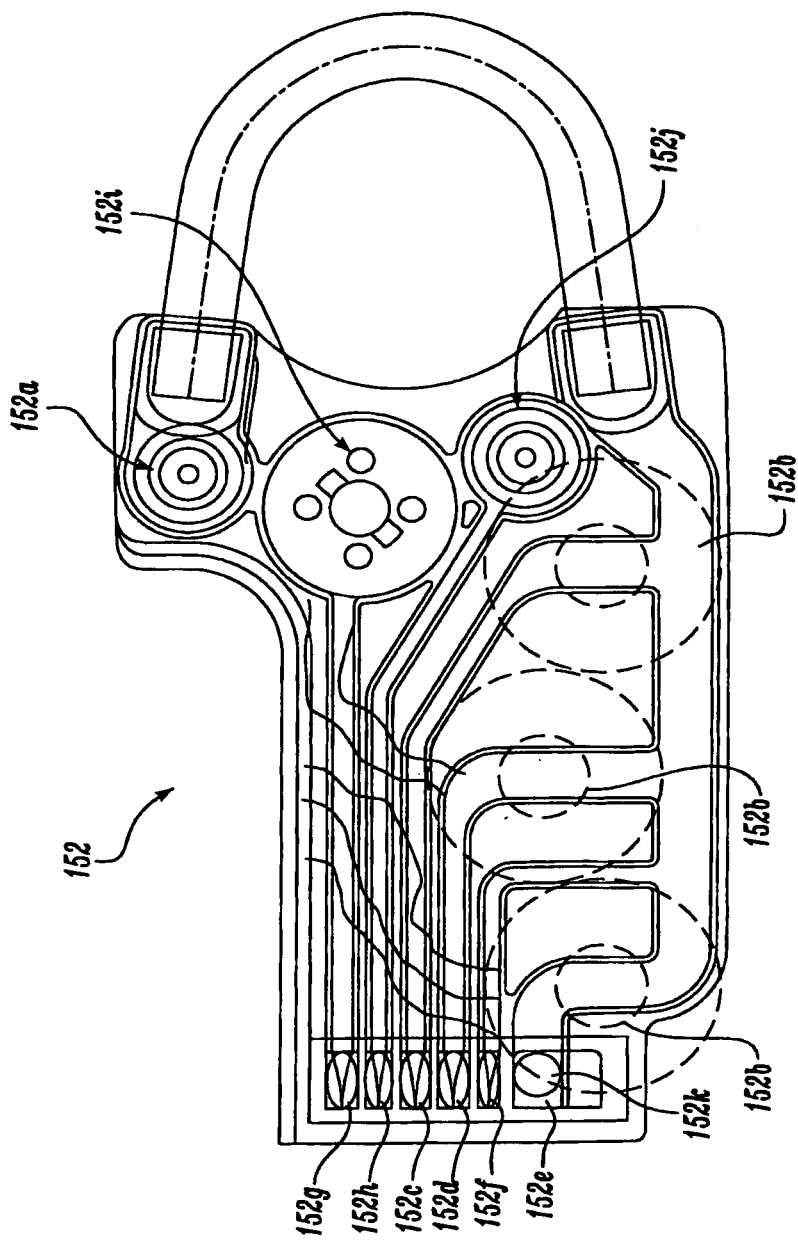

FIG. 3H shows another embodiment of a flexible manifold 152. Fluid enters the manifold 152 from the fluid reservoir through an inlet 152a. Fluid is pumped into tubing and the fluid path is selectively controlled by a series of pinch valves 152b. Fluid is allowed to flow selectively through a line 152e for a bolus wash, through a line 152c for a lens wash and through a line 152d for a jet wash. Fluid continuously flows out through a line 152f to a heat exchanger in the distal tip for LED cooling. Fluid returns from the heat exchanger through line 152h from which is flows through a flowmeter (not shown), and returns back to the fluid reservoir through a fluid outlet 152j.

Figure 4A:
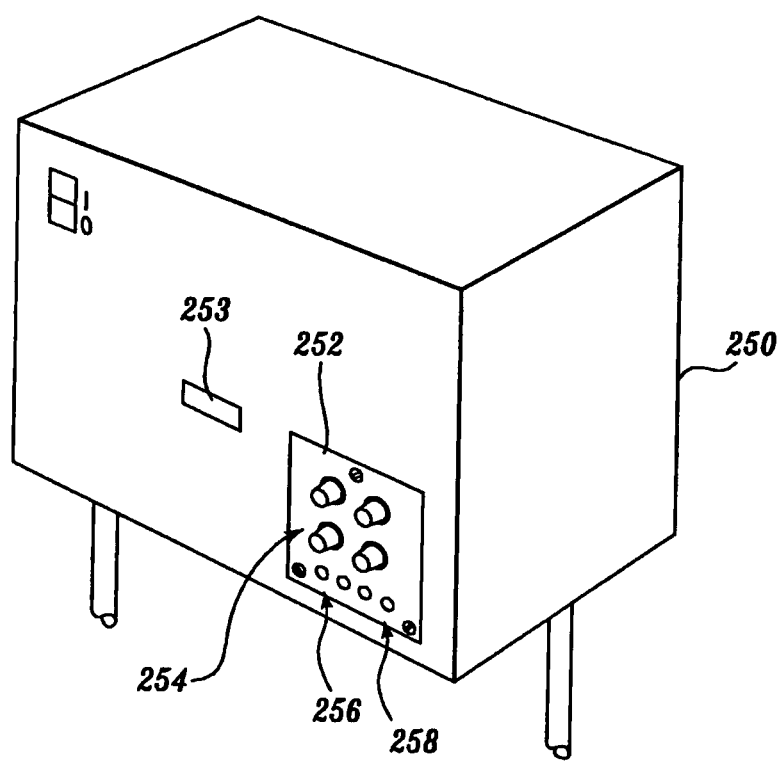
FIG. 4A illustrates an embodiment of a connector on a control cabinet for connecting to an endoscope.

FIG. 4A illustrates one embodiment of a connector for securing the proximal end of the endoscope to a control cabinet 250 prior to performing an endoscopic examination. The control cabinet 250 includes an exterior connector 252 having a number of shafts 254 that are coupled to the servo motors of the type shown in FIGS. 3A, 3B, and 3C. Each shaft 254 is shaped to be received in a corresponding spool on which the control cables are wound. Also included in the connector 252 are connections to the insufflation and irrigation valves 256 and a vacuum valve 258 to provide air, water and vacuum to the endoscope.

Figure 4B:
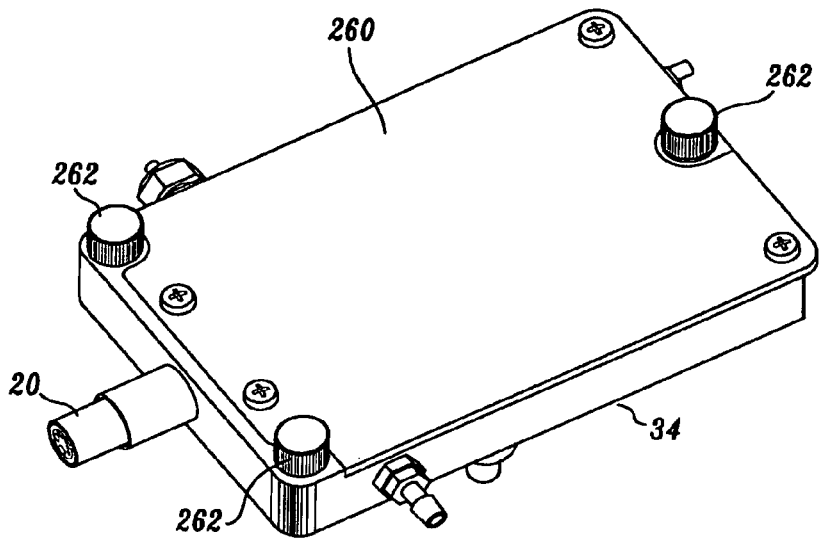
FIGS. 4B-4D illustrate an embodiment of a connector for connecting the proximal end of an endoscope to a control cabinet.
Figure 4C:
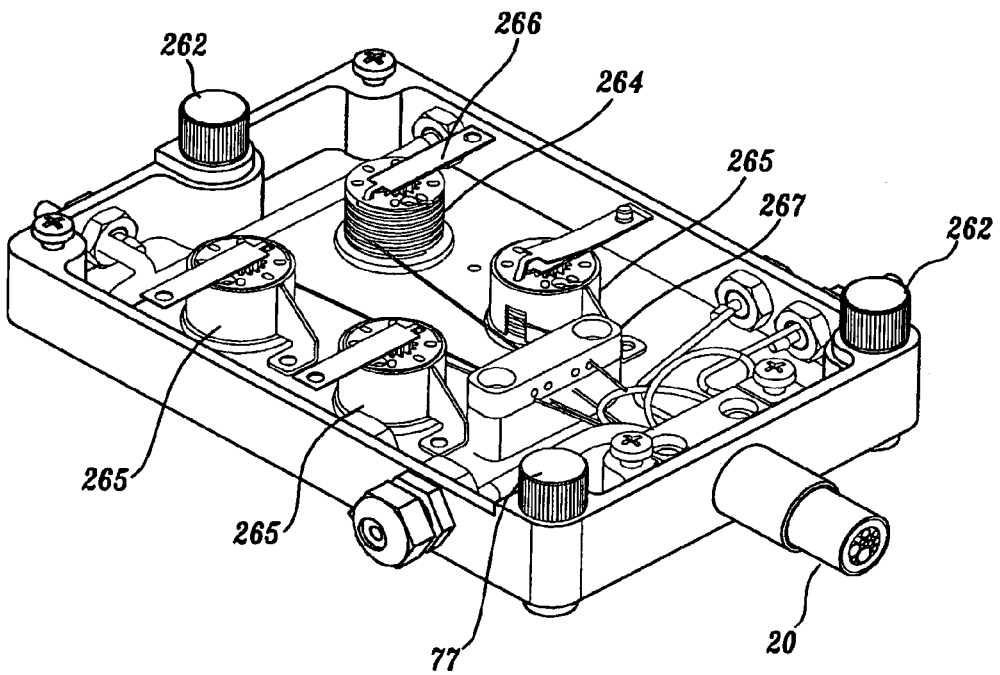

FIGS. 4B and 4C illustrate one embodiment of a connector 260 used to secure the proximal end of the endoscope 20 to the control cabinet 250. The connector 260 includes a number of thumbscrews 262, a form-fitted closure door, or other quick release mechanisms that allow the connector 260 to be easily secured to the exterior connector 252 on the exterior of the control cabinet 250. As shown in FIG. 4C, the connector 260 includes a number of spools 262 about which the control cables are wound. Each spool is preferably threaded or grooved to prevent the control cables from binding on the spool during use. A sheave or flange 265 may surround a portion of the spool to keep the control cables against the spool and within the groove and to aid in supporting the spool within the connector 260. In one embodiment of the invention, the spools are prevented from rotating and thus the cables from unwinding when the connector 260 is not engaged with the control cabinet 250 by brakes 266 having pins that fit within corresponding slots in the spools. Once the connector 260 is mounted to the control cabinet 250, the brakes 266 are disengaged from the spools such that the spools can be moved by the servo motors. A clamp 267 can be used to secure the proximal end on an outer jacket that covers the control cables. Electrical connections for the light sources and image sensor as well as connections to the air and water valves are placed on the sides of the connector 260 or on the rear face of the connector 260 to engage the valves, as shown in FIG. 4A.

Figure 4D:
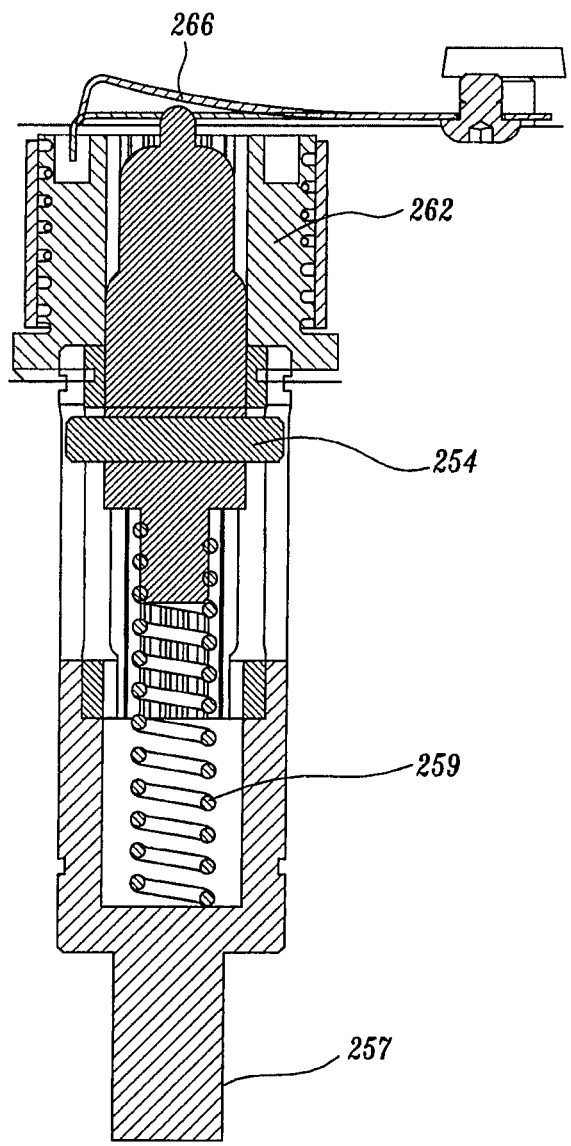

FIG. 4D illustrates a cross-sectional view of a splined shaft 254 fitted within a spool 262 with a splined bore. The shaft 254 is supported by a cylinder 257 having a spring 259 therein such that the shaft 254 is free to move within the cylinder 257. The cylinder 257 is coupled, either directly or through a clutch, to the servo motors within the control cabinet. The spring 259 allows the shaft 254 to float such that the shaft can more easily align and engage the mating surface of the spool 262 when the connector is attached to the control cabinet 250.

Upon insertion of the shaft 254 into the spool 262, the brake 266 is released, thereby allowing the spool 262 to be moved by rotation of the cylinder 257. In some instances, the brake 266 may be omitted, thereby allowing the spools 262 to freely rotate when the connector 260 is not engaged with the control cabinet 250.

Figure 4E:
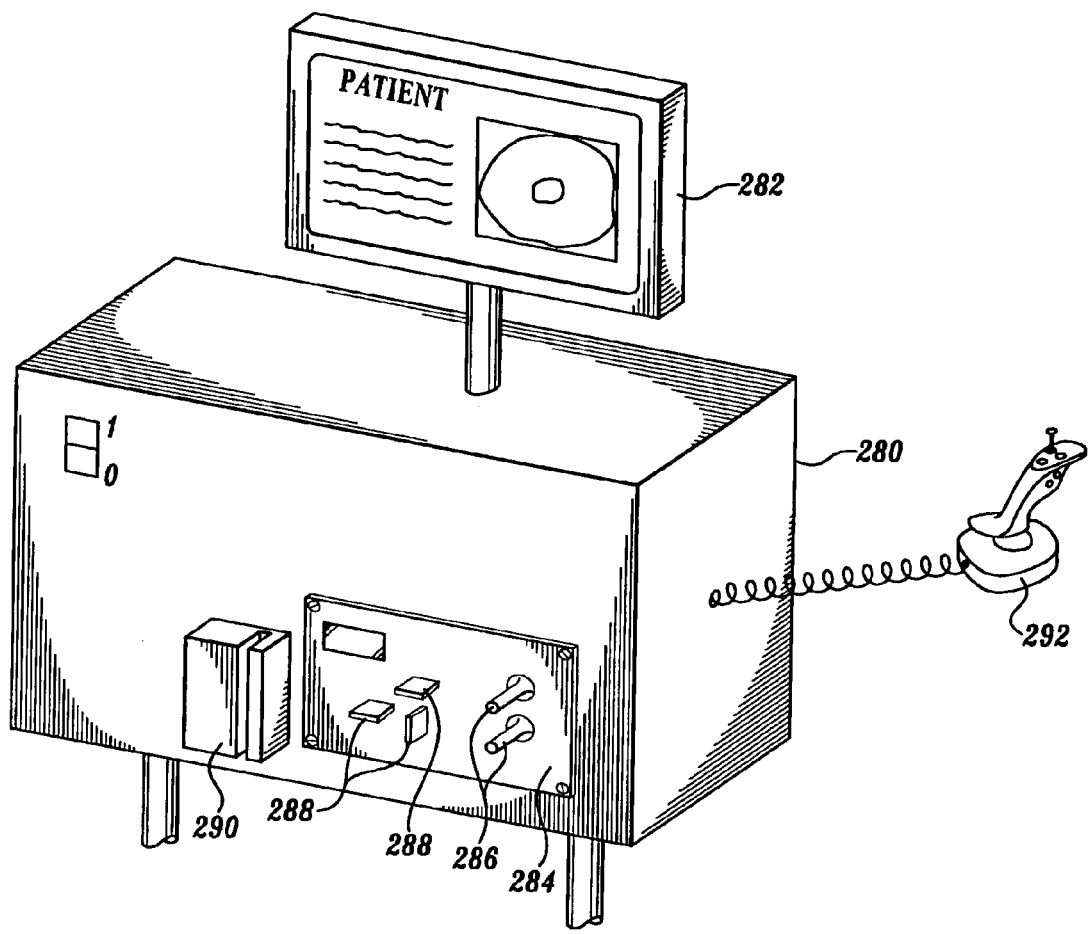
FIG. 4E illustrates another embodiment of a control cabinet with a connector for connecting to an endoscope.

FIG. 4E illustrates another embodiment of a control cabinet 280 having a display 282 upon which a graphical user interface including patient data and video or still images produced from the endoscope are presented. A connector 284 is provided on the exterior of the control cabinet 280 for connecting the proximal end of the endoscope. The connector 284 includes a number of shafts 286 that are coupled to the servo motors within the control cabinet. A number of pinch valves 288 are provided to control the flow of air, water, and vacuum through the manifold that connects the fluid reservoir, vacuum source, and air supply (not shown) to the tubes in the endoscope. A peristaltic pump 290 is provided for pumping liquid through the endoscope as described above. A joystick handheld controller 292 is connected to the control cabinet 280 so that an operator can enter commands concerning the operation of an endoscope and its orientation.

Figure 4F:
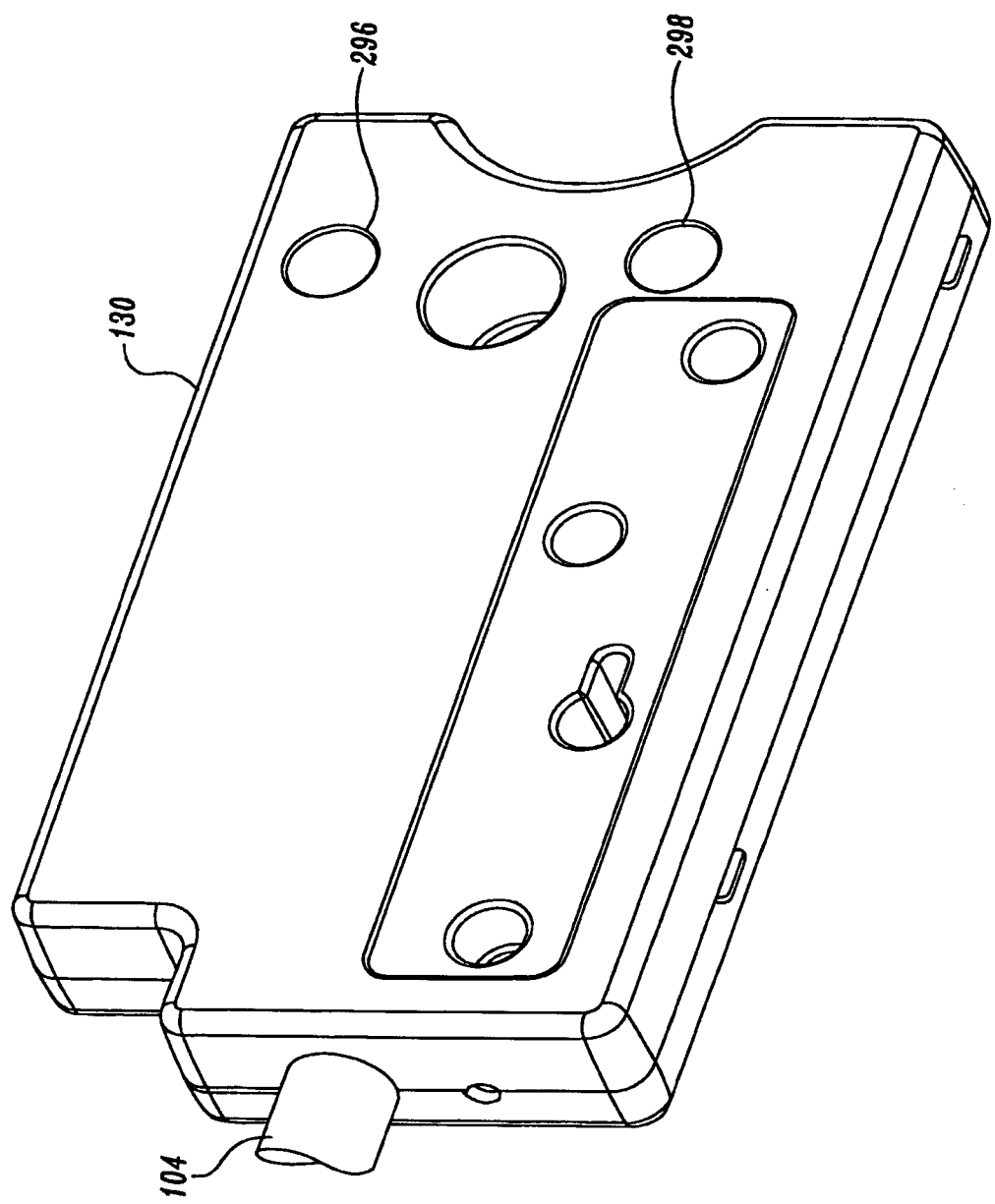
FIG. 4F illustrates a surface of a proximal connector that engages a control cabinet in accordance with an embodiment of the present invention.

FIG. 4F shows the rear surface of one embodiment of a proximal connector 130 that couples the endoscope to the control cabinet. The proximal connector may be seated into a movable door on the control cabinet, which is then closed to connect the connector 130 to the control cabinet. As discussed above, the connector 130 has an electrical connector therein that mates with a corresponding electrical connector on the control cabinet to transfer LVDS signals, including an upstream clock signal to the image sensor, power and grounds to the illumination LEDs, and regulated power for the image sensor. Electrical signals received back from the endoscope include a thermistor signal, and LVDS formatted, serialized video and sync data. Water inlet port 296 and water outlet port 298 supply fluids to a manifold within the proximal connector.

Figure 4G:
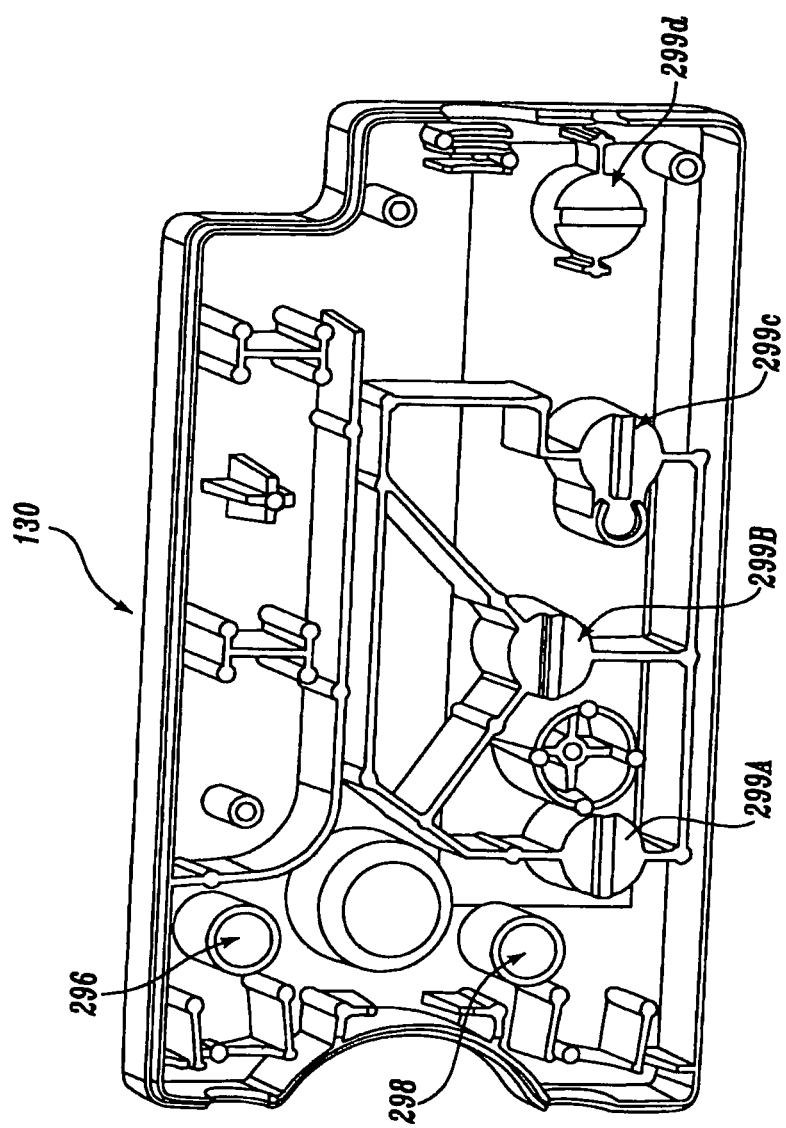
FIG. 4G illustrates an interior of a proximal connector in accordance with one embodiment of the invention.

FIG. 4G shows a cross-sectional view of the proximal connector 130 shown in FIG. 4F. As shown, a series of raised knobs with anvils 299A, 299B, 299C, 299D are located along one side of the proximal connector 130. The sharp edges on the anvils 299A-299C function to provide a backing to the flexible manifold bag inside the proximal connector housing and allow the solenoid valves to pinch the manifold and restrict the flow. The raised knob and anvil 299D provides a support to the vacuum tube under the manifold in the proximal connector housing to allow the solenoid valve to pinch the tube and control the vacuum.

Figure 5A:
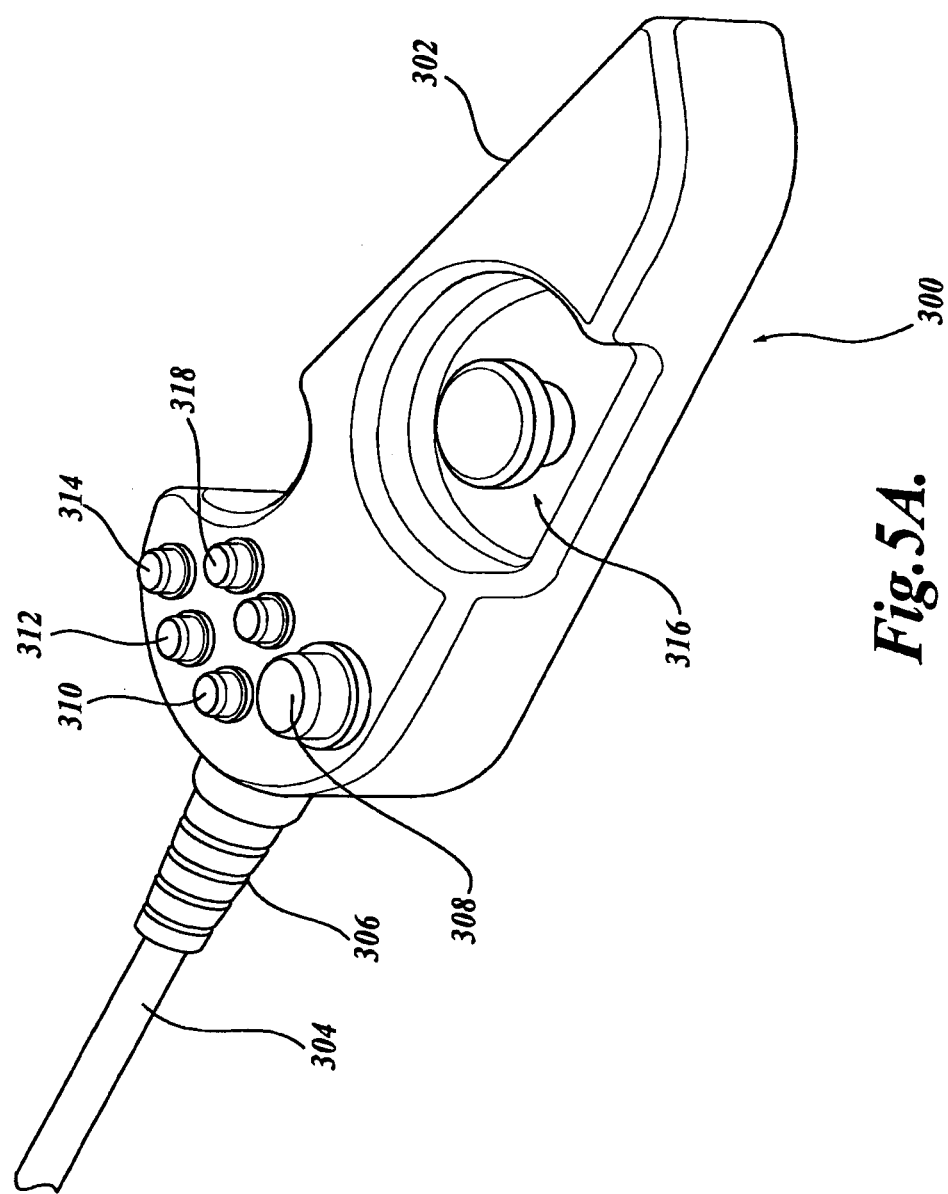
FIG. 5A is a detailed view of one embodiment of a handheld controller for use with a video endoscope of the present invention.

FIG. 5A illustrates various controls located on one embodiment of a handheld controller 300 in accordance with the present invention. The handheld controller 300 includes a controller body 302 that, in a parallel embodiment of the invention, is coupled to a control cabinet by an electrical cord 304, a wireless radio frequency channel, an infrared or other wireless or optical link. If the connection is made with an electrical cable, a strain relief 306 is positioned at the junction of the electrical cable 304 and the body 302 of the controller to allow suitable flexing and bending of the electrical wires within the electrical cable 304. In a serial embodiment, the connection of the handheld controller 300 to a control cabinet is made with a sheath that includes both the wires to transmit signals to the motion controllers and imaging system, as well as lumens to carry the insufflation air/gas and irrigation liquid. In addition, the control cables of the endoscope engage cables that are connected to the actuators in the motion control cabinet through the handheld controller 300. If used with a manual handle, the connection to the control cabinet is made with a sheath that includes wires to transmit signals to and from the image sensor, the illumination LEDs and lumens to carry the insufflation air/gas and irrigation/cooling liquid.

Positioned in an ergonomic arrangement on the handheld controller 300 are a number of electrical switches. An articulation joystick 308 or other multi-positional device can be moved in a number of directions to allow the physician to orient the distal tip of the imaging endoscope in a desired direction. In order to guide the imaging endoscope manually, the physician moves the joystick 308 while watching an image on a video monitor or by viewing the position of the distal tip with another medical imaging technique such as fluoroscopy. As the distal tip of the endoscope is steered by moving the joystick 308 in the desired direction, the physician can push, pull and/or twist the endoscope to guide the distal tip in the desired direction.

A camera button 310 is provided to capture an image of an internal body cavity or organ in which the endoscope is placed. The images collected may be still images or video clips. The images may be adjusted for contrast or otherwise enhanced prior to display or stored on a recordable media.

An irrigation button 312 activates an irrigation source to supply a liquid such as water through an irrigation lumen of the endoscope. The liquid serves to clean a window in front of an image sensor and/or the light source at the distal end of the endoscope as well as an area of the body cavity. An insufflation button 314 is provided to activate the insufflation source to supply air/gas through a lumen of the endoscope. The supply of the insufflation gas expands portions of the body cavity surrounding the distal tip of the endoscope so that the physician can more easily advance the endoscope or better see the tissue in front of the endoscope.

In one embodiment of the invention, the body 302 of the handheld controller 300 also includes a detachable joint such as a thumb screw 316 for securing the handheld controller 300 to the breakout box as indicated above. A corresponding socket or set of threads on a breakout box receive the thumb screw 316 in order to join the two parts together. One or more additional buttons 318 may also be provided to activate additional functions such as recording or printing images, adjusting light intensity, activating a vacuum control valve or providing a variable braking drag on the control cables that provide the up, down, left, right movement of the distal tip, etc., if desired.

Figure 5B:
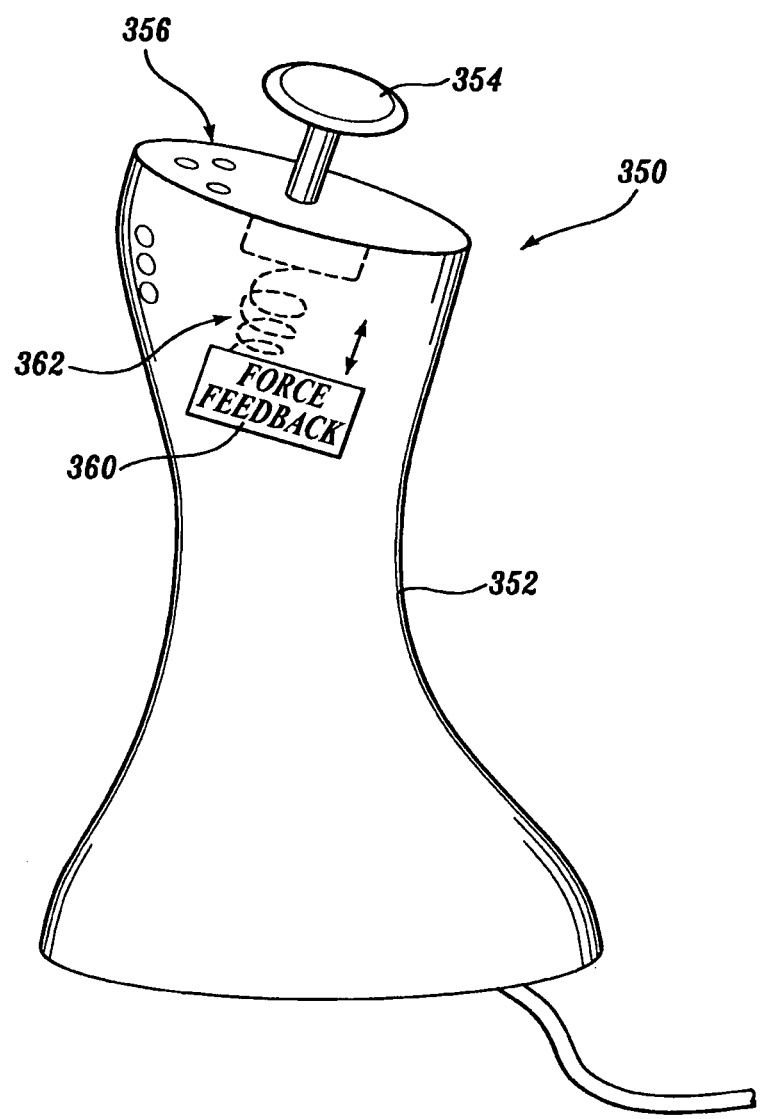
FIG. 5B illustrates an embodiment of a joystick style controller including a force feedback mechanism for use with an endoscope of the present invention.

FIG. 5B illustrates another embodiment of a hand held controller by which the operator can enter commands to control the operation of the control cabinet and endoscope. The controller 350 includes a handle 352 that is ergonomically shaped to allow the user to control the operations with his or her thumb and/or fingers. A joystick 354 is located on the top of the controller 350 such that the user can steer the endoscope by moving the joystick with their thumb. A number of control buttons 356 can be activated with the user's thumb or fingers to control other operations of the endoscope such as supplying air for insufflation or water/vacuum to the lumens in the endoscope adjusting the illumination source intensity, etc. The controller 350 also includes a force feedback mechanism 360 that applies a variable force to a spring 362 that biases the joystick 354. The force applied by the feedback mechanism 360 is varied in proportion to the force required to steer the endoscope. For example, the endoscope may be positioned against a tissue wall, or may have a number of loops along its length. Therefore, the user can be given a tactile indication of the force required to steer the endoscope by varying the force placed on the spring 362 by the feedback mechanism 360.

As indicated above, in one embodiment of the invention, the servo motors implement a position-to-rate control algorithm, whereby the position of the joystick 354 is translated into a rate of change of position in a desired direction in the distal tip. Therefore, as the user presses the joystick in any direction, the return force that is applied by the force feedback mechanism 360 to the spring 362 can be varied as a function of the drive motor torque required to move the control cable and varying the force on the spring also varies the force that the spring applies to the joystick. The force that the spring applies to the joystick is felt by the user through the joystick and gives the user a tactile indication of the level of force being applied to move the distal tip in the direction being commanded by the user.

Figure 5C:
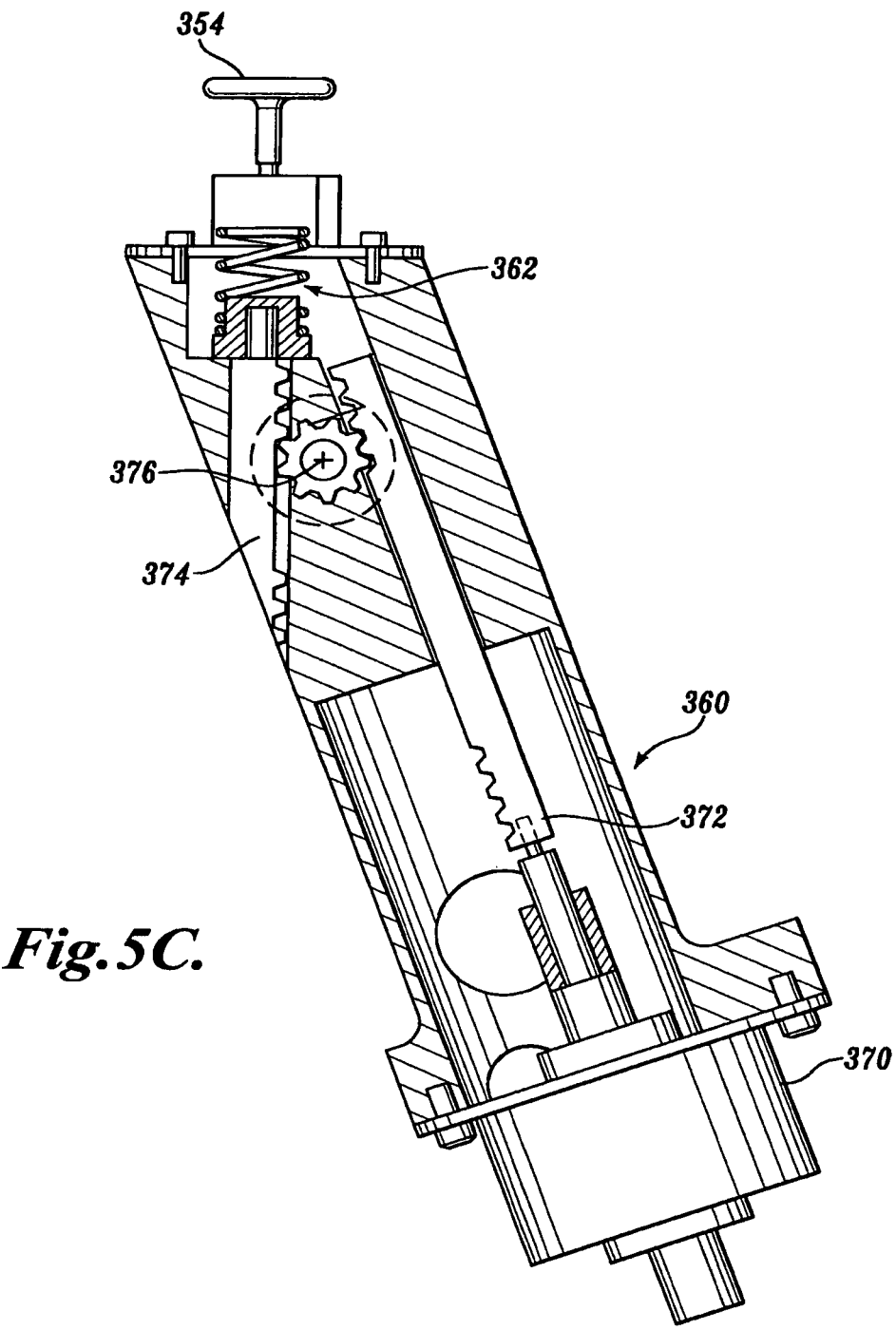
FIG. 5C illustrates one embodiment of a mechanism for providing force feedback to a joystick of the type shown in FIG. 5B.

FIG. 5C illustrates one mechanism for providing a force feedback mechanism 360 within the handheld controller 350. Within the joystick is a motor 370 that drives a rack and pinion mechanism including a first rack 372 that is directly coupled to the motor 370 and a second rack 374 that is directly coupled to the pretension spring 362. Rotation of the motor 370 drives a screw-type mechanism (not shown) which moves the first rack 372 up or down. A pinion gear 376 translates longitudinal motion of the first rack 372 into longitudinal motion of the second rack 374, which in turn adjusts the pretension on the spring 362. In the embodiment shown, two racks are needed due to the orientation of the joystick with respect to the longitudinal axis of the hand held controller 350. However, other configurations could be used if the joystick were oriented differently in the hand held controller. For example, linear motor drive joysticks could be configured to provide rapid force feedback to the user.

Similarly, other structures and/or materials, such as elastomers or flexural structures can be used to replace the spring entirely and a force can be applied to one area of the plastic material to create a similar force where the plastic contacts and biases the joystick. Similarly, variable torque motors can be coupled directly to the joystick and the torque of the motors adjusted in accordance with the tension of the control cables to directly transmit a force through the joystick to the user. The use of two motors with the motors acting on orthogonal respective axes of the joystick movement can create force feedback signals in response to all possible directions of joystick movement. This sort of use and arrangement of direct drive motors can be similarly used to feedback position of the distal tip. In this arrangement, position controlled motors would be used instead of torque controlled motors. The positions of the control cables or the positions of the servo motors driving these cables are used to compute the approximate position of the distal tip. The position controlled motors are driven to make the joystick position follow the computed position of the distal tip. If the operator attempted to move the tip and the motion of the tip were blocked by its environment, then the operator's movement of the joystick would be resisted by forces applied by the position controlled motors to make the joystick position correspond with the tip position.

Although the embodiment shown discloses a motor and a rack and pinion gear system to change the compression of the spring 362 that biases the joystick 354, it will be appreciated that other mechanisms including hydraulic, or magnetic actuators could be used. Alternatively, as discussed above, pseudo-fluid devices such as thermoplastics can be used. By selectively compressing a thermoplastic material, its elasticity can change and be used to apply different pressures on a spring 362.

In another embodiment, not all the forces on the wires are fed back to a user. In one embodiment, the system distinguishes the resistance of the shaft versus the resistance at the distal tip and only the resistance at the distal tip is fed back to a user.

To distinguish the forces on the shaft versus the forces at the tip, the tip is dithered in different directions. If the resistance is on the tip, then the resistance should be high only in one direction. If resistance is caused by loops in the shaft, then resistance should be equal in all directions. By comparing the forces in a processor and separating the forces required to move the distal tip, high forces can be prevented from building up at the tip. High motor torque can be used only to overcome resistance due to looping and not employed to bend the tip if it meets resistance. Therefore, higher forces are prevented from being built up on the tip, lowering the risk that the tip will perforate the anatomy or undesirably snap into position.

Figure 5D:
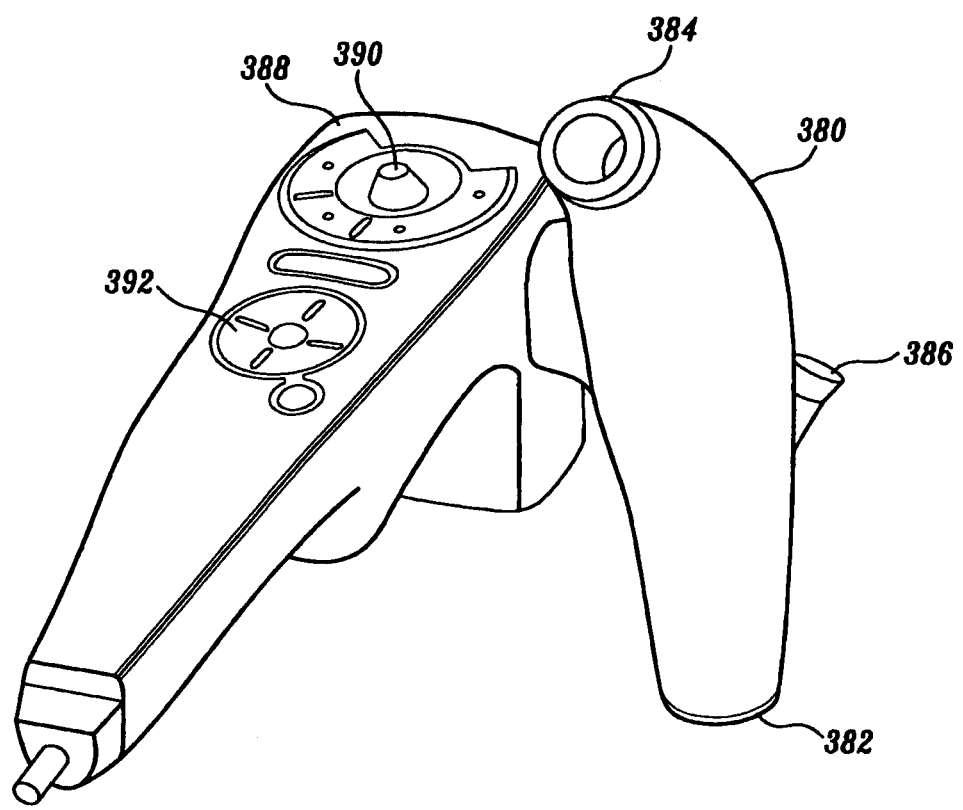
FIGS. 5D and 5E illustrate another embodiment of a breakout box and handheld controller of the present invention.
Figure 5E:
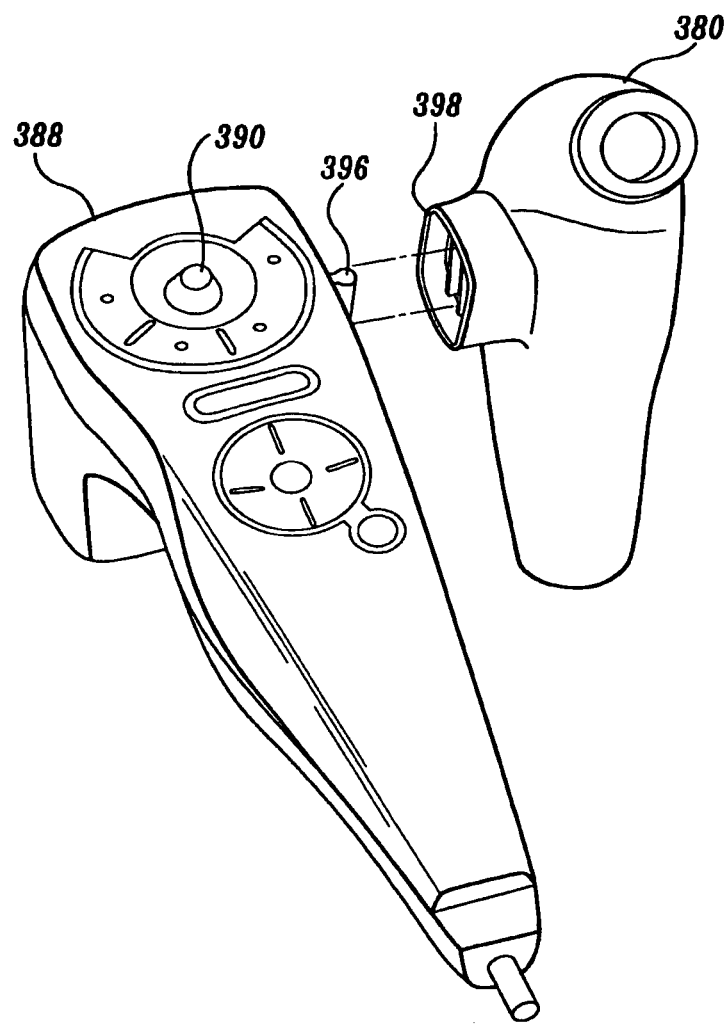
Figure 5F:
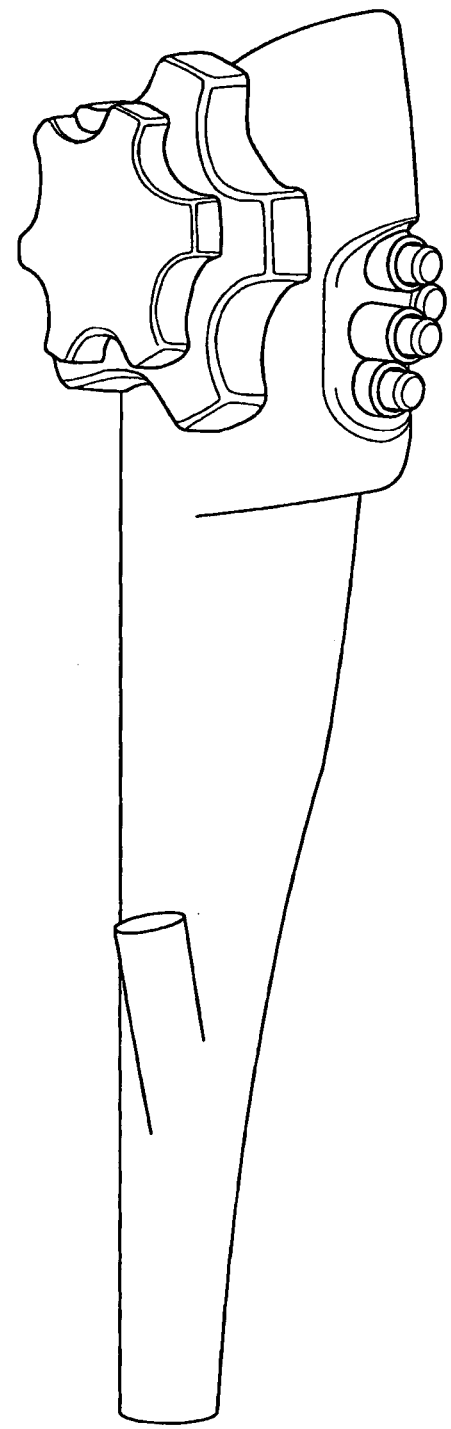
FIGS. 5F-5I illustrate one embodiment of a manual handle for use with an endoscope of the present invention.
Figure 5G:
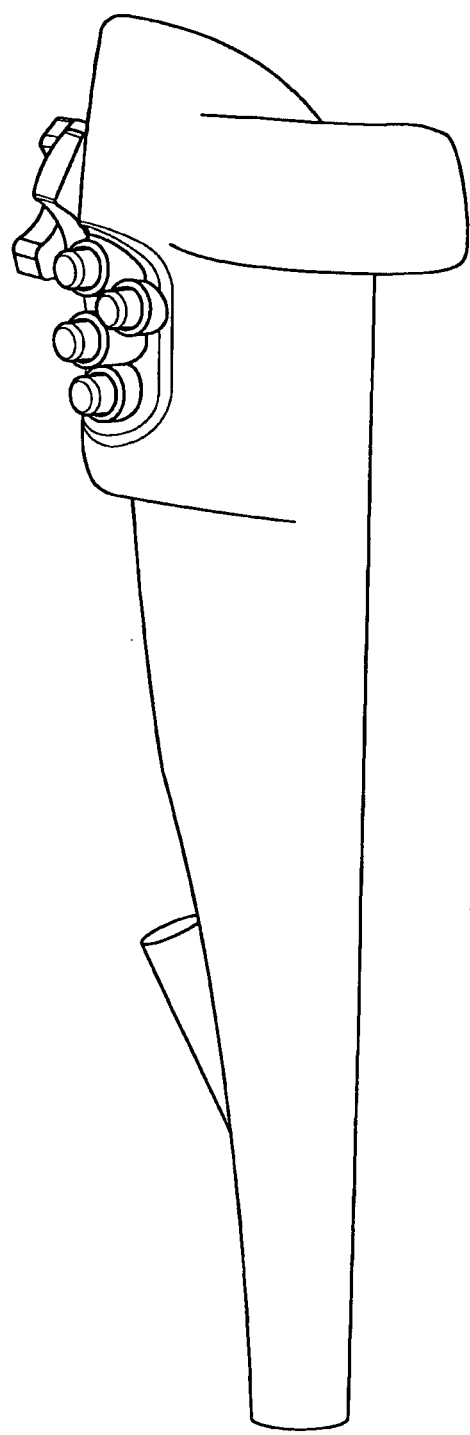
Figure 5H:
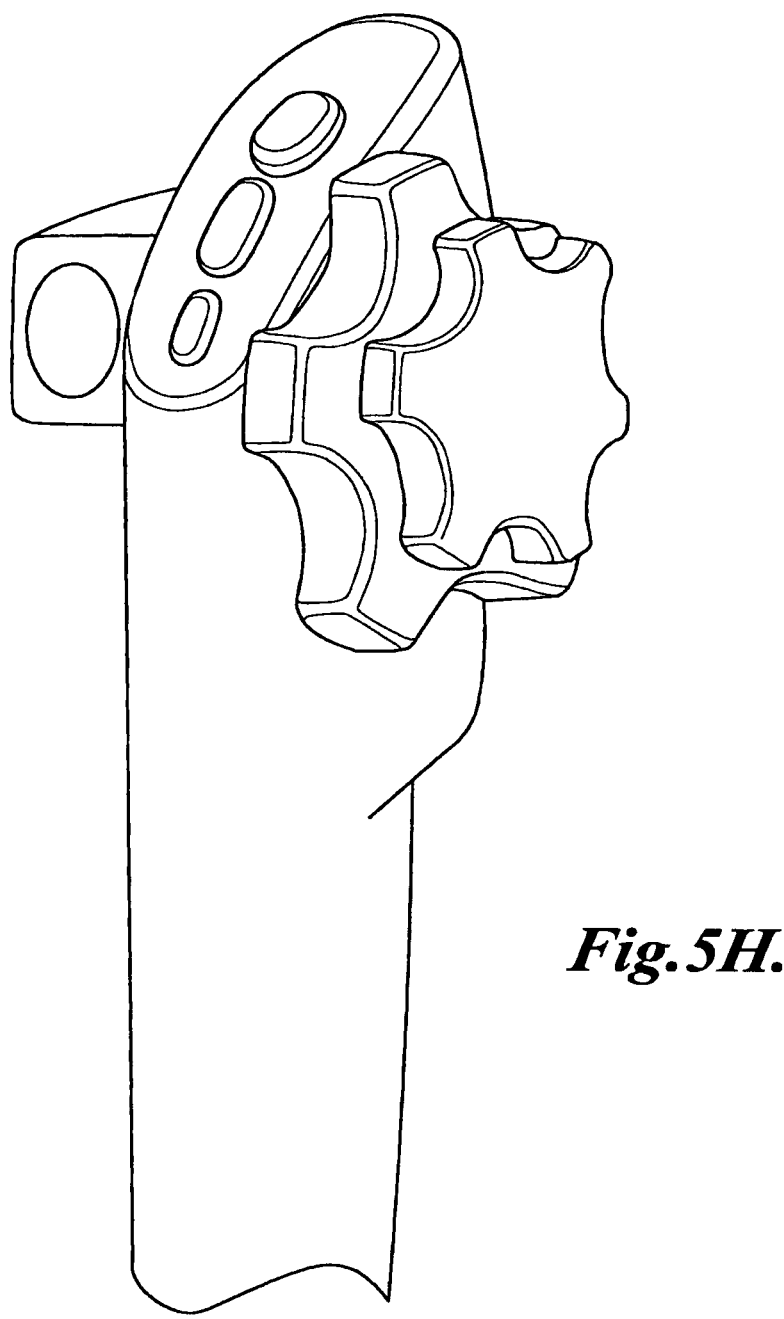

FIGS. 5D and 5E illustrate another embodiment of a breakout box and handheld controller. In this embodiment, a breakout box 380 has a distal end 382 and a proximal end 384. The breakout box is generally "banana-shaped" such that it fits ergometrically in a user's hand. In addition, the proximal end 384 of the breakout box 380 is oriented such that when the user has the controller in his or her hand and the palm is oriented horizontally with respect to the floor, the proximal end is pointed downwards toward the floor. Therefore, the proximal end of the endoscope shaft extending from the breakout box is angled away from the physician's forearm and is less likely to get in the way.

The breakout box 380 also includes an entrance to the working channel 386 having a cap thereon. The cap is positioned such that the entrance to the working channel does not face the physician in order to lessen the chances of the physician or nurse being sprayed by bodily fluids or other contaminants. The cap may be removable or integrated into the breakout box and may include a duck bill or tuey bohrs that enables a physician to effectively seal around a device to prevent air and fluid leakage. By removing the cap, a user can insert a tool into the working channel for receiving biopsies, applying medication, or performing other medical procedures.

Selectively coupled to the breakout box 380 is a handheld controller 388. The handheld controller includes a directional switch 390 that controls the orientation of a distal tip of the endoscope. Further buttons or controls 392 may be provided to allow the user to activate additional features of the endoscope or change operating parameters of the video endoscope system.

Other embodiments may not require the cap to be removed. The cap may consist of a duck bill valve which allows passage of the device but immediately seals itself once the device has been removed. This ensures that the user will never get sprayed if the bolus wash is applied while the cap is removed. Another design involves a screw cap which tightens down on the duck bill valve to hold the device steady at a precise location.

As shown in FIG. 5D, the handheld controller 388 is selectively coupled to the breakout box 380 by cooperating male and female joining mechanisms 396, 398. In the embodiment shown, the joining mechanisms comprise a tab which is elastically received in a corresponding slot. However, other attachment mechanisms could be used.

FIGS. 5F-5I illustrate one embodiment of a manual handle including rotatable knobs that tension the control cables to steer the distal tip of the endoscope. The manual handle includes a number of electronic switches that direct electronics in the control cabinet to activate various functions of the endoscope system, such as suction, air, lens wash, jet wash or low pressure lavage and bolus wash. Additional switches are provided to be thumb activated, such as a menu button and a multi-position switch for navigating menus on the display.

In one embodiment of the invention, several simple switches are used to control water, air, suction, lens wash image management, and graphical user interface (GUI) navigation. The switches are wired to a circuit board in the handle or connector with multiple wires. A microprocessor provides the button signals to the control cabinet on a few wires. The switches can be relatively inexpensive because the switches do not need to withstand repeated use or cleaning. In addition, other functions such as debouncing, etc., that might increase the cost of the switch can be provided within the control unit by dedicated hardware or software, for example.

Figure 5I:
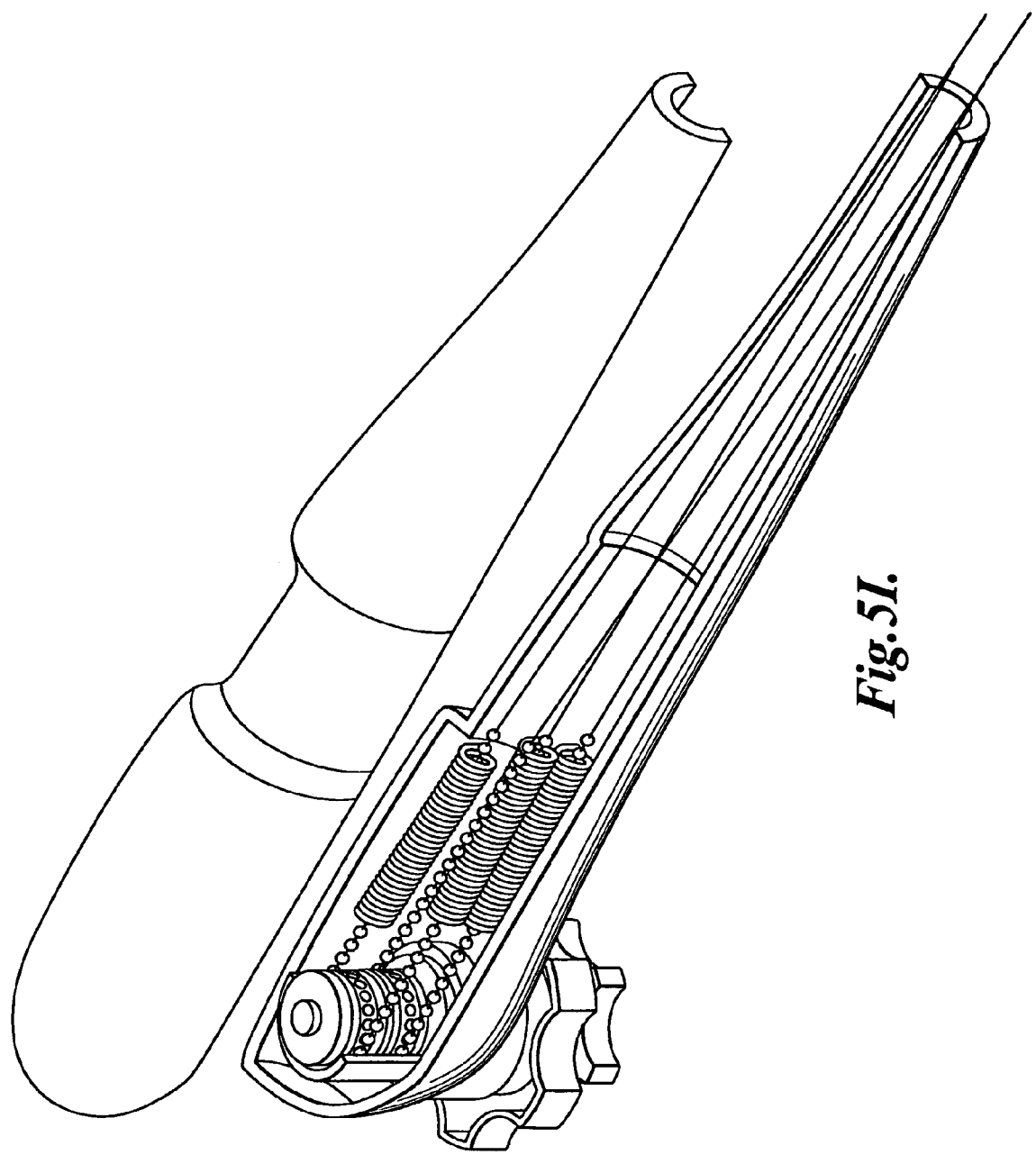

In one embodiment of the invention, the knobs on the handle are coupled to the control wires with a "bead chain" of the type commonly used with lamp pull-switches. The bead chain engages in a sprocket connected to the knobs. The force required to turn the knobs and the amount of rotation of the knobs required to articulate the tip can be controlled by adjusting the size of the sprocket. Larger sprockets will require more force to turn the knob but will require less rotation and will have higher force feedback. Smaller sprockets will require less force but more rotation. It is possible that a different size sprocket be used on the up/down axis than on the left/right axis. In one embodiment, the steering cables are connected directly to the bead chain. In other embodiments, the steering cables can be wrapped directly around the sprocket. In other embodiments (as shown in FIG. 5I), the bead chain is connected to the steering cable using a spring. The stiffness of the spring can be adjusted to maintain uniform tension in steering system when loops are created in the distal shaft during an endoscopic procedure. In other embodiments, the spring can be put on the end of the tightly wound spring coils which the steering cables run through. This springs may also be used to ensure that all disposable devices have the same feel to the user and prevent slack from building up in the devices during storage prior to use. This ensures that all devices will be responsive to the user and will not have slop.

A fixed stop may be placed on the sprocket, on the bead chain, on the pull cable or on the knobs to limit the rotation of the knob and avoid over articulating the tip.

An entrance to the working channel is positioned below the knobs to allow the insertion of tools into the working channel. The working channel port may be fixed to the manual controller housing or may be allow to translate along the main axis of the housing. Allowing the working channel port to translate, will prevent tensile forces from building up on the working channel when loops are created in the distal shaft.

The manual controller housing will allow space for excess length of bowden cables, electrical cables and utility tubes. This prevents tensile forces from building up on these components when loops are created in the distal shaft.

In other embodiments, the handheld controller may be fitted to a gripping mechanism that grasps the distal portion of the shaft. The operator can therefore secure the handheld controller to the shaft at various positions along its length in order to allow the physician to be closer to the patient.

Although the disclosed embodiments of the endoscope generally require an operator to control the orientation of the distal tip, the endoscope of the present invention may also be steered automatically. Images received by the imaging electronics are analyzed by a programmed processor to determine a desired direction or orientation of the distal tip of the endoscope. In the case of a colonoscopy, where the endoscope is advanced to the cecum, the processor controls the delivery of insufflation air/gas to inflate the colon. The processor then analyzes the image of the colon for a dark open lumen that generally marks the direction in which the endoscope is to be advanced. The processor then supplies control instructions to the servo controller such that the distal tip is oriented in the direction of the dark area so located.

In other modes, a processor in the control cabinet causes the distal tip of the endoscope to move in a predefined pattern. For example, as the endoscope is being withdrawn, the distal tip may be caused to move in a spiral search pattern such that all areas of a body cavity are scanned for the presence of disease. By using the automatic control of the distal tip, a physician only has to advance or retract the endoscope to perform an examination and concentrate fully on image interpretation.

Figure 6A:
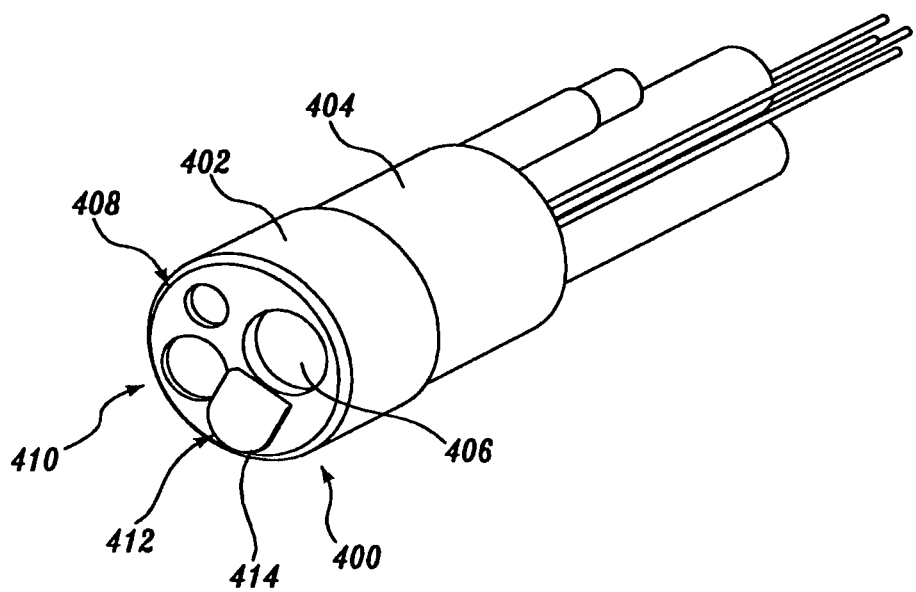
FIG. 6A illustrates an embodiment of a distal tip of an endoscope in accordance with the present invention.

As will be described in further detail below, the endoscope generally comprises a hollow shaft having one or more lumens formed of plastic materials, such as polyurethane or polyethylene, which terminate at the distal tip. The shape of the distal tip and shaft is usually cylindrical but can be made in other shapes to facilitate passage into a body cavity. In addition, the tube for the working channel may be supported with a spring in the area of the articulation joint to prevent kinking. In addition, the lumens may be reinforced with a spiral wound wrap of metal wire or polymer or glass fiber or tape. The lumens can have various cross-sectional shapes along the length such as circular, oval, asymmetrical, etc. The outsides surface of the tubes may be lubricated to help them slide relative to each other during articulation. Alternatively, 'frosted tubes' may be used to lower the coefficient of friction on the outside surface. The internal wall of all tubes will usually be smooth. One embodiment of the working channel involves a star shaped lumen rather than a circular lumen. This reduces the contact area with devices and allows devices pass through with less force. As shown in FIG. 6A, one embodiment of a distal tip 400 comprises a cylinder having a distal section 402 and a proximal section 404. The proximal section 404 has a smaller diameter than the diameter of the distal section 402 in order to form a stepped shoulder region. The diameter of the shoulder is selected such that shaft walls of the endoscope can seat on the shoulder region to form a smooth outer surface with the distal section 402. The distal face of the distal tip 400 includes a number of ports, including a camera port 406, one or more illumination ports 408, an access port for the working channel lumen 410, and a directional flush port 412.

Fitted within the camera port 406 is an image sensor (not shown) that preferably comprises a CMOS imaging sensor or other solid state imaging device and one or more glass or polymeric lenses that produces electronic signals representative of an image of the scene in front of the camera port 406. The image sensor is preferably a low light sensitive, low noise, CMOS color imager with VGA resolution or higher such as SVGA, SXGA, XGA, or UXGA, etc. If less resolution is desired, a ½ or ¼ VGA sensor could also be used. For conventional video systems, a minimum frame rate of 25 to 30 fps is required to achieve real-time video. The video output of the system is desirably transmitted to the console in a digital form, but may be in any conventional digital or analog format, including PAL or NTSC, or high definition video format.

The illumination ports 408 house one or more lenses/windows and one or more light emitting diodes (LEDs) (not shown). The LEDs may be high intensity white light sources or may comprise light sources at other wavelengths such as infrared (IR) red, green, blue or ultra-violet (UV) LEDs. With colored LEDs, images in different spectral bands may be obtained by illumination with any one or more individual colors. White light images may be obtained by the simultaneous or sequential illumination of the colored LEDs and combining individual color images at each illumination wavelength. If sequential illumination of colored LEDs is employed, as an alternative, a monochrome CMOS imager can be used. As an alternative to LEDs, the light source may be external to the endoscope and the illumination light delivered to the illumination port with a fiber optic bundle and traditional light sources. Alternatives to a LED source at the distal tip could include, for example, an incandescent lamp or lamps, or organic LEDs, photomic crystals, or laser sources.

The access port 410 is the termination point of the working channel or lumen of the endoscope. In one embodiment, the proximal end of the working channel terminates at the breakout box 26 as shown in FIG. 2. However, the working channel could terminate nearer the proximal end of the endoscope.

The directional flush port 412 includes a cap 414 that directs liquid and air supplied through an irrigation and insufflation lumen across the front face of the distal tip 400 in the direction of the camera port 406 and/or the illumination ports 408. The cap 414 thereby serves to rinse, clean and dry the camera port 406 and the illumination port 408 for a better view of the internal body cavity in which the endoscope is placed. In addition, the flushing liquid cleans an area of tissue surrounding the distal end of the endoscope.

FIGS. 6B-6I illustrate another embodiment of an imaging assembly that forms the distal tip of the disposable endoscope in accordance with the present invention. The imaging assembly is low cost, compatible with inexpensive assembly techniques, and performs comparably to more expensive imaging mechanisms such that an operator finds the endoscope operation familiar for the examination of patients.

Figure 6B:
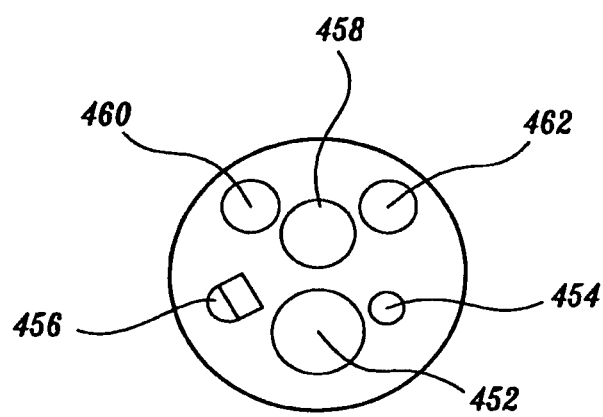

As shown in FIG. 6B, the distal end of the endoscope includes a distal cap having a number of openings on its front face. The openings include an opening to a working channel 452 and an opening 454 for a low pressure lavage, whereby a stream of liquid can be delivered through the endoscope for removing debris or obstructions from the patient. A lens wash and insufflation port includes an integrated flush cap 456 that directs water across the lens of an image sensor and delivers an insufflation gas to expand the lumen in which the endoscope is inserted. Offset from the longitudinal axis of the endoscope is a lens port 458 that is surrounded by a pair of windows or lenses 460 and 462 that cover the illumination sources.

As best shown in FIG. 6C, the imaging assembly includes the distal cap 450, a cylindrically shaped lens assembly 470, and a heat exchanger 480. The heat exchanger 480 comprises a semi-circular section having a concave recess 482 into which the cylindrically shaped lens assembly 470 can be fitted. The concave recess 482 holds the position of the lens assembly 470 in directions perpendicular to the longitudinal axis of endoscope, thereby only permitting the lens assembly 470 to move along the longitudinal axis of the endoscope. Once the lens assembly is positioned such that it is focused on an image sensor 490 that is secured to a rear surface of the heat exchanger 480, the lens assembly is fixed in the heat exchanger with an adhesive; this may be facilitated by the application of precise stops or lands in the molded part design. A pair of LEDs 484, 486 are bonded to a circuit board which is affixed in the heat exchanger such that a channel is formed behind the circuit board for the passage of a fluid or gas to cool the LEDs. A circuit board or flex circuit 492 containing circuitry to transmit and receive signals to and from the control unit is secured behind the image sensor 490 and to the rear surface of the heat exchanger 480. With the lens assembly 470, the LEDs 484, 486, the image sensor 490, and associated circuitry 492 secured in the heat exchanger 480, the heat exchanger assembly can be fitted within the distal cap 450 to complete the imaging assembly as shown in FIG. 6D.

Figure 6E:
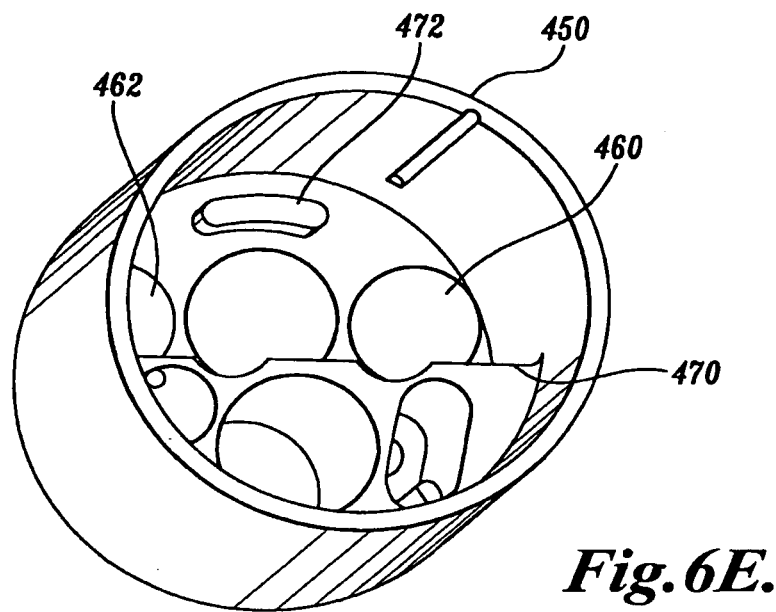

FIG. 6E is a rear isometric view of the distal cap 450. The distal cap 450 is preferably precision molded out of ABS or other bio-compatible material. As indicated above, the front face of the distal cap 450 includes an integrated flush cap 456 and pair of windows 460 that are positioned in front of the LEDs. Preferably, the windows are made of a clear plastic material such as polycarbonate, which are overmolded with the remainder of the distal cap 450. Also within the inside of distal cap 450 is a flat surface 470 that extends proximally, thereby dividing the cylindrical inner surface of the distal cap into a semicircular tube into which the semicircular heat exchanger 480 assembly can be fitted. A protrusion 472 extends from the inside front face of the distal cap 450 and is aligned with a front face of the heat exchanger 480 to limit the extent to which the heat exchanger 480 can be inserted into the distal cap 450.

Figure 6F:
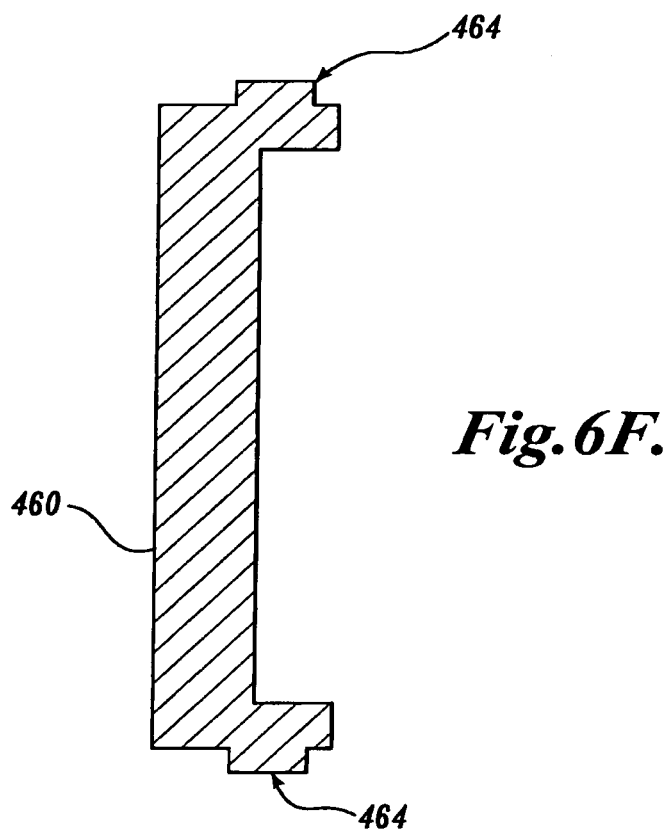

FIG. 6F is a cross-sectional view of the windows 460, 462 that are positioned in front of the LEDs. The windows 460 are preferably molded of an optically clear plastic material with an outwardly extending flange 464 that secures the window 460 in front face of the distal cap 450. Once the windows have been molded, the distal cap 450 can be molded over the windows 460, 462 in order to secure them in place.

Figure 6G:
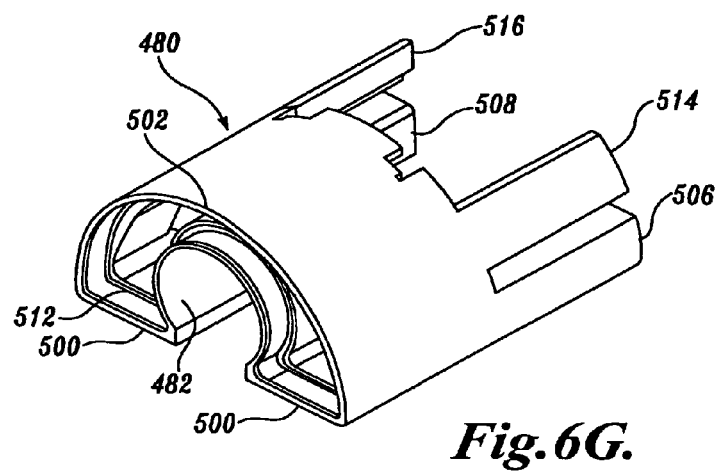

FIG. 6G is a front isometric view of the heat exchanger 480 portion of the imaging assembly. As indicated above, the heat exchanger is a semicircular section having a relatively flat bottom surface 500 that mates with the flat surface 470 in the inside of distal cap 450 and a rounded upper surface 502. The interior of the heat exchanger is generally hollow to form a channel through which a cooling liquid or gas can be passed to remove excess heat from the illumination LEDs. The concave recess 482 is formed in the bottom flat surface 500 of the heat exchanger to receive the cylindrically shaped lens assembly 470, as shown in FIG. 6C. Extending rearwardly from the heat exchanger 480 are a pair of legs 506, 508 having holes therein that are fluidly connected to the interior of the heat exchanger 480. A lip 512 extends around the inside surface of the front face of the heat exchanger 480 to form a bonding surface on which a correspondingly shaped circuit board can be fitted and adhesively secured. In some embodiments of the invention, the heat exchanger 480 may further include additional rearwardly extending fins 514, 516 that positioned over the legs 506, 508 such that a slot is formed therebetween for securing a circuit board or other components to the heat exchanger. However, in some embodiments, the fins 514, 516 may be omitted.

Figure 6H:
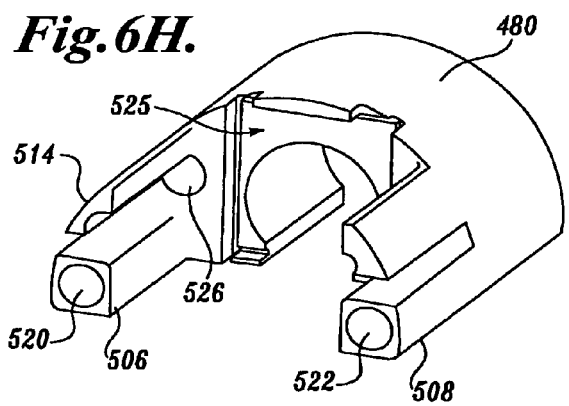

FIG. 6H is a rear isometric view of the heat exchanger 480. As indicated above, each of the legs 506, 508 include a lumen 520, 522 into which a tube can be fitted and through which cooling liquid or gas can be passed such that the liquid or gas flows within the hollow semicircular channel section of the heat exchanger. In addition, the heat exchanger 480 may include a recess 526 for a thermistor or other temperature-sensing device that can transmit signals indicative of the temperature of the distal tip and signal to a processor in the control unit. Alternatively, the temperature sensor could be located in the body of the distal tip.

Figure 6I:
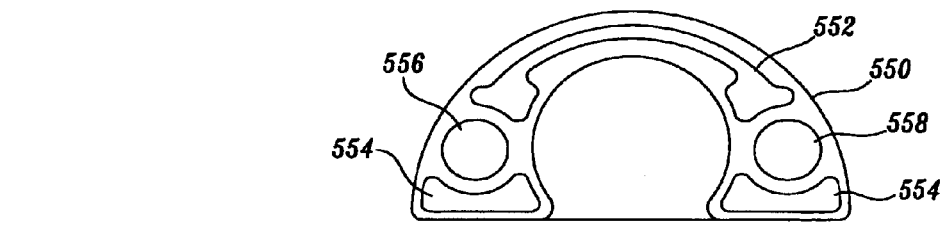

FIG. 6I illustrates a semicircular circuit board 550 that is designed to fit within the front face of the heat exchanger 480. Specifically, the circuit board 550 is adhesively secured in the front face of the heat exchanger 480 against the inner lip 512, as shown in FIG. 6G. The circuit board comprises a base material that is thermally conductive, such as a polymer, metal or ceramic or combination thereof, an electrically isolating dielectric material and a circuit layer. The circuit board 550 includes one or more traces 552 and bonding pads 554 that are used to deliver electrical current to a pair of LEDs that are located on thermally conductive pads 556, 558 that are positioned on either side of the concave recess 482 in which the lens assembly 470 is fitted when the circuit board is installed in the heat exchanger 480.

In one embodiment of the invention, the base material is copper with conductive pads 556, 558 also made of copper. The LEDs are wire bonded to the bonding pads 554, and trace 552. The rear surface of the circuit board 550 is preferably coated with a heat conductive, non-reactive biocompatible material such as gold that is directly exposed to a cooling liquid or gas which is pumped through the heat exchanger via the legs 506, 508.

In one embodiment of the invention, the LEDs 484, 486 are preferably large area die, high power, blue light LEDs coated with a phosphor material that together produce approximately 60 lumens of light. Although the embodiment shows two LEDs positioned on either side of the lens assembly 470, it will be appreciated that fewer or more LEDs could be used and corresponding changes made to the shape of the windows 460, 462 positioned in front of the LEDs.

As an alternative, the inside surface of the windows 460, 462 can be coated with a phosphor coating that produces a white light when exposed to the blue light that is produced by the LEDs. The particular phosphor or phosphor combinations selected may depend on the spectral characteristics of the LEDs employed. The phosphor or phosphors can be mixed with an epoxy adhesive that is applied to the rear surface of the windows 460, 462 and cured by exposing the distal tip 450 to an ultraviolet light source. Mixing the phosphor coating in an adhesive promotes a uniform distribution of the phosphor and is easy to manufacture. Alternatively, the phosphor could be imbibed or directly mixed into the window polymer.

An embodiment of a lens assembly 470 comprises a four-element plastic lens assembly containing several aspheric surfaces to control the image sharpness and distortion image that provide 140° field of view with nominal f-theta distortion and an f/8 aperture. The individual lenses and aperture of the lens assembly are contained in a plastic cylinder for insertion into the cylindrically shaped hole of the heat exchanger 480. The front surface of the lens assembly is adhesively sealed to the lens port 458 in the cap 450.

As indicated, for colonoscopic applications, a diagonal full-field of view of 140 degrees with acceptable f-theta distortion is preferable. Image sharpness should be consistent with FDA Guidance Documents for Endoscopes that suggests resolution of 5 line pairs per millimeter on an object surface, concentric with the entrance pupil, at an object distance of approximately 10 mm. This is consistent with the use of a VGA (640×480) pixel color imager such as those manufactured using CMOS or CCD technology by companies such as Micron, Inc. or ST Microelectronics.

The output of the imager chip is preferably of serial digital format to provide for a reduced wire count to bring the signal from the distal tip to the proximal connector. The cable connecting the proximal end to the distal tip contains power, ground, clock, differential signal, and control signal lines. Typically, 10-14 wires are required. By incorporating the serializer into the imager, a highly compact distal tip can be fabricated. Also, the cost of an imager with an integral serializer is less than the cost of a separate imager and serializer and their interconnects. Additionally, by removing the clock from the distal tip and locating the clock on the imaging electronics subsystem (60), further reduction of the size of the distal tip is possible with associated reduction of the cost of the endoscope.

For an imager with a diagonal format size of approximately 4.5 mm, the focal length of the lens is 1.8 mm in order to cover a full field of 140 degrees.

Figure 6J:
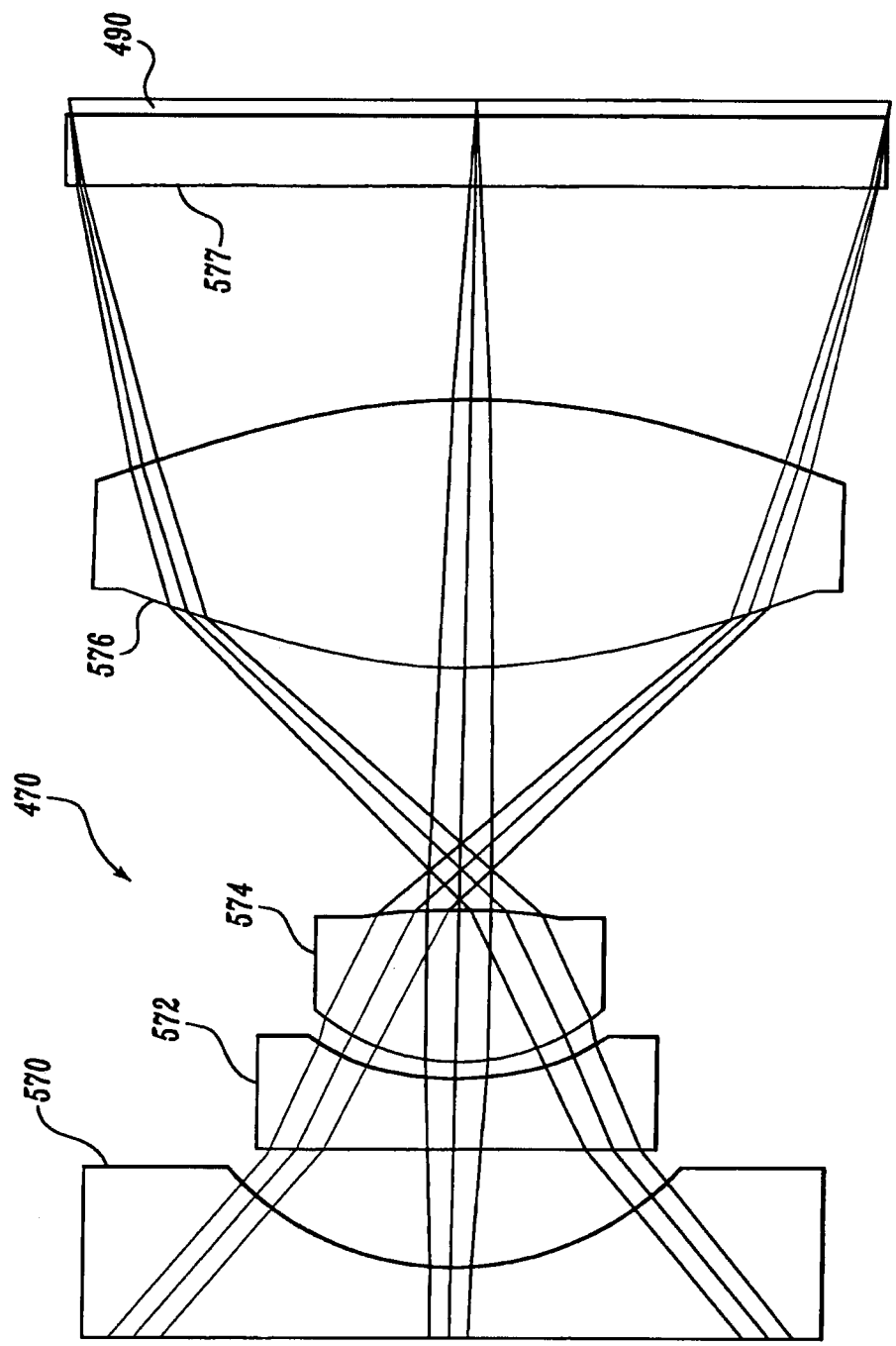
FIG. 6J illustrates a lens assembly for use with an embodiment of the present invention.

The four element plastic lens assembly 470 is depicted in FIG. 6J, along with ray traces from ½ of the field. Elements 570, 572, and 576 are injection molded from identical plastic such as a crown-like material Ticona Topas. Element 574 is injection molded from polystyrene. To achieve the required correction, the concave surfaces of elements 570 and 572 are rotational aspherics and both convex surfaces of element 576 are aspheric. The F/# of the lens is approximately 8, to provide a sufficient depth of field. The right most optical element 577 is a protective coverglass that is incorporated into the imager sensor 490.

In a preferred embodiment of the invention, the image sensor 490 comprises a VGA CMOS image sensor with 640× 480 active pixels and an on-chip serializer that transmits image data to the control cabinet in a serial form. Such a CMOS image sensor is available as Model No. MI-370 from Micron Electronics of Boise, Id. In order to transmit serial image data and control signals along the length of the endoscope, the data and control signals are preferably sent digitally using a low voltage differential signal (LVDS) protocol along a suitable twisted micro coaxial cable.

To construct the image assembly, the distal cap 450, including flushing port 456 is molded of ABS plastic over the LED windows 460, 462. The circuit board 550, having LEDs 484, 486 bonded thereto, is secured within the heat exchanger 480 and the CMOS sensor 490 and associated electronics 492 are secured to the rear surface 525 of the heat exchanger 480 between the legs 506, 508. The lens assembly 470 is inserted into the concave recess 482 and adjusted longitudinally until it is at the optimum position to focus light on the image sensor 490 before being cemented in place. The completed heat exchanger assembly can then be inserted into the distal tip 450 and adhesively bonded to complete the imaging assembly. The remaining tubes for the low pressure lavage bolus wash channel 454, lens wash and insufflation channel and working channel are then secured to corresponding lumens in the distal tip in order to complete the distal imaging section of the endoscope.

Variations on the components, dimensions and configuration of the components in the optical assembly are contemplated, which may depend in part on the desired performance characteristics of the endoscope. For example, issues like field of view, levels of illumination, operating temperature of the distal tip etc. affect the balance and tradeoff of a particular configuration. For example, it may be desirable to add a focusing capability to the endoscope by moving the cylindrically shaped lens assembly relative to the image sensor. If the lens assembly can be focused, a lower F# (i.e., faster) lens can be used thereby decreasing the amount of light required. If less light is required, the need for an active cooling mechanism to remove any excess heat from the illumination source is reduced or eliminated. Alternatively, it may be possible to replace the water-cooled heat exchanger with a heat pipe that is thermally coupled to the illumination sources or to fill the voids of the endoscope with a thermally conductive fluid or other substance.

Because the distance over which the lens assembly must be moved with respect to the image sensor (or vice versa) is relatively small (e.g., a few hundred microns), a focusing mechanism can be constructed of simple mechanical or electrically activated components such as magnetic, thermally activated bi-metallic components, screw-type advancers, etc. Furthermore, if the lens assembly is contained in a cylindrical recess 482 of the type shown in FIG. 6C or an equivalent structure, the focusing may be simplified because the lens assembly is constrained to be in-line with the image sensor.

Figure 7:
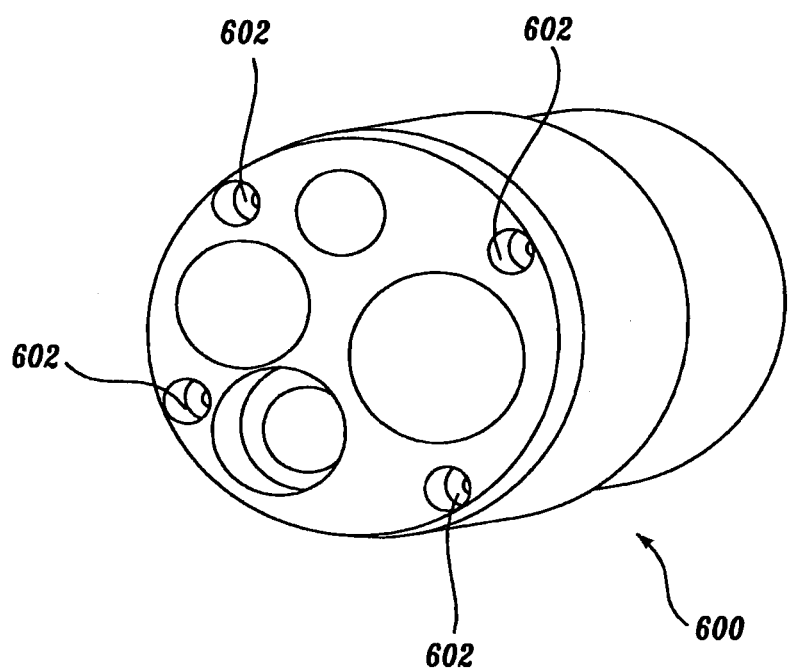
FIG. 7 illustrates one mechanism for terminating a number of control cables in a distal tip of an endoscope in accordance with an embodiment of the present invention.

FIG. 7 shows further detail of an embodiment of a distal tip 600 of the endoscope that is similar to that shown in FIG. 6A. In this embodiment, the tip section 600 includes a number of counter bored holes 602 that are positioned around the outer circumference of the distal tip 600. The counter bored holes 602 receive swaged or flanged ends of the control cables (not shown) that orient the distal tip. Tension on the control cables pull the distal tip 600 in the direction of the tensioning force.

FIG. 8 is a lengthwise, cross-sectional view of an endoscope 650 in accordance with one embodiment of the present invention. A distal tip 652 is adhesively secured, welded or otherwise bonded within a center lumen at the distal end of an articulation joint 654. Secured to the proximal end of the articulation joint 654 is a distal end of a shaft 656. As discussed above, the shaft 656 is preferably stiffer or of greater torsional stiffness or is better able to transmit torque towards the distal end of the endoscope than at the proximal end of the endoscope.

The control cables 658 that move the distal tip of the endoscope are preferably made of a non-stretching material such as stainless steel or a highly oriented polyethyleneterephthalate (PET) thread string. The control cables 658 may be routed within a center lumen of the shaft 656 or, as shown in FIG. 8, may be routed through lumens formed within the walls of the shaft 656. The control cables 658 extend through guides within the walls of articulation joint 654 and terminate either at the distal end of the articulation joint 654 or in the distal tip section 602. In a presently preferred embodiment of the invention, the control cables are Bowden cables (i.e., a system comprising an outer sheath and an inner cable). For example, the Bowden cable could comprise an outer stainless steel jacket having a lubricous liner such as HDPE and/or an inner cable coated with a lubricant such as silicone in order to reduce friction. Alternatively, the cable may comprise other suitable metals or plastics, and other high modulus materials, such as an incompressible plastic or metal that may be used for the sheath. The distal end of the outer jacket is received in the proximal end of the articulation joint 654 while the proximal end of the jacket is secured in the manual controller or the connector that mates the endoscope to the control cabinet.

If the control cables are routed through the center lumen of the shaft 656, the cables are preferably carried in stainless steel or plastic spiral wrapped jackets to prevent binding and a transition guide 670 such as that as shown in FIGS. 9A and 9B may be used to guide the control cables into the proximal end of the articulation joint. The transition guide 670 has a proximal end 672 that is secured within a lumen of the distal end of the shaft. A central body portion 674 of the transition guide 670 has a diameter equal to the outer diameter of the imaging endoscope. In addition, the body portion 674 includes a number of diagonal lumens 678 that extend from a center lumen of the proximal end 672 to an outer surface of a stepped distal end 676 of the transition guide. The distal end 676 is secured within a proximal end of the articulation joint 654. Control cables in the diagonally extending lumens 678 are therefore guided to the outer edge of the catheter where they extend through the guides or control cable lumens of the articulation joint 654.

Figure 10A:
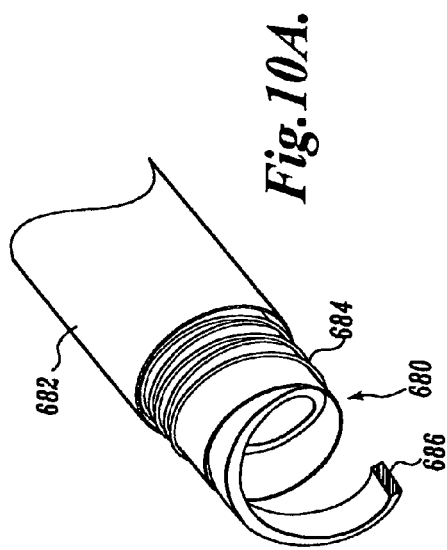
FIGS. 10A and 10B illustrate the construction of a shaft portion of an endoscope in accordance with an embodiment of the present invention.
Figure 10B:
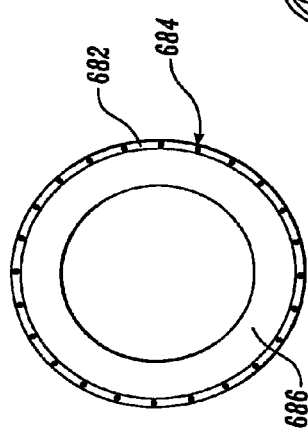

FIGS. 10A and 10B illustrate one embodiment of a shaft that is used to form an endoscope. The shaft 680 has an extruded sleeve 682 that may include a wire or other braid 684 embedded therein. The braid 684, if present, allows the torque characteristics of the shaft to be adjusted. The sleeve 682 may be formed by placing a sleeve over a mandrel. The braid 684 is placed over the sleeve and the mandrel is dipped into or sprayed with a coating material. Preferably the sleeve and coating material are made of pellethane, polyurethane or other materials of established biomedical use such as polyethylene, polypropylene or polyvinyl alcohol. In a currently preferred embodiment, the sleeve 682 is made of black pellethane with an outside diameter of 0.507 inches and an inside diameter of 0.460 inches. A stainless steel braid is embedded therein and has 23 picks per inch. In addition, an inner wrap of aromatic polyester polyurethane tape completes the outer shaft. The exterior of the shaft can be coated with a hydrophilic, lubricious coating such as the HYDROPASS™ hydrophilic coating available from Boston Scientific Corporation, of Natick, Mass., and described in U.S. Pat. Nos. 5,702,754 and 6,048,620, which are herein incorporated by reference.

A plastic spiral wrap 686 such as spiral wire wrap available from Panduit Inc. is inserted into a center lumen of the shaft 680. The spiral wrap 686 prevents the shaft 680 from crushing as it is bent around curves of a patient's anatomy.

In one embodiment of the shaft 680, the spiral wrap has a thickness of 0.060 inches and a pitch of 3/16 inch. The spiral wrap 686 has an outer diameter of 0.500 inches and an inner diameter of 0.380 inches and is twisted into the shaft 680 to form an interference fit. However, it will be appreciated that other thicknesses of spiral wrap with a different pitch could be used to provide the desired column strength and bend modulus as well as to prevent kinking.

A metal braid is placed over the articulation joint. The braid has several functions including provides torsional strength to the articulation joint, keeps the links of the joint aligned during articulation and prevents the outer cover from being pinched between the links of the joint. The preferred design uses a metal braid but alternatively plastic braids such as PET can be used. The braid properties (such as braid angle, % coverage, # of pics per inch, etc.) can be adjusted to give the required balance between low articulating force and consistent, in-plane articulation. In other embodiments of the design, a variable braid may be used over the articulation joint to control the bending arc of the joint. A tighter braid on the proximal links of the articulation joint encourages the distal links to bend first and so the whole joint bends with a smaller bending arc. The outer plastic cover is fitted over the articulation joint portion of the shaft to prevent contaminants from entering the shaft through gaps in the braided articulation joint.

As indicated above, the proximal section of the endoscope shaft is preferably more flexible than the distal section. The proximal portion of the shaft is preferably made of a corrugated polyethylene tubing such as Model No. CLTS 50E-C available from Panduit Inc.

Figure 11:
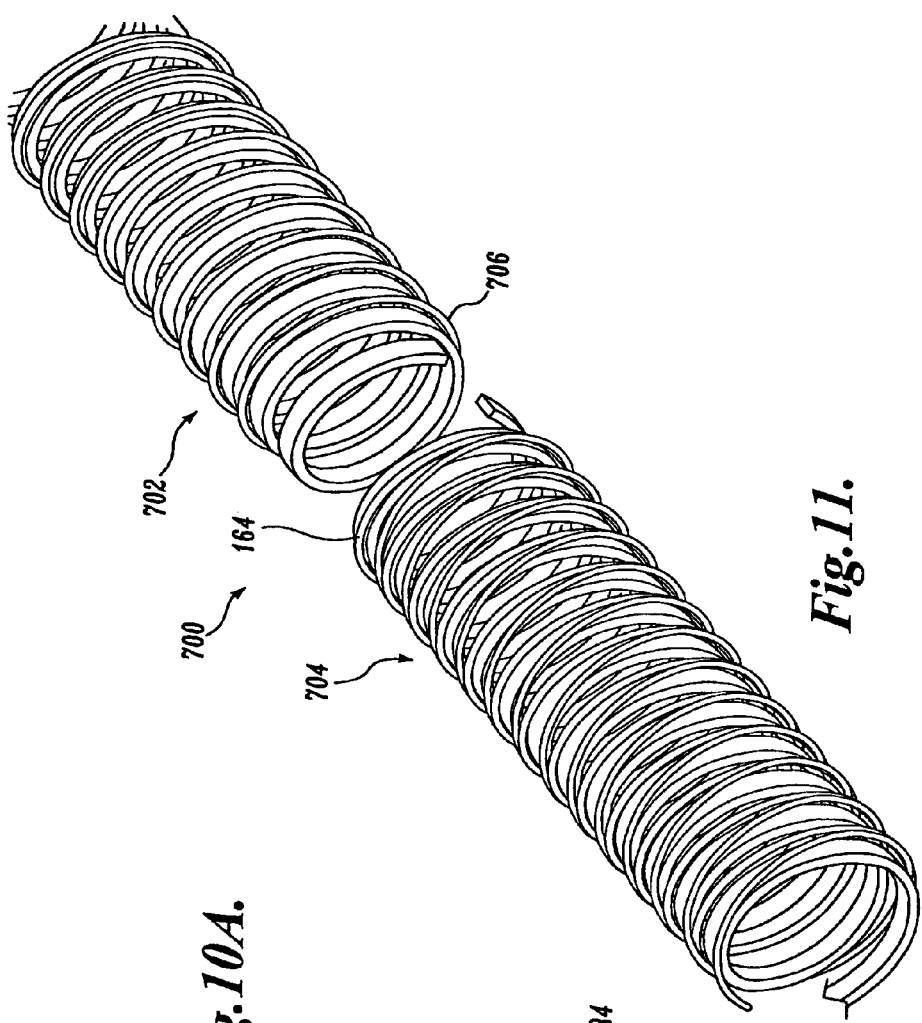
FIG. 11 illustrates one mechanism for providing a shaft with a varying stiffness along its length in accordance with an embodiment of the present invention.

FIG. 11 shows one method of altering the torque fidelity of the distal portion of the shaft. A shaft 700 has a flexible section 702 that is toward the distal end of the endoscope break out box and a stiffer section 704 that is more proximal to the break out box (not shown). The portion of the endoscope that is more distal has an increasing flexibility toward the distal tip and conversely a higher torque fidelity and column strength proximally. To increase the torque fidelity characteristics of the distal section 704 of the shaft, a braid 706 in that section includes two or more braid or wire strands that are wound in opposite directions. In one embodiment, the wire braid has a pitch of 14-16 pics. However, the number of strands and their spacing can be adjusted as needed in order to tailor the torque fidelity of the shaft.

The more distal end 702 of the shaft 700 has a single spiral of wire 706 that is preferably wound in the same direction as the plastic spiral wrap in the center lumen of the shaft 700. Again, the torque fidelity of the proximal end of the shaft 702 can be varied by adjusting the pitch and/or direction of the wire 706 and its flexibility.

As will be appreciated, the single wire spiral 706 provides some torque fidelity but does have the same torque fidelity as the dual wire braid in the distal section of the shaft in order to allow easy manipulation for, e.g., resolution of loops. The single wire spiral 706 may be omitted from the distal portion of the shaft if even less torque fidelity is desired.

Figure 12A:
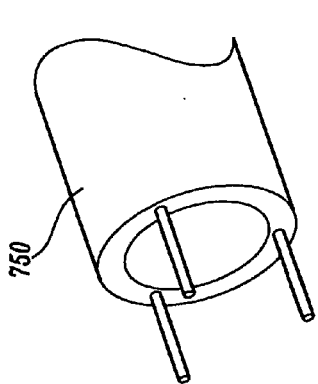
FIGS. 12A and 12B illustrate an extrusion used to make an articulation joint in accordance with an embodiment of the present invention.
Figure 12B:
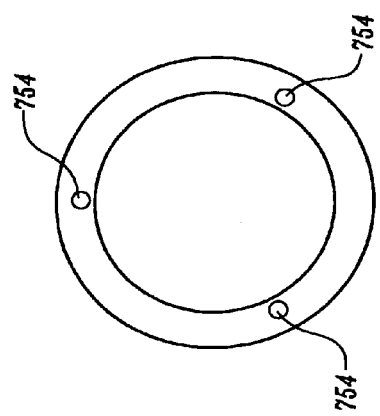

As discussed above, in order to facilitate steering the distal tip of imaging endoscope, the endoscope includes an articulation joint that allows the distal tip to be turned back on itself, i.e., over an arc of 180 degrees, by the control cables and can be directed to make that bend in any direction desired about the circumference of the distal tip. That is, the operator can select both the amount of the bend or articulation and the direction of the bend. As shown in FIGS. 12A and 12B, an articulation joint 750 in accordance with one embodiment of the invention is formed from a cylinder of a plastically deformable material having a central lumen 752, and a number of control cable lumens 754 located in the walls of the articulation joint. If desired, the space between the control cable lumens in the cylinder wall may be thinner such that the control cable lumens form bosses that extend into the central lumen of the cylinder. The control cable lumens 754 are preferably oriented at 120° apart if three control cables are used or 90° apart if four control cables are used.

Figure 13:
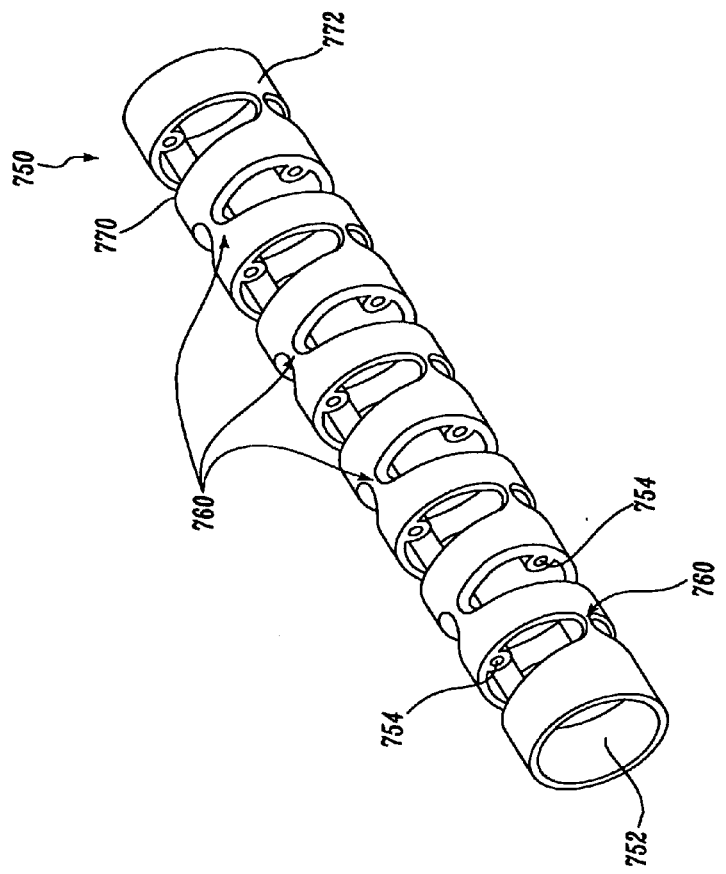
FIG. 13 illustrates an articulation joint in accordance with an embodiment of the present invention.

To facilitate bending of the articulation joint, the cylinder includes a number of living hinges 760 formed along its length. As can be seen in FIG. 13, each living hinge 760 comprises a pair of opposing V-shaped cuts 770 on either side of the cylinder and are separated by a flexible web 772 that forms the bendable portion of the hinge. In the embodiment designed for four control cables, each pair of living hinges along the length of the joint is oriented at 90 degrees with respect to an adjacent hinge.

Upon tensioning of a control cable, those living hinges having webs 772 that are in line with the retracting control cable do not bend. Those living hinges having webs that are not in line with the control cable will be closed, thereby bending the articulation joint in the direction of the control cable under tension.

Another advantage of the articulation joint 750 shown in FIG. 13 is that the distal end of the endoscope can be retracted by pulling all the control cables simultaneously. This allows the physician to maneuver the distal tip in the body, e.g., to "square off" on a lesion, without having to move the remaining length of the endoscope. This may be useful when performing surgical procedures such as obtaining a biopsy or snaring polyps.

The articulation joint can be formed by extruding a cylinder with the central and control cable lumens in place and cutting the cylinder tube with a knife, laser, milling tool, water jet, or other material removal mechanism to form the living hinges. Alternatively, the articulation joint can be molded with the living hinge joints in place. As will be appreciated, the angles of the V-shaped cuts that form the hinges may be uniform or may vary along the length of the articulation joint. Similarly, the distance between adjacent living hinges may be uniform or may vary in order to tailor the bending and torque fidelity characteristics of the articulation joint. In one embodiment of the invention, each living hinge 760 has a closing angle of 30° so that six hinges are required to provide 180° of movement. The distal end of the articulation joint 750 may be counter-bored to receive the distal tip section of the endoscope, as discussed above. Similarly, the proximal end of the articulation joint 750 is adapted to receive the distal end of the shaft section of the endoscope. In the embodiment shown in FIG. 13, the control cable lumens 754 are aligned with the widest spacing of the live hinges and with the web portion of each hinge. However, it may be desirable to offset the control cable lumens 754 with respect to the hinges in order to lessen potential binding of the control cables in the hinge. As indicated above, the articulation joint should be made of a biocompatible material accepted for medical use that will bend but will not collapse. Suitable materials include polyurethane, polyethylene, polypropylene, or other biocompatible polymers.

To prevent wear by the control cables as they are pulled by the actuation mechanism in the control cabinet, it may be desirable to produce the articulation joint from a material having areas of different durometers. As shown in FIGS. 14 and 15, a cylinder formed from an extruded tube 780 has alternating bands of a high durometer material 782 and a lower durometer material 784 around its circumference. The lumens 786 used to route the control cables are formed in the high durometer material 782 to resist abrasion as the control cables are tensioned and released and traverse along the lumen. In addition, the high durometer material also reduces friction between the control cables and the surrounding lumen. FIG. 15 illustrates an articulation joint where the control cable lumens are offset with respect to the orientation of the web portions of the live hinges so that the control cables do not pass through the web portion 772 of the hinge.

Figure 16A:
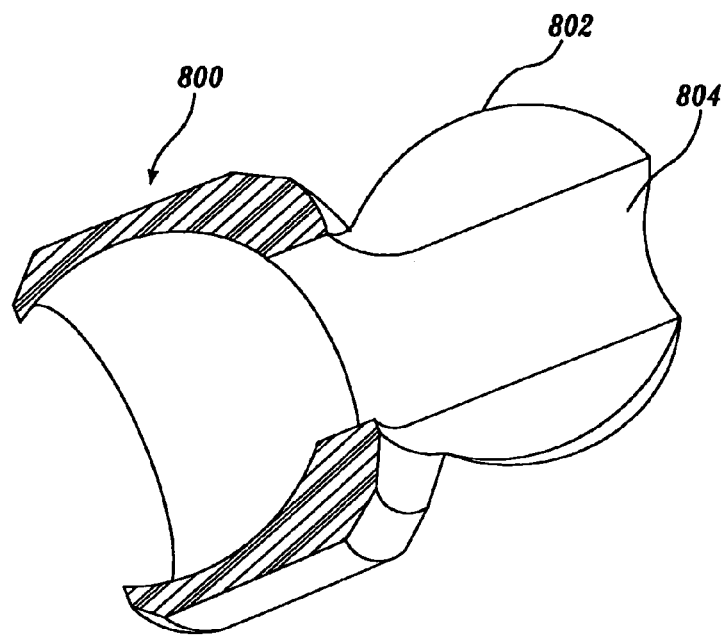
FIGS. 16A and 16B illustrate another embodiment of an articulation joint according to an embodiment of the invention including a number of ball and socket sections.
Figure 16B:
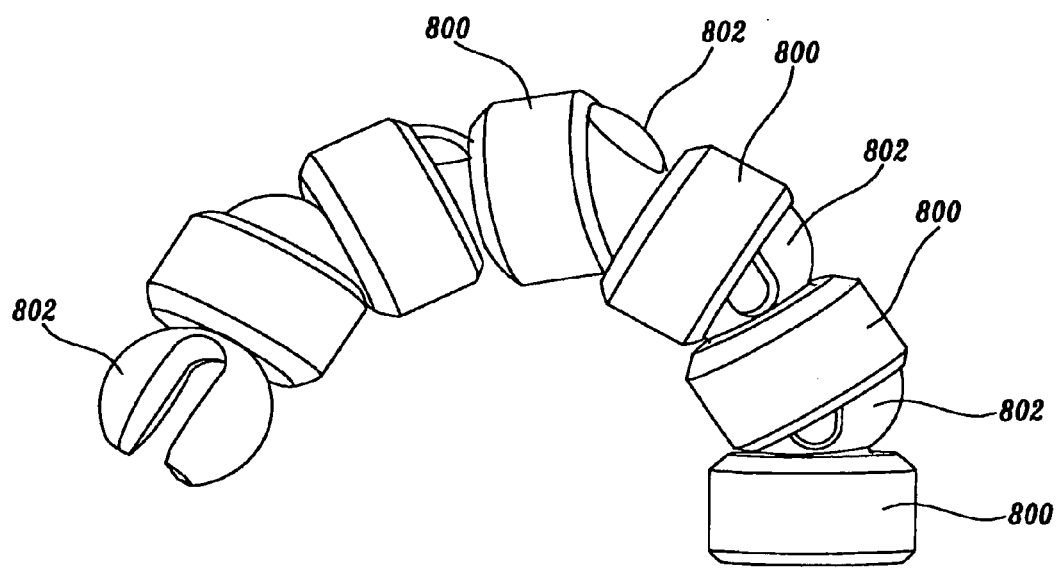

FIGS. 16A and 16B illustrate an alternative embodiment of an articulation joint. In this embodiment, the joint comprises a series of ball and socket connectors that are linked together. As shown in FIG. 16A, each connector includes a socket section 800 and a ball section 802. The ball section 802 fits in a socket section 800 of an adjacent connector. A lumen extends axially through the ball section 802 to allow for passage of the wires that connect to the light source and the image sensor and tubes that carry irrigation fluids and insufflation gases. The ball and socket sections are preferably molded of a biocompatible polymer.

Figure 17A:
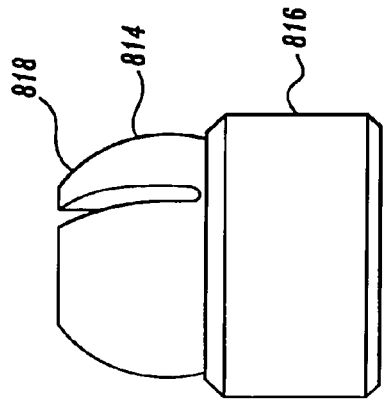
FIGS. 17A-17D illustrate various possible configurations of ball and socket sections used to construct an articulation joint.
Figure 17B:
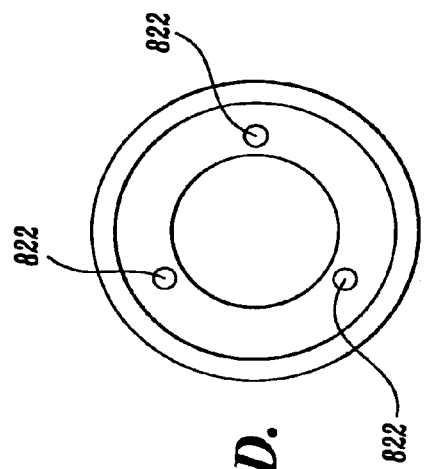
Figure 17C:
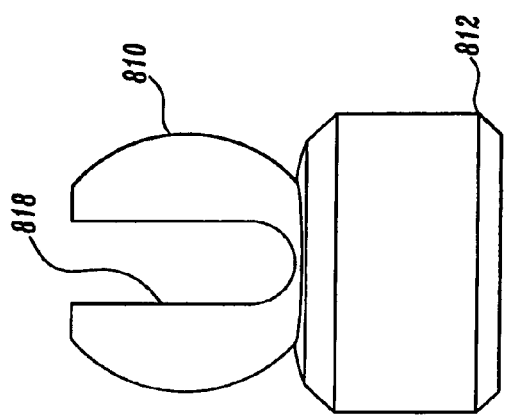
Figure 17D:
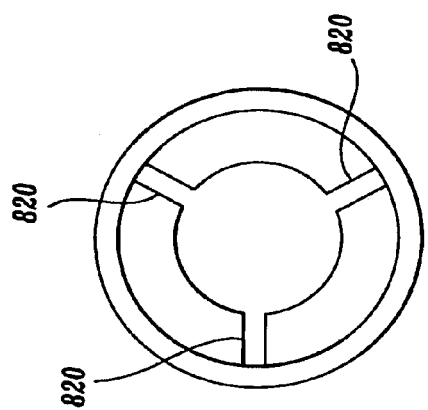

Each socket section can be formed with a fully formed ball section such as ball section 810 on a socket 812 shown in FIG. 17A. Alternatively, a partial ball section such as ball section 814 can be formed on a socket section 816 as shown in FIG. 17B. To provide room for the control cables to move, the ball section can include slot 818 as shown in FIGS. 17A, 17B that cuts through the middle and sides of the ball section. Alternatively, a number of smaller slots 820 can be positioned around the circumference of the ball section as shown in FIGS. 17C and 17D. The slots allow the control cables to be shortened under tension. A number of holes 822 at the interface of the ball section and socket section allows passage of the control cables from the socket section into the ball section as shown in FIG. 17D.

In another embodiment of an articulation joint, the articulation joint is made of a series of stacked discs that are positioned adjacent one another and move with respect to each other. As shown in FIG. 18A, a disc 850 comprises an annular ring 852 having a pair of rearward facing rocker surfaces or cams 854 and a pair of forward facing rocker surfaces or cams 856. The cams 854 are positioned 180° apart on the rear surface of the annular ring 852, while the forward facing cams 856 are positioned 180 degrees apart on the forward face of the annular ring 852. In the embodiment shown, the forward cams 856 are oriented at 90° with respect to the rear cams 854. Opposite each cam on the other side of the annular ring is a flat land section so that the cams of an adjacent disc may engage with and rock on the flat section. Holes 860 are drilled through the annular ring and through the cams for passage of the control cables. Upon tension of the control cables, the discs will rock on the surface of the cams 854, 856 thereby bending the articulation joint in the desired direction.

FIG. 18B shows an articulation joint made up of a series of stacked discs 850a, 850b, 850c . . . engaged with one another to form an articulation joint. A number of control cables 870a, 870b, 870c, 870d, pass through the discs and are used to pull the discs on the cam surfaces to move the joint in the desired direction.

FIGS. 19A and 19B show an alternative embodiment of the articulation joint shown in FIGS. 18A and 18B. In this embodiment, an articulation joint comprises a series of stacked discs 880, 880a, 880b, 880c, each comprising an annular ring having a pair of concave pockets 882 on its rear surface and a pair of correspondingly shaped convex cams 884 on its front surface. The concave pockets 882 are oriented at 90° with respect to the convex cams 884 so that adjacent discs may be stacked such that the cams of a disc fit within the pockets of the adjacent disc. The corresponding shaped cams 884 and pockets 882 help prevent the discs from rotating with respect to one another. Holes or lumens 886 are formed through the annular ring 880 for passage of a number of control cables 890a, 890b, 890c, 890d, as shown in FIG. 19B. The holes or lumens 886 may be positioned at the center of the cams and pockets. However, the holes for the control cables may be offset from the position of the cams and pockets, if desired. Preferably discs 880 are molded from a biocompatible polymer having a relatively slick surface, such as polyurethane, polypropylene, or polyethylene, which reduces friction between adjacent cams and pockets.

Figure 20A:
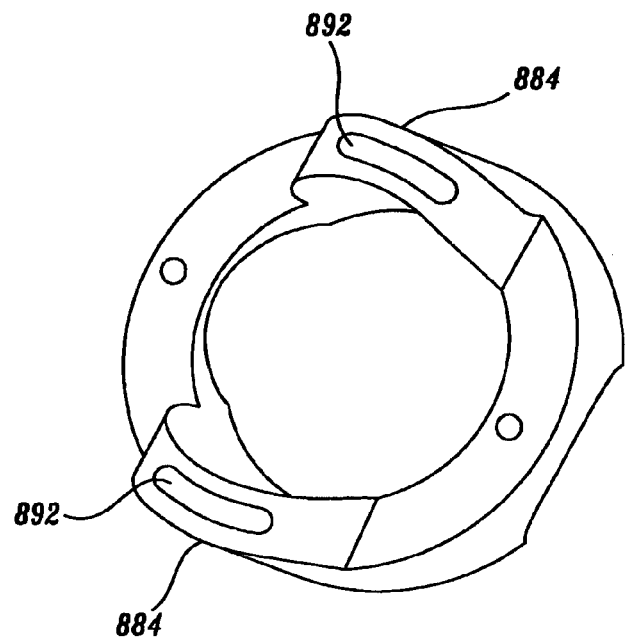
FIGS. 20A-20B illustrate a disc used to form an articulation joint in accordance with another embodiment of the present invention.
Figure 20B:
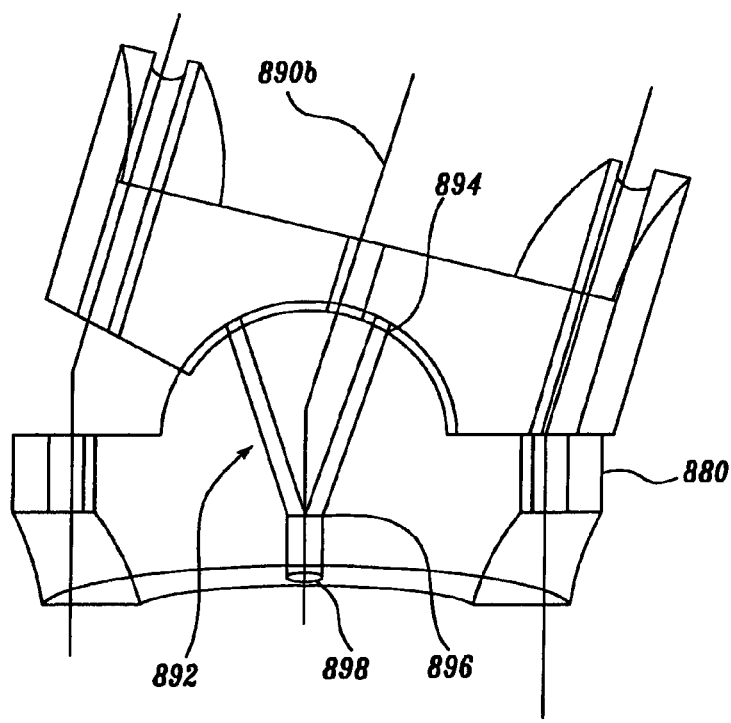

FIGS. 20A and 20B show yet another alternative embodiment of an articulation joint. In this embodiment, the articulation joint is formed of a stack of discs, each of which comprises an annular ring. The annular ring has forwardly extending cams having an arcuate slot 892 molded therein that allows a control cable to move more freely in the cam as the disc is moved relative to an adjacent disc. As best shown in FIG. 20B, the slot 892 tapers from a widest point 894 at the outer edge of the cam to a narrow point 896 where the slot forms a cylindrical hole 898 that extends to the opposite edge of the annular ring 880. A control wire 890b is free to bend within the widened portion of the arcuate slot 892 as an adjacent disc is rotated.

Figure 21B:
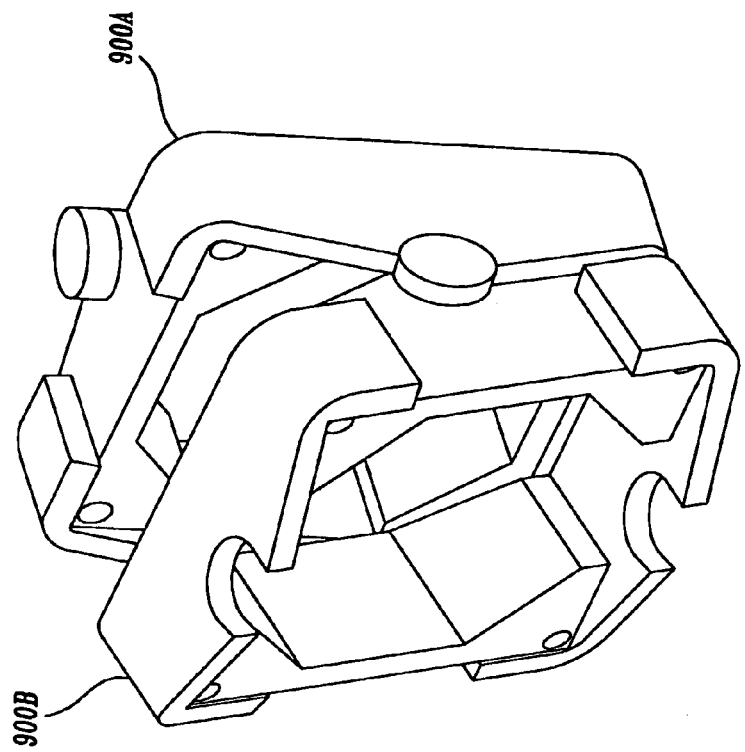
FIGS. 21A-21B illustrate a non-circular segment used to form an articulation joint in accordance with another embodiment of the present invention.
Figure 21A:
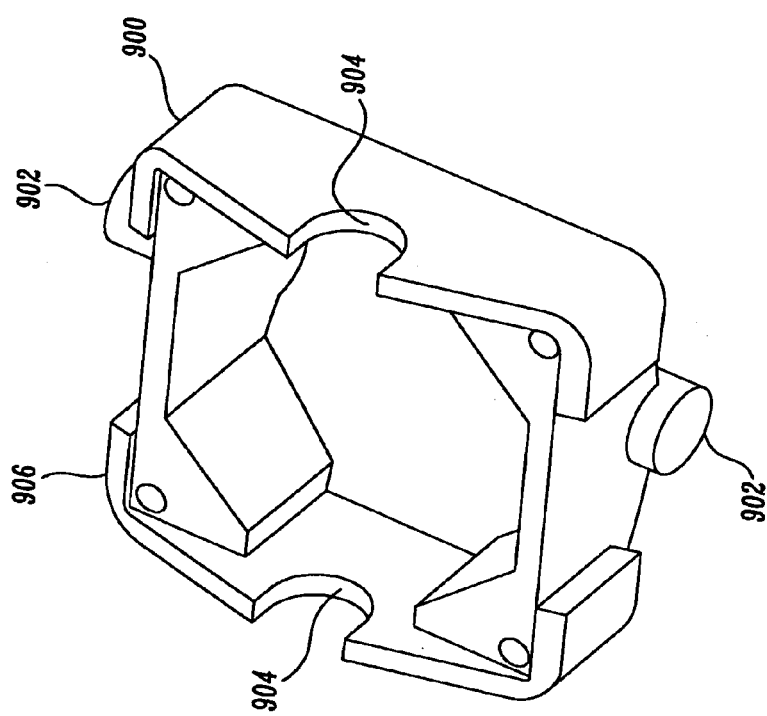

Although the discs of the articulation joints shown in FIGS. 18-20 are generally circular in shape, it will be appreciated that other shapes could be used. FIGS. 21A and 21B show an articulation joint formed from a number of sections having a generally square outer shape. As shown in FIG. 21A, a section 900 is a square band having a pair of pins 902 that extend outwardly on opposite sides of the rear surface of the square section. On the opposite sides of the front surface are a pair of opposing circular recesses 904 that are oriented at 90° to the pins on the rear surface and are sized to receive the round pins 902 of an adjacent section. In the embodiment shown, the control cables are routed through holes or lumens in corner blocks 906 that are found in each corner of the square section 900. FIG. 21B shows two adjacent square sections 900a, 900b secured together. As can be seen, the section 900b can rotate up or down on its pins with respect to the adjacent section 900a. Although circular and square articulation sections have been shown, it will be appreciated that other segment shapes such as triangular or pentagonal, etc., could also be used to form an articulation joint.

In the embodiments of the articulation joints described above each disc or segment that comprises the joint is preferably made of the same material. However, it is possible to vary the material from which the segments are made and/or the physical dimensions or spacing between adjacent segments in order to vary the flexibility and torque fidelity of the joint along its length.

In some environments, a full 180° turning radius of the distal tip of the imaging endoscope may not be necessary. In those environments, an articulation joint made of interconnected discs or segments may be replaced with a flexible member such as a braided stent. FIG. 22 shows an imaging endoscope 925 having a braided stent 930 as the articulation joint. The braided stent 930 extends between a distal tip and a connector 934 that joins the proximal end of the stent 930 with the distal end of a flexible shaft 936. A cover 938 extends over the flexible shaft 936 and the braided stent 930. Control cables (not shown) extend through a lumen of flexible shaft 936 and are used to pull the stent 930 such that the distal tip is oriented in the desired direction. In addition, pulling all the control cables simultaneously allows the distal tip of the endoscope to be retracted.

FIG. 23 shows one method of securing the distal ends of the control cables to a braided stent 930. The control cables 940a, 940b, 940c, 940d can be woven through the wires of the stent 930 and terminated by forming loops around the wires that comprise the stent. Alternatively, the ends of the cables 940 can be soldered or adhesively secured to the wires of the stent.

Figure 23A:
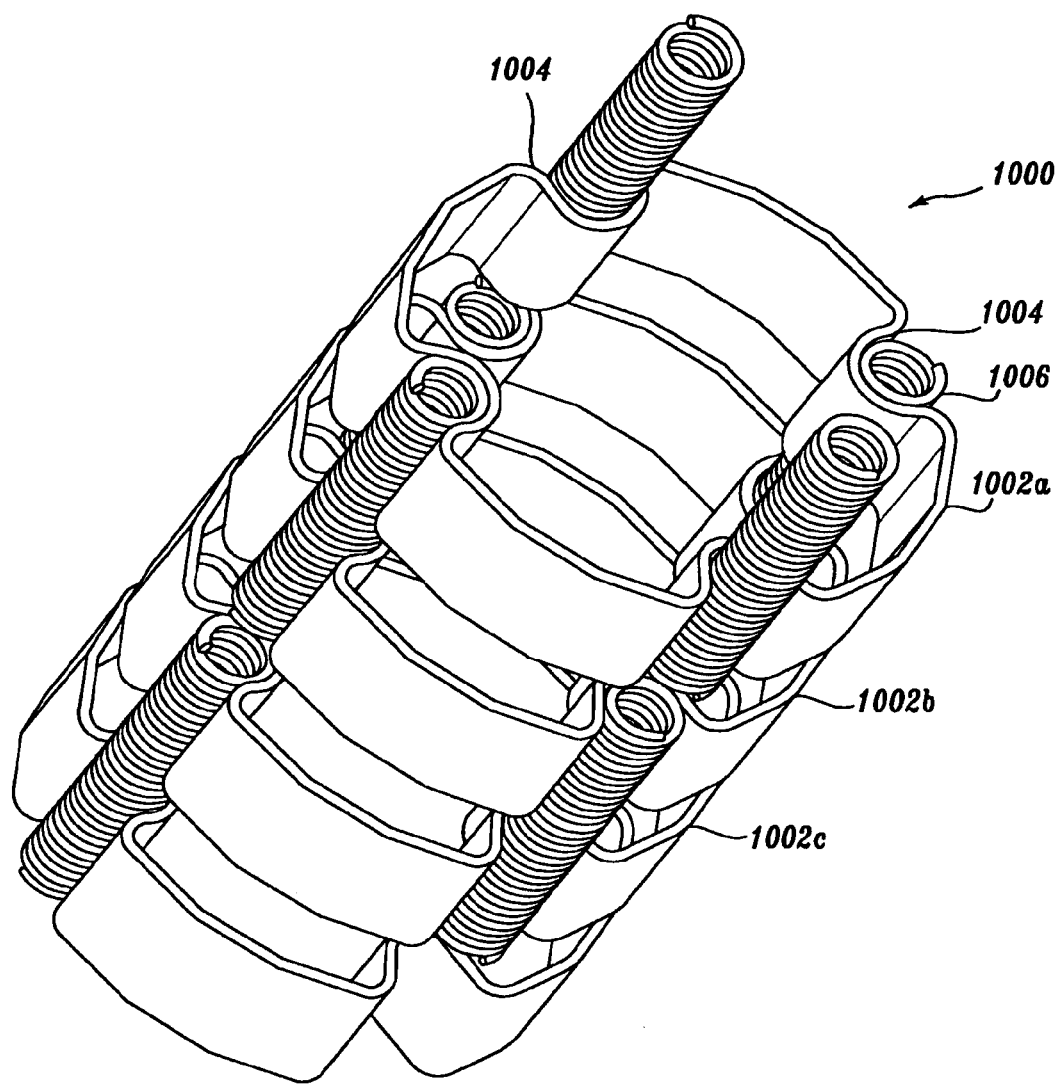
FIGS. 23A-23X illustrate additional embodiments of an articulation joint for use in an endoscope of the present invention.

FIG. 23A shows yet another alternative embodiment of an articulation joint 1000 for use with an endoscope of the present invention. The articulation joint 1000 is made of a series of stacked rings 1002a, 1002b, 1002c, etc. Each ring is preferably formed of a deep-drawn steel or other metal that allows the ring to be stiff while having a thin wall profile in order to maximize the size of the inner lumen. Positioned at equal intervals around the outer circumference of the ring are inwardly extending concave recesses 1004 that receive short spring sections 1006 that are used to join adjacent rings together. Two springs on opposite sides of a ring 1002 are used to join adjacent rings together. For example, if three rings 1002a, 1002b, and 1002c are aligned, the rings 1002a and 1002b are joined together with spring segments located at 0° and 180° on the rings, while ring 1002B is joined to ring 1002e with orthogonally aligned spring segments located at 90° and 270° around the rings. A gap is formed between adjacent rings so that the pair of springs forms a flexible joint that can bend in directions that are the away from the longitudinal axis of the articulation joint but has limited ability to compress the articulation joint in the direction of the longitudinal axis of the articulation joint. Each spring 1006 is secured within the concave recess 1004 of the ring 1002 using an adhesive, crimping, welding, or with other securing mechanism.

The articulation joint 1000 shown in FIG. 23A has the advantage that the control cables pass through the center of the spring segments 1006 and on the outer circumference of the articulation joint, thereby maximizing the amount of room available for passage of tubes and other cables through the center opening of each ring 1002 and minimizing the torque required to bend the articulation joint.

Figure 23B:
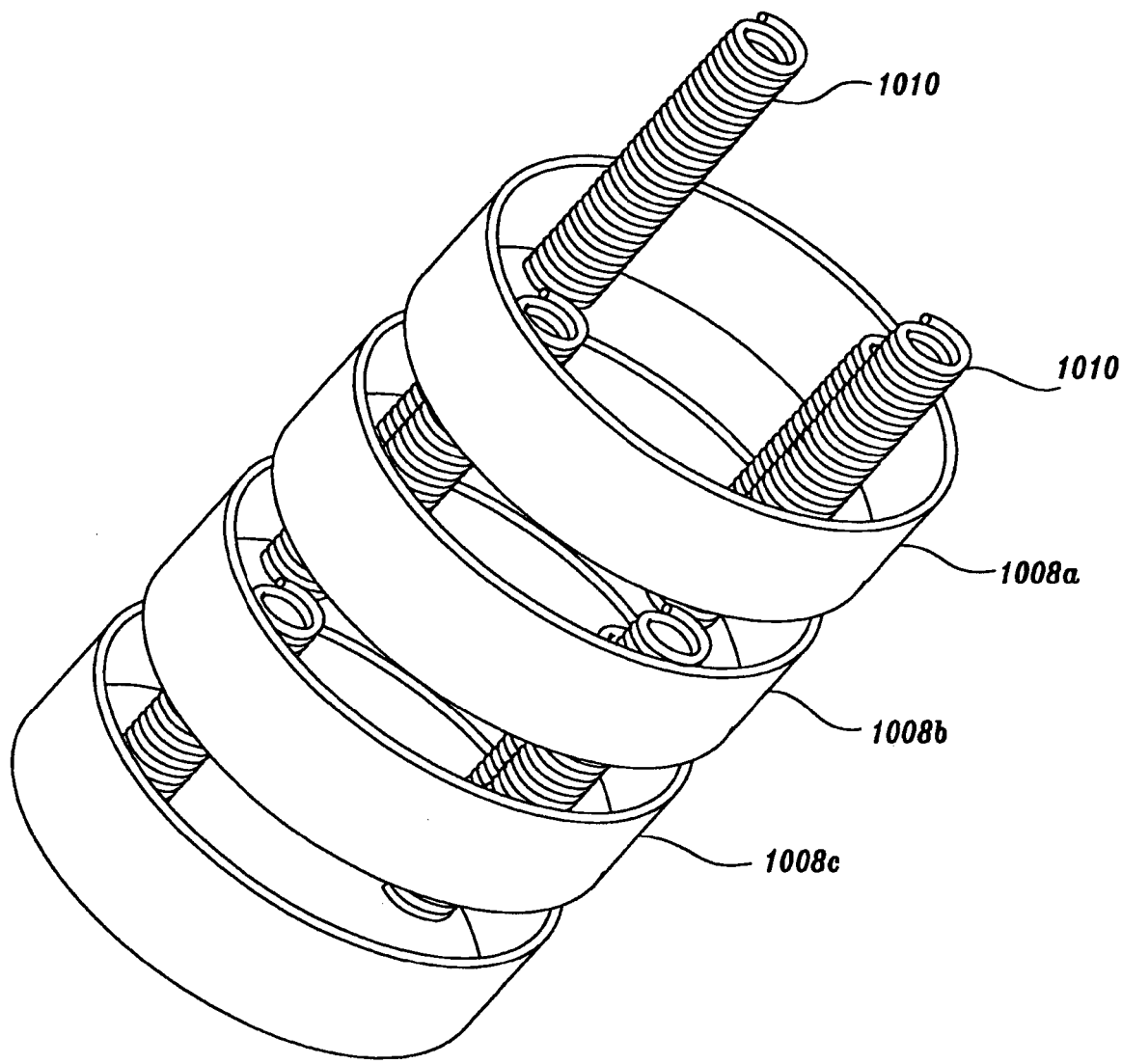
FIG. 23 illustrates one possible technique for securing the ends of a control wire to a braided articulation joint shown in FIG. 22.

FIG. 23B illustrates an alternative embodiment of the articulation joint shown in FIG. 23A. In this embodiment, the articulation joint comprises a number of deep drawn or otherwise formed metal rings 1008a, 1008b, 1008c that are joined together with springs that are located on the inner circumference of each ring. Each ring is connected to an adjacent ring with a pair of spring segments located on opposite sides of the ring. The springs 1010 are secured to the inner circumference of the rings 1008 with an adhesive or by welding, or using other securing means. In the embodiment shown in FIG. 23B, the control cables are routed through the spring segments and are more closely positioned to the longitudinal axis of the articulation joint. Being closer to the longitudinal axis may require more force on a control cable to bend the articulation joint in a desired direction.

Figure 23C:
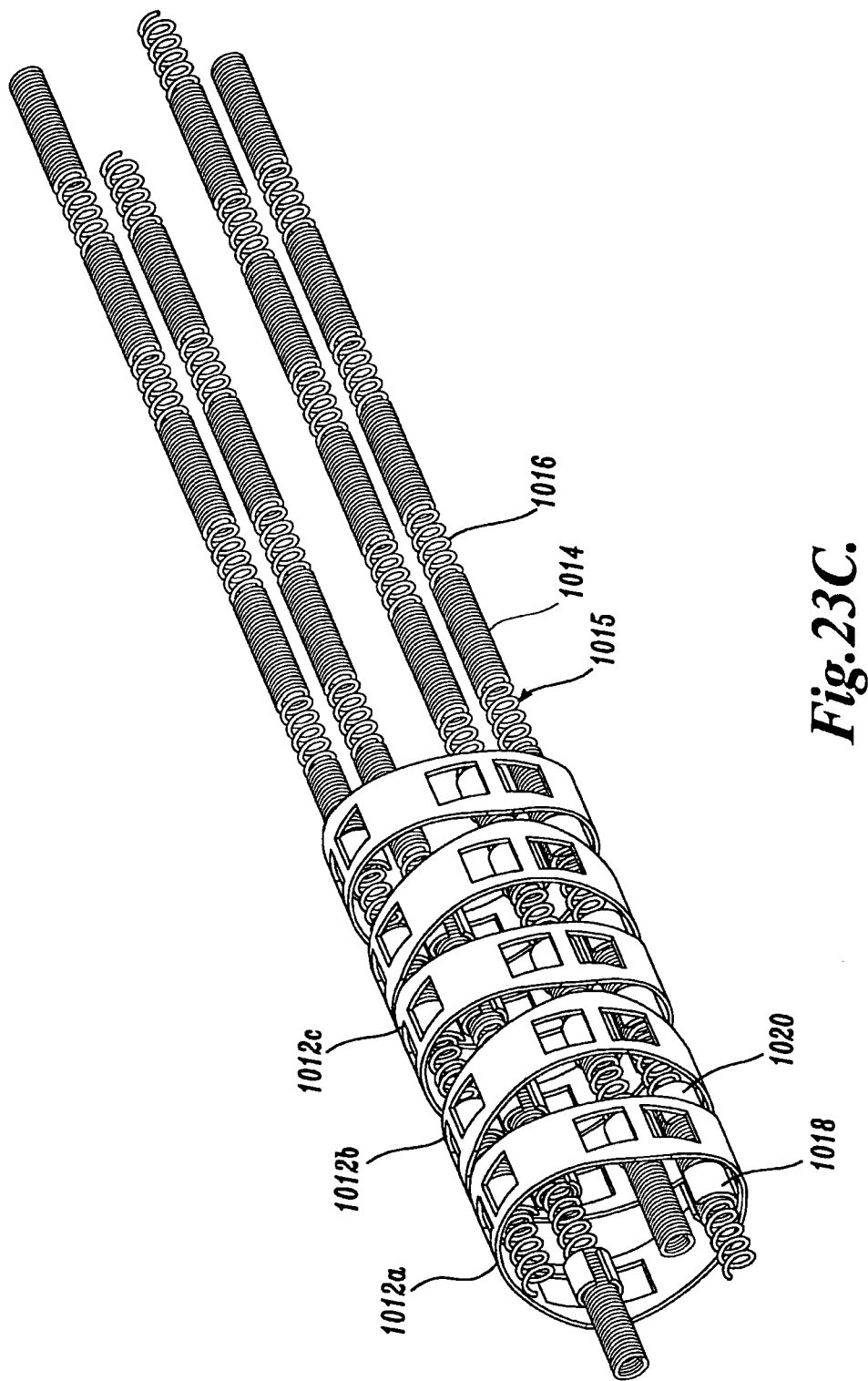

FIG. 23C shows another alternative embodiment of an articulation joint comprising a series of stacked metal rings 1012a, 1012b, 1012c, etc. Each ring 1012 is joined by a spring 1015 having alternate tightly wound sections 1014 and more loosely wound sections 1016, thereby varying the spring force along the length of the spring. The loosely wound sections 1016 allow the articulation joint to collapse in that area while the more closely wound sections 1014 provide the hinge mechanism for adjacent rings 1012. Each of the rings 1012 further includes a stamped pair of inwardly or outwardly extending tabs 1018 through which the springs are passed thereby forming a surface to which the springs can be crimped, welded, or otherwise secured. In the embodiment shown in FIG. 23C, each ring is not completely cylindrical but includes sloped front and rear surfaces 1020 that extend away from the point at which adjacent rings are joined. The sloped faces of the rings allow increased movement between adjacent rings and also provide a stop to prevent adjacent rings from sliding past each other. The sloped surfaces 1020 on adjacent rings thereby form a V-shaped groove in which the articulation joint is able to collapse.

Figure 23D:
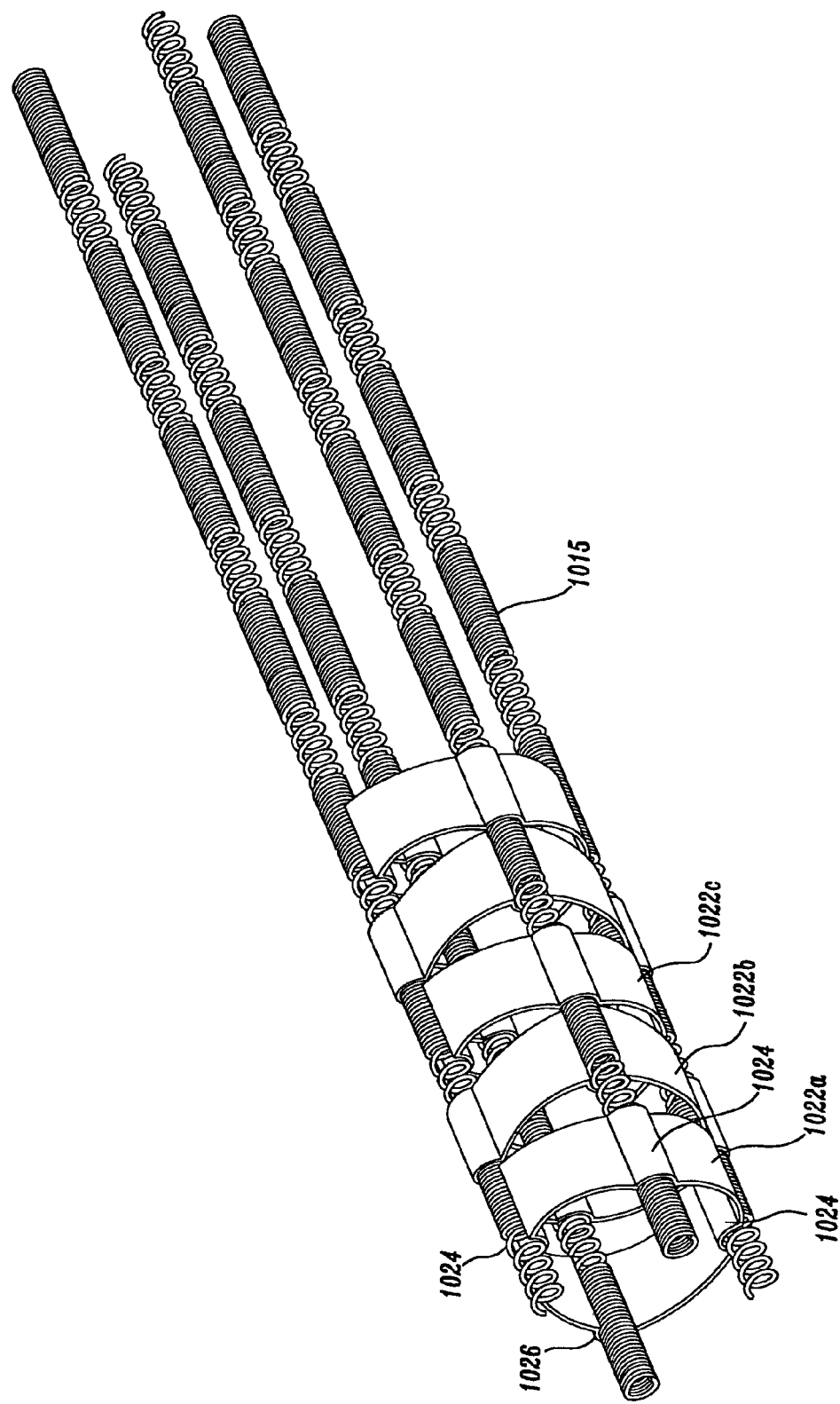

FIG. 23D shows another embodiment of an articulation joint that is similar to the articulation joint shown in FIG. 23B. However, in this embodiment, the articulation joint is comprised of a number of rings 1022a, 1022b, 1022c having oppositely arranged concave recesses 1024 and convex recesses that allow a spring 1015 having alternate tightly and loosely wound segments to pass on the outside of one ring and on the inside of an adjacent ring in an alternating fashion. The oppositely arranged convex and concave recesses allow a spring to be secured to the ring with an adhesive, welding, or other bonding mechanism.

Figure 23E:
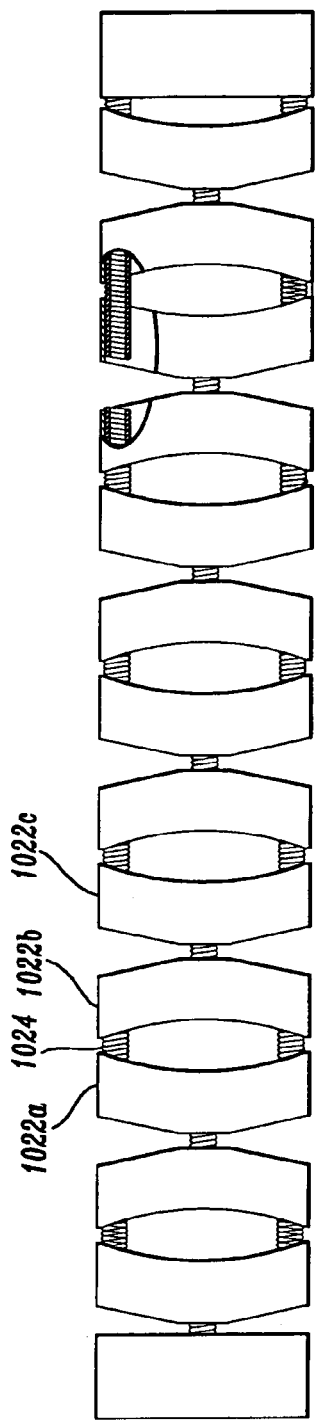
Figure 23F:
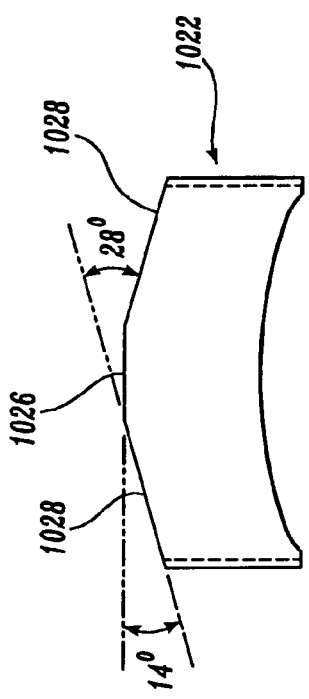

FIGS. 23E and 23F illustrate yet another embodiment of an articulation joint in accordance with the present invention. In this embodiment the joint is formed of a series of stacked links 1022a, 1022b, 1022c, etc., that are jointed with alternatingly orthogonally arranged pairs of spring segments 1024. The link may be formed by rolling and welding flat metal pieces. The spring segments 1024 are welded, brazed, adhesively secured or otherwise bonded to an inner circumference of each ring segment. The rings and spring segments are preferably made of stainless steel or other biocompatible metal. The springs may be secured to the rings prior to being cut with a laser or other cutting tool. Alternatively, the springs may be cut into segments and then secured to the rings with an assembly jig. Springs of varying stiffness may be used along the length of the joint to control the bending of the arc of the joint.

As shown in FIG. 23F, when viewed from the side, each ring has a front surface with a flat section 1026 and a pair of sloped sections 1028 that are sloped rearwardly from the flat surface 1026. The rear surface of the ring has a similar shape but the sloped surfaces are oriented at 90° to the sloped surfaces on the front side. Each sloped surface has an angle of 14° from a line perpendicular to the longitudinal axis of the joint, thereby allowing adjacent rings to bend approximately 28°.

Figures 23G, 23H:
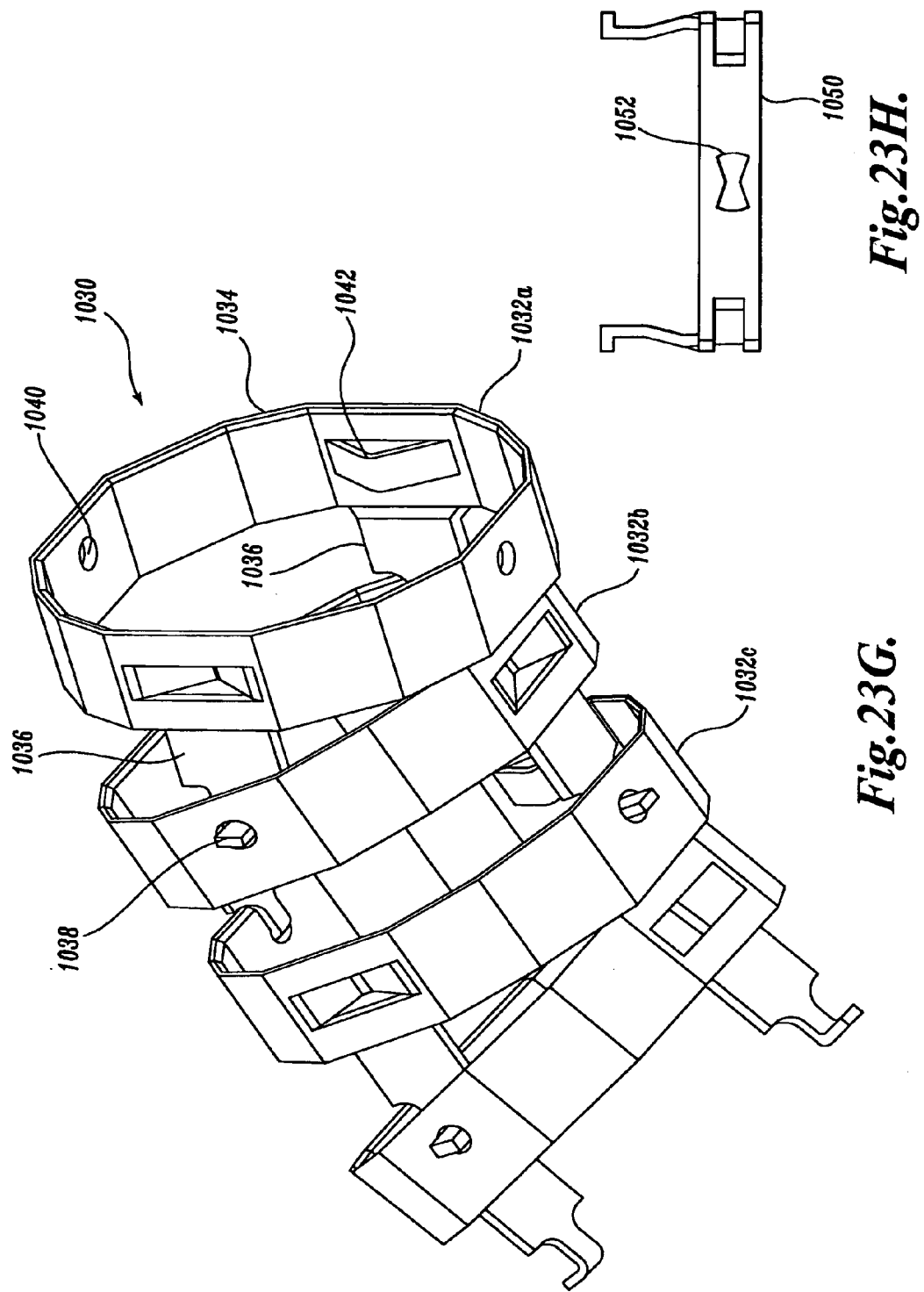

FIG. 23G shows yet another alternative embodiment of an articulation joint in accordance with the present invention. In this embodiment, the articulation joint 1030 comprises a series of metal links 1032a, 1032b, 1032c, etc., that are formed by deep drawing or stamping steel or another metal. Each link has a generally ring-like configuration 1034 that is either circular or may be many-sided such as octagonal. Furthermore, each link 1032 has a pair of rearwardly extending legs 1036 with an outwardly extending tab 1038 at the end thereof. Each of the legs 1036 is positioned on opposite sides of the link 1032. At 90 degrees to the legs 1036, the link 1032 includes corresponding holes 1040 in the sidewalls of the link that receive the tabs 1038 from an adjacent segment. Furthermore, the segment 1032 includes integrally formed wire guides 1042 comprising an eyelet for retaining the control cable. Adjacent links in the articulation joint are secured together by inserting the tabs 1038 from a first link 1032 into the corresponding holes 1040 of an adjacent link. A braid may be placed over the series of links to improve torsional strength without adding to the force required to bend the articulation joint. The braid may be incorporated into a cover that goes over the articulation joint.

FIG. 23H shows an alternative embodiment of a link like those shown in FIG. 23E. However, in this embodiment, the link 1050 has a butterfly-shaped hole 1052 instead of the round holes 1040 to receive the tabs of an adjacent link. The butterfly-shaped hole 1052 serves to limit the extent by which a corresponding flat tab can be rotated from an adjacent link. By adjusting the curvature of the arcs that form the butterfly-shaped hole 1052, the degree of rotation between adjacent links can be controlled. The links 1050 are preferably formed by deep drawing metal and/or stamping operations.

Figure 23I:
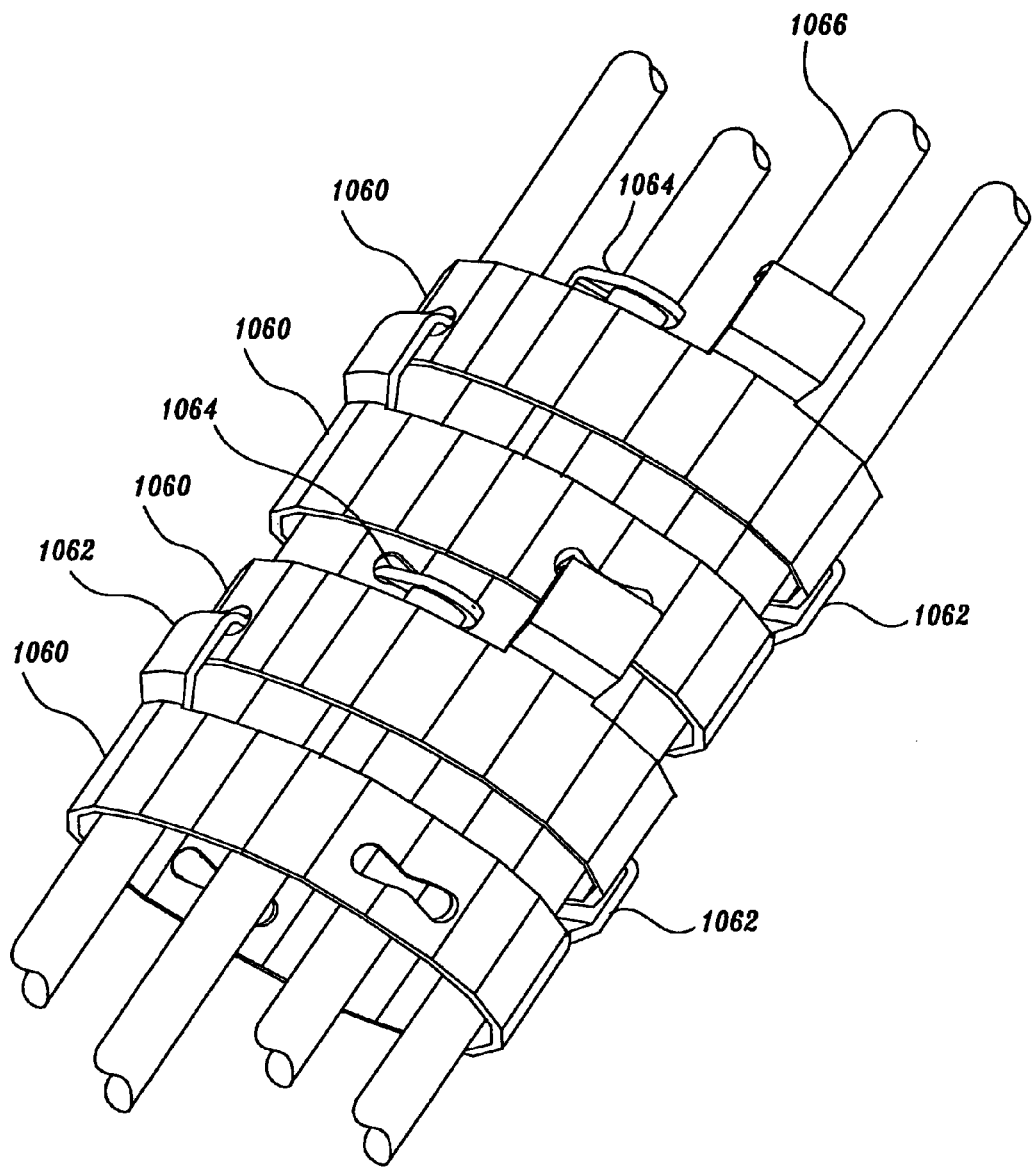

FIG. 23I illustrates yet another embodiment of an articulation joint of the present invention that is formed of a series of interconnected metal links 1060. Each link 1060 has a pair of rearwardly extending opposing legs 1062 having inwardly extending tabs at each end. The tabs extend into corresponding holes or slots of an adjacent link. However, in this embodiment, the tabs on each of the legs 1062 extend further into the central lumen of the articulation joint. Each tab also includes a hole 1064 through which a spring 1066 can pass. The holes 1064 thereby lock the tab in the adjacent link because the spring 1066 prevents the tab 1062 from being withdrawn from an adjacent link.

Figure 23J:
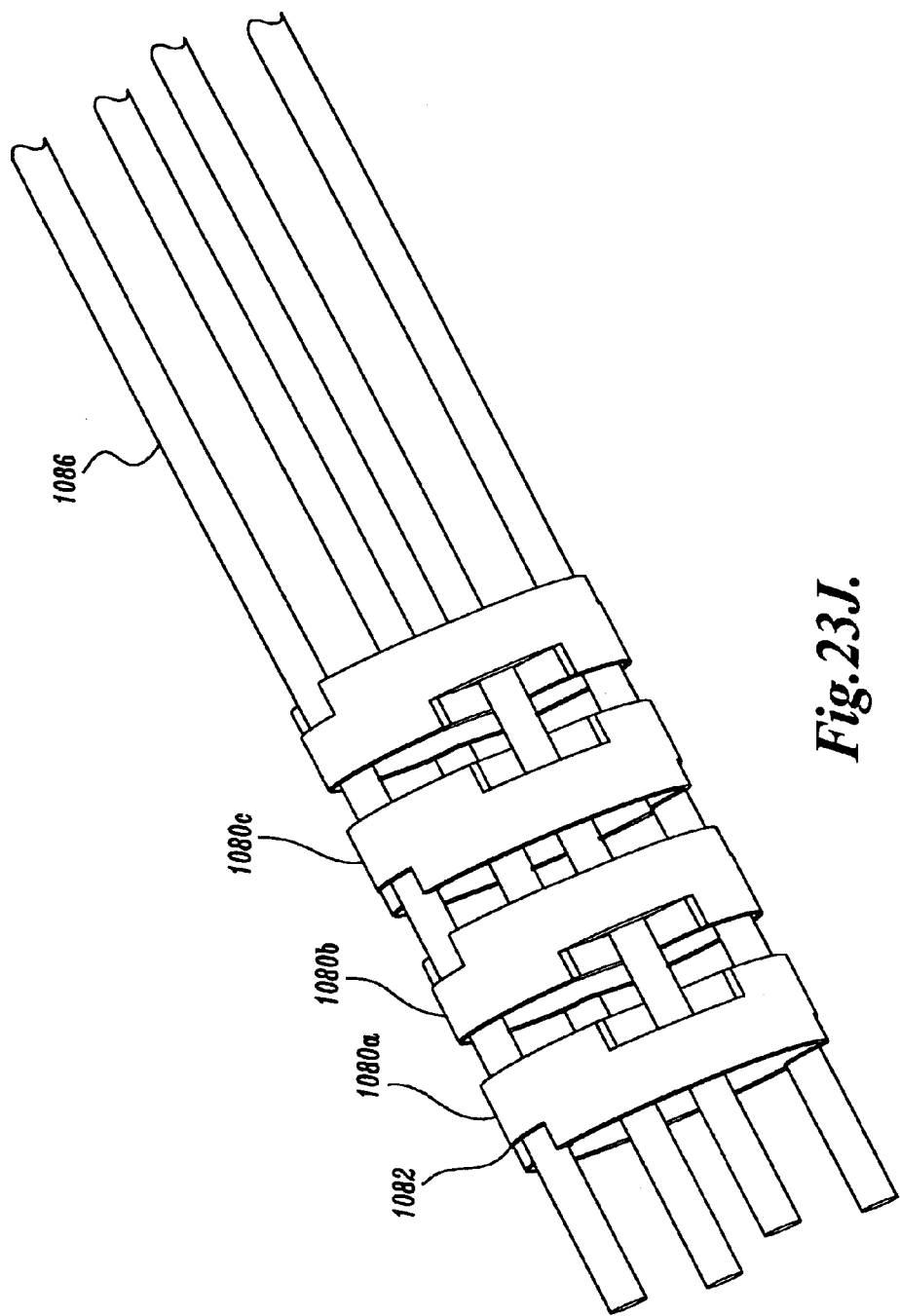

FIG. 23J illustrates yet another embodiment of an articulation joint of the present invention that is of a series of interconnected links 1080a, 1080b, 1080c, etc. Each link has alternating hoops or eyelets 1082 around the circumference thereof that are formed by making a slot that extends circumferentially around a portion of the link, followed by bending a portion of the link inwardly. The slots are arranged such that a pair of inwardly extending eyelets is formed on opposite sides of a front surface of the link with a pair of eyelets oriented at 90° to the eyelets on the front surface formed on the rear surface of the link. With the eyelets thus formed in the links 1080a, 1080b, 1080c, etc., the springs 1086 can be secured to the links at each of the eyelets.

Figure 23K:
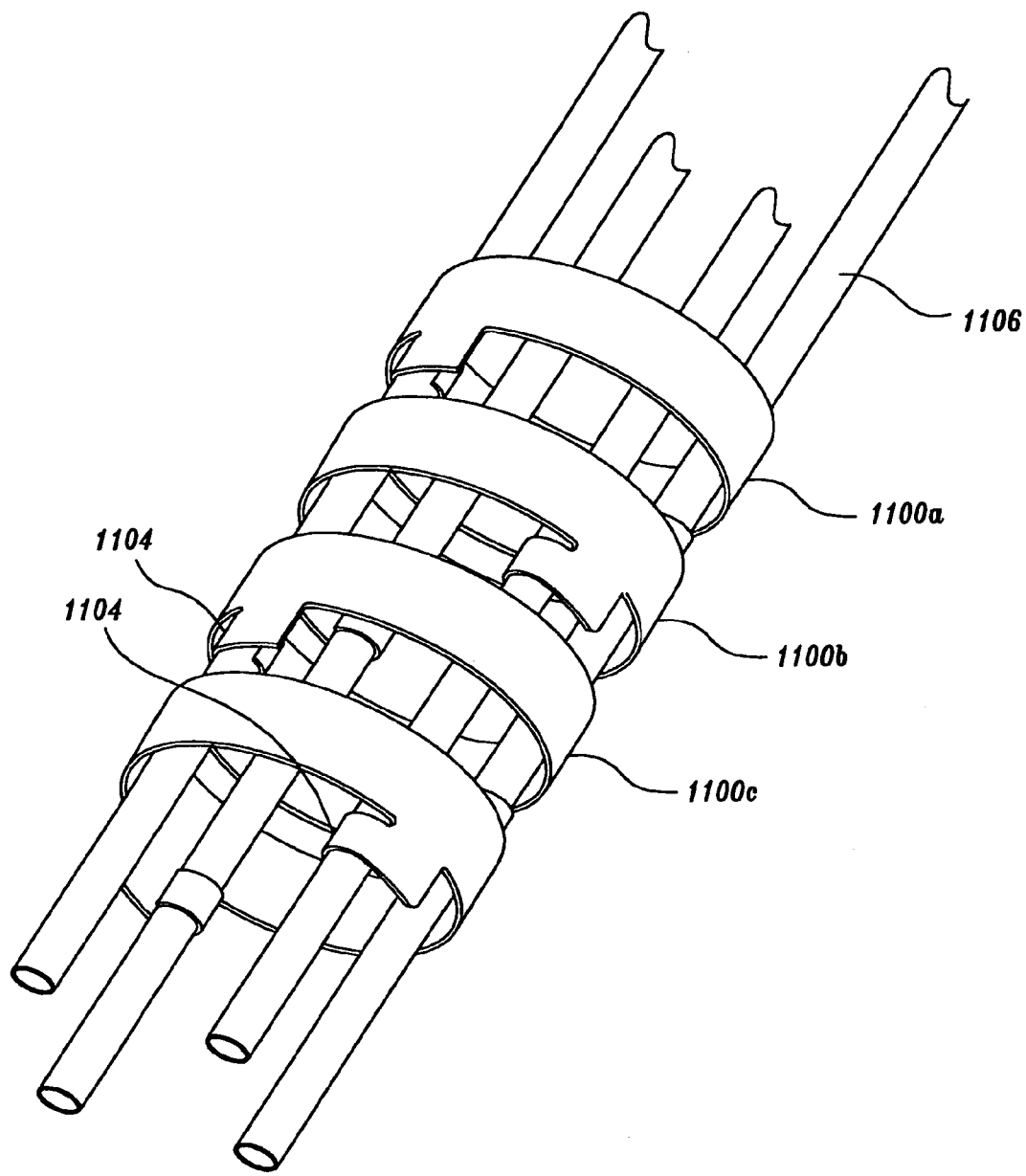

FIG. 23K shows another embodiment of an articulation joint of the present invention that is similar in arrangement to the articulation joint shown in FIG. 23J. In this embodiment, the articulation joint comprises a series of metal links 1100a, 1100b, 1100c, etc. Each link includes a pair of oppositely formed, inwardly extending tabs 1104 that are bent in a circle through which an elastomeric tube or spring 1106 can be passed. The tubes or springs 1106 are secured in the link by crimping, welding or otherwise securing the tubes, springs 1106 to the tabs 1104.

Figure 23L:
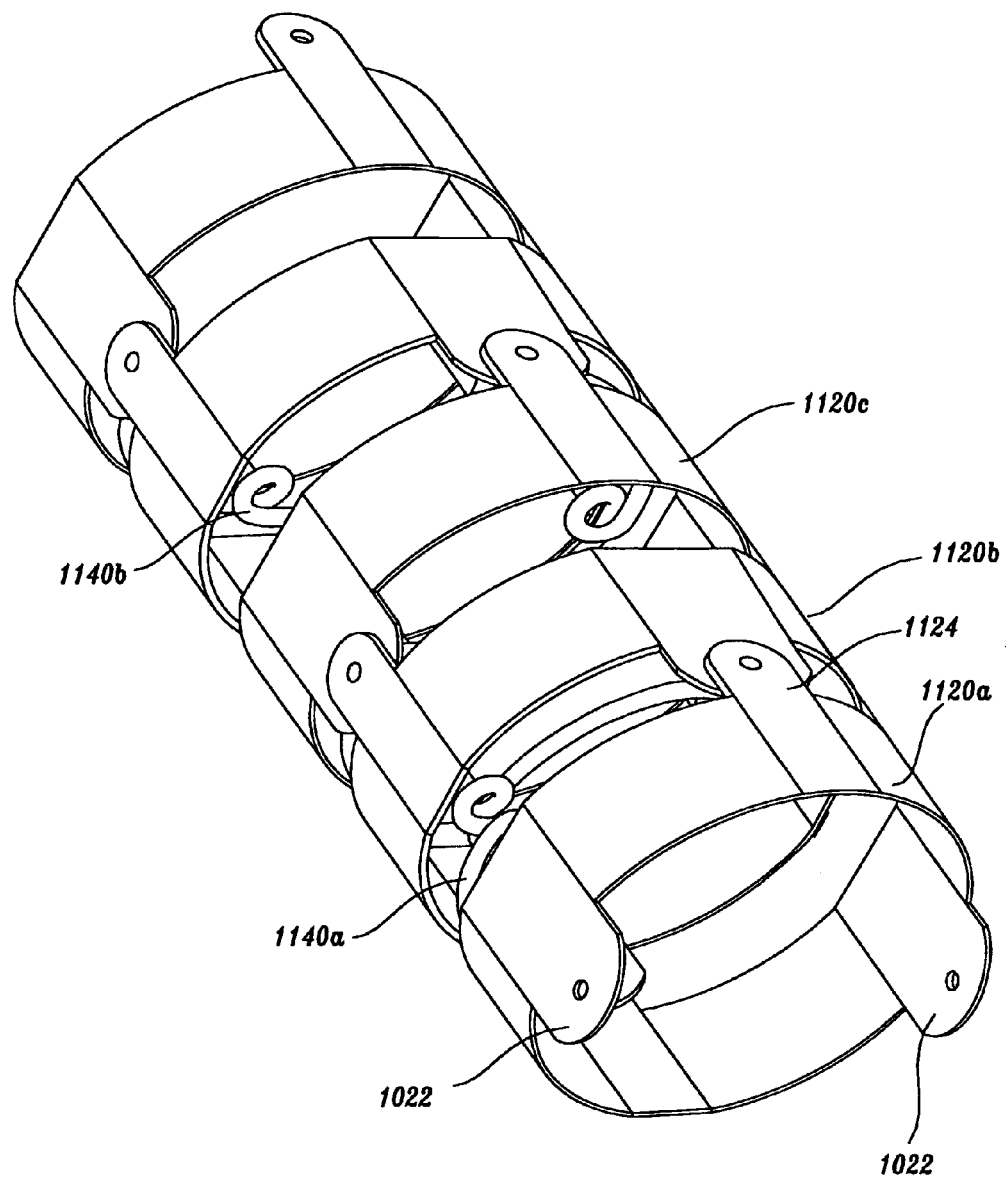
Figure 23M:
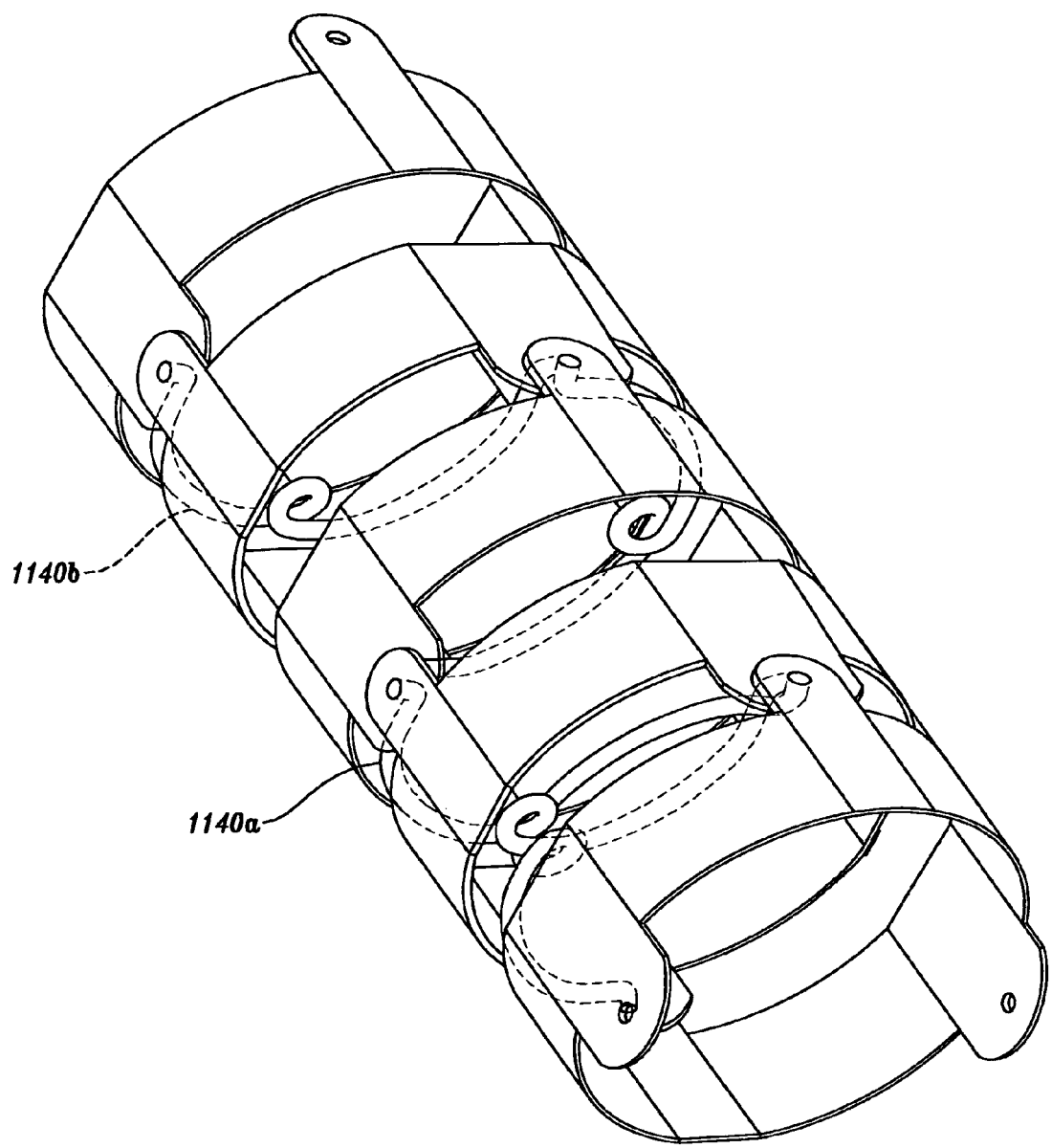

FIG. 23L shows yet another alternative embodiment of an articulation joint in accordance with the present invention. In this embodiment, the articulation joint comprises a series of stamped or deep drawn metal links 1120a, 1120b, 1120c, etc. Each link includes a pair of forwardly extending tabs 1022 on its front surface and a pair of rearwardly extending tabs 1124 on its rear surface. The tabs 1022 and 1124 on the front and rear surfaces are oriented at 90 degrees with respect to each other. Each of the tabs 1022, 1124 includes a hole through which a securing mechanism can be passed in order to secure aligned tabs together. As shown in FIG. 23M, the securing mechanism is provided by a series of wire springs 1140a, 1140b, etc. Each spring comprises a wire with an end that is inserted through the holes of an aligned pair of tabs of the articulation joint. The spring 1140a, 1140b then travels along the interior lumen of the articulation joint and has a second end that terminates through the holes of another set of aligned tabs that connect another pair of links. Each spring may further include a loop wound therein that acts as an eyelet for retaining a control wire therein.

FIGS. 23N-23P illustrate yet another embodiment of an articulation joint 1200 for use in a disposable endoscope of the present invention. In this embodiment, the articulation joint comprises a series of stacked discs of the type shown in FIG. 23N. Each disc 1202 has a front face 1206 and a rear face 1208 and a central opening 1212. Equally spaced around the periphery of the disc are a number of holes 1210 through which a control cable can pass. The front face 1206 includes a pair of oppositely arranged flat sections 1207 that bisects the disc and defines a pair of surfaces that may engage a corresponding flat surface of an adjacent disc. The front face of the discs further include two sloped sections that are angled proximally away from the flat surface 1207. In one embodiment of the invention, the sloped sections are angled at approximately 14° from a line perpendicular to the longitudinal axis of the disc. Similarly, the rear face 1208 includes two sloped sections that are angled distally away from a pair of flat surfaces that are rotated 90° with respect to the flat surface 1207 on the front face of the disc. As shown in FIG. 23P, the articulation joint 1200 is created by stacking a number of discs 1202a, 1202b, 1202c, etc., such that each disc is aligned with an adjacent disc at the flat surfaces, whereby the sloped sections form a hinge that can close under the tension of a control cable passing through the articulation joint. In the embodiment shown in FIG. 23P, there are seven pairs of stacked segments 1202, wherein each pair is capable of producing a 280 bend. Therefore, the articulation joint 1200 shown in FIG. 23P can bend a total of 1960 in the up, down, left, or right directions. At the proximal end of the articulation joint 1200 is a proximal connector 1220 that joins the articulation joint to the distal end of the shaft. An outer sheath (not shown) covers the series of stacked discs 1202 to prevent each disc from becoming misaligned.

Figure 23Q:
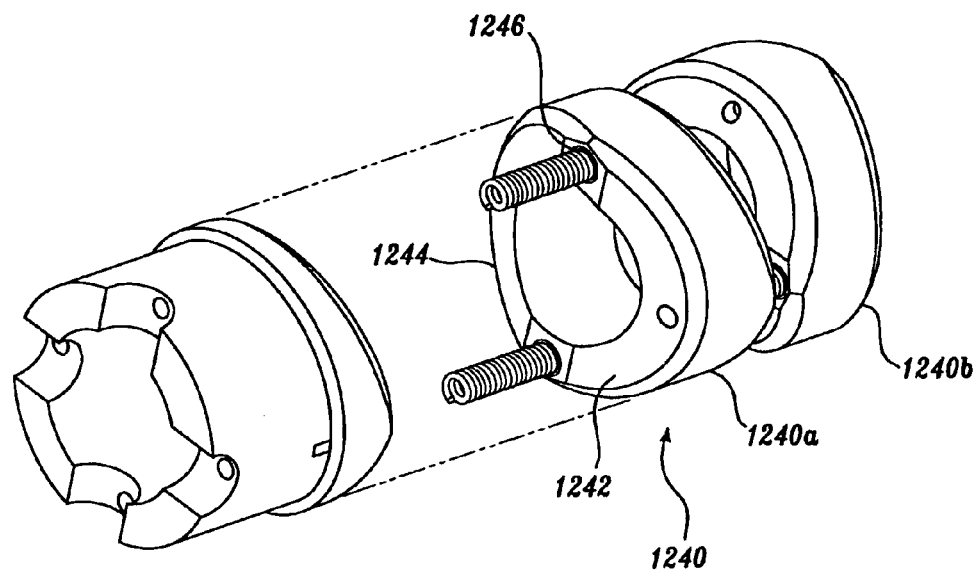

FIG. 23Q shows another disc that is used for the articulation joint of the present invention. Each disc 1240 is similar to the discs 1202 shown in FIGS. 23N and 23M. In this embodiment, each segment has a front face with a pair of sloping surfaces 1242, 1244 that slope away from a pair of opposing flat surfaces 1246. Similarly, on the rear surface of each segment, the sloping surfaces are arranged orthogonally to the sloping surfaces on the front surface. Adjacent discs 1240a, 1240b are secured together by a pair of oppositely arranged spring segments that have their ends set in a recess or a countersink formed in the flat surface portion of the disc front and rear surfaces. The spring segments also act as guides through which the control cables can pass. Furthermore, the springs prevent adjacent segments from rotating with respect to each other or otherwise becoming misaligned.

Figure 23R:
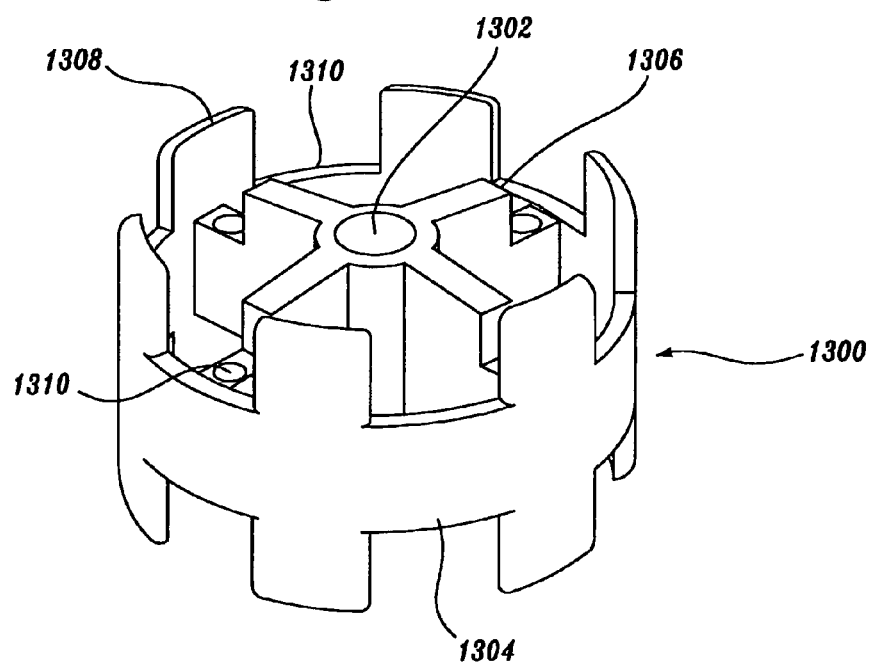

FIG. 23R shows another alternative embodiment of a segment that can be used to form an articulation joint in accordance with the present invention. In this embodiment, the articulation joint is comprised of a series of segments 1300 having a central, cylindrical axle 1302 and an outer cylindrical rim 1304. The axle 1302 is joined to the outer cylinder 1304 by a number of outwardly extending spokes 1306. Each spoke is sloped from the center point near the axle downwards towards the midline of the outer ring 1304. The sloped spokes 1306 allow adjacent segments to touch at the axle points and be rotated with respect to each other without the spokes hitting each other. Each spoke further includes a lumen 1312 towards the outer edge, through which a control cable can be passed. The outer rim 1304 of the segment 1300 has alternately spaced teeth 1308, 1310 that are circumferentially arranged such that the teeth of one segment align with the recesses of an adjacent segment. This design ensures that internal tubes do not get entangled during articulation.

Figure 23S:
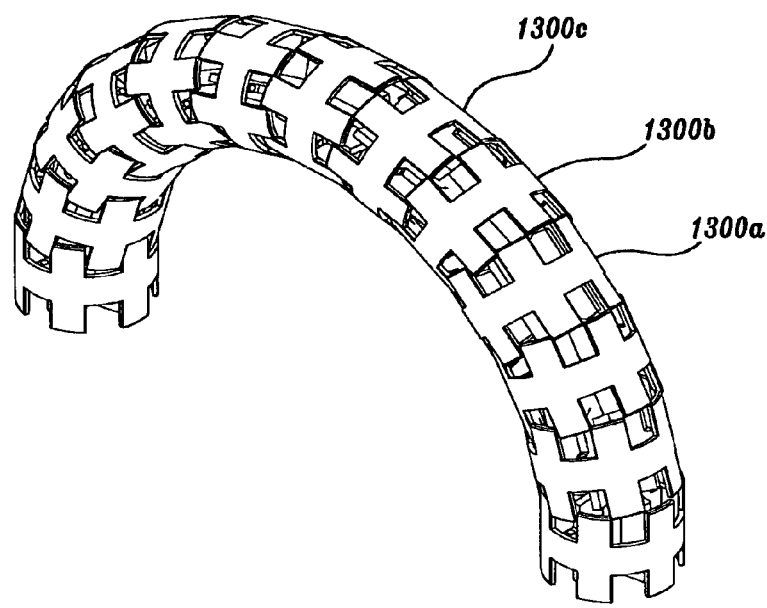

FIG. 23S shows a series of segments 1300a, 1300b, 1300c, etc., bending with respect to each other to form an articulation joint. Each of the individual segments 1300 is preferably molded of a thermoplastic material or metal.

Figure 23T:
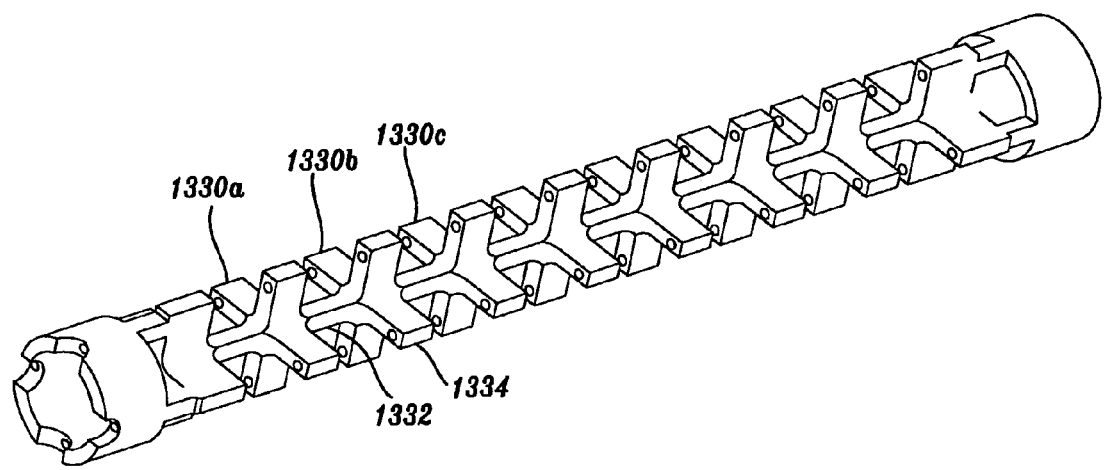

FIG. 23T shows another alternative embodiment of an articulation joint in accordance with the present invention. In this embodiment, the articulation joint is formed of a series of segments 1330a, 1330b, 1330c, etc. Each segment comprises a central pin 1332 and radially extending legs 1334 at one end thereof. At the outer edge of each leg 1334 is a hole through which a control cable can be passed. The end of the central pin fits against a segment like a spinal column thereby allowing each segment 1332 to rock against an adjacent segment. In some embodiments, it may be desirable to cover the segments with a mesh tube to retain the alignment of the individual segments.

Figure 23U:
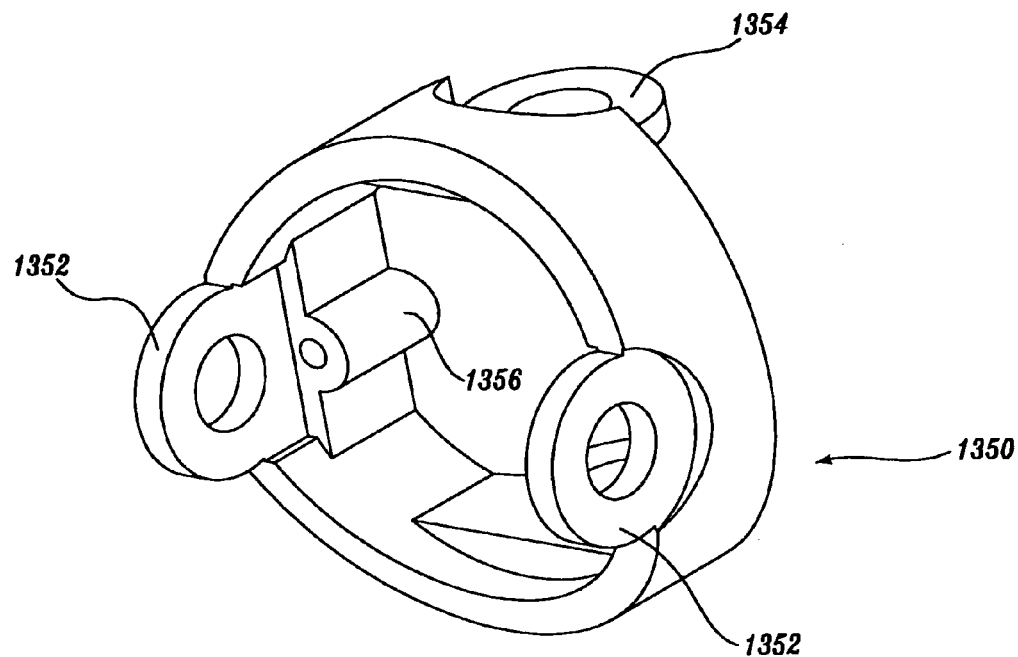

FIG. 23U illustrates another embodiment of a link that is joined to adjacent links to form an articulation joint in accordance with the present invention. In this embodiment, the link comprises a metal injection molded ring having a pair of oppositely arranged, rearwardly extending rings 1352 and a pair of forwardly extending rings 1354 that are oriented at 90° with respect to the rearwardly extending rings 1352. Adjacent rings are therefore aligned by placing the forwardly extending rings of one link against the rearwardly extending rings of an adjacent link. Each ring 1352 or 1354 includes a hole therein through which a rivet can be passed in order to secure the rings together. The inner circumference of the ring 1350 includes a pair of integrated control cable guides 1356 for restraining movement of a control cable in the link.

Figure 23V:
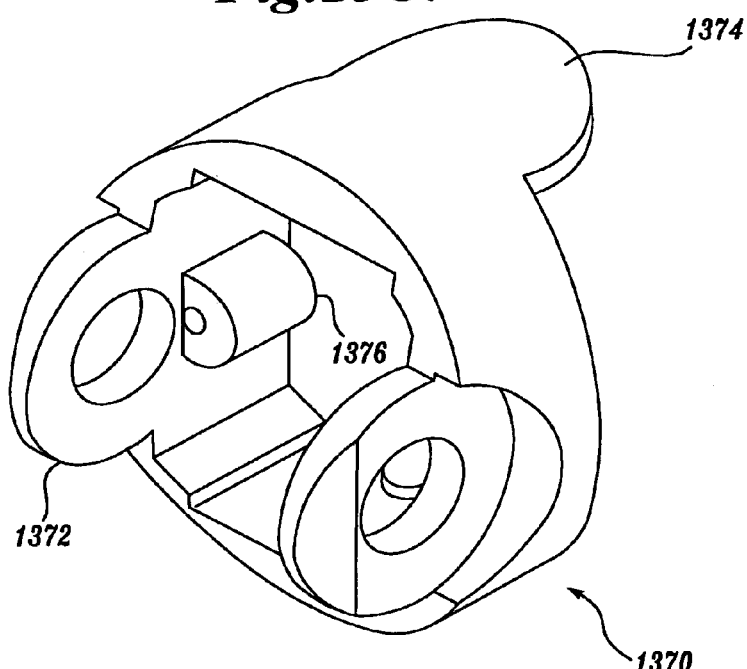

FIG. 23V illustrates an alternative embodiment of a link 1370 that is similar to the link 1350 shown in FIG. 23T. In this embodiment, each link includes a pair of rearwardly extending tabs 1372 having a hole therein and a pair of forwardly extending tabs 1374 that have an integrally formed pin (not shown) on its inner surface. Once joined, the tabs 1374 having the inwardly extending pins are mated in the holes in the rearwardly extending tabs 1372 of an adjacent link, thereby eliminating the need to secure adjacent links with a separate rivet. The link 1370 also includes a pair of oppositely aligned control cable guides 1376 for restraining movement of a control cable in the link 1370.

Figure 23W:
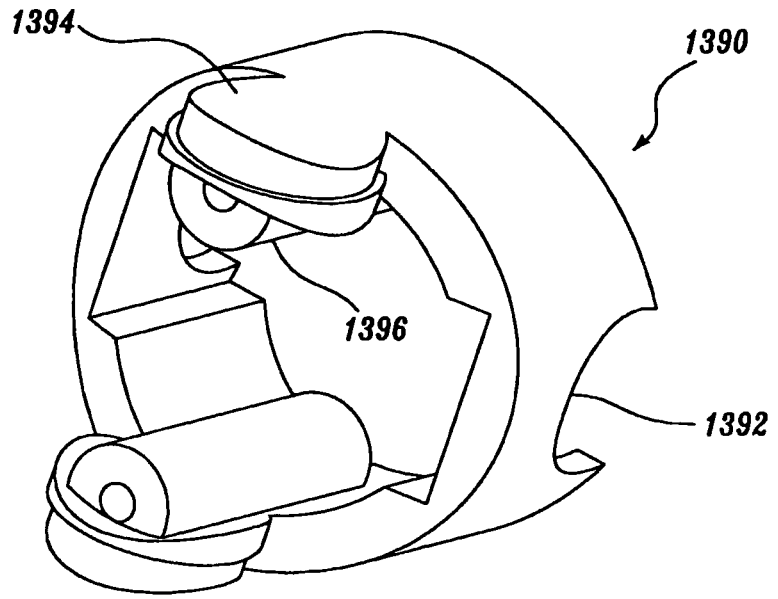
Figure 23X:
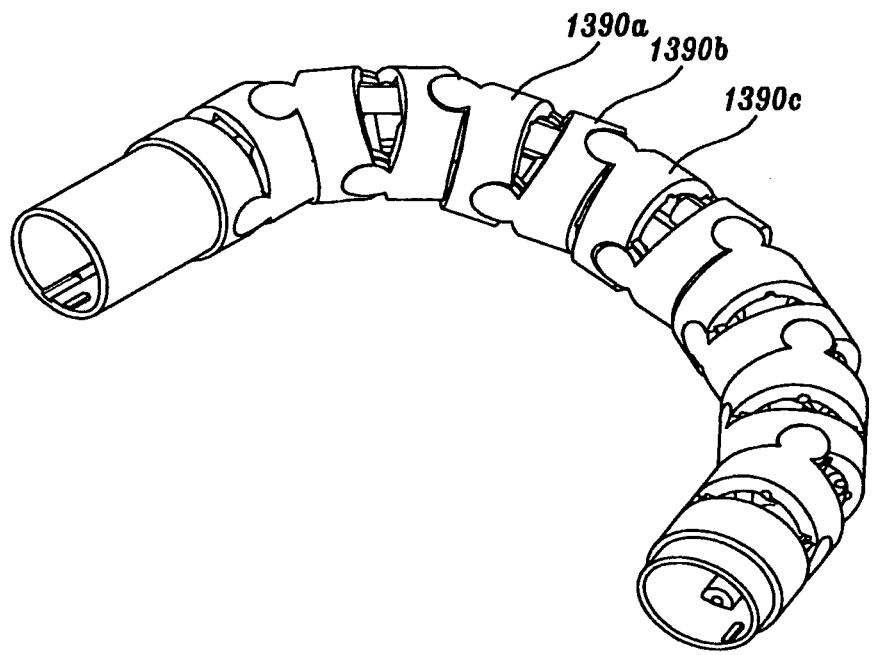

FIGS. 23W and 23X show another alternative embodiment of a link that is assembled with other links to form an articulation joint in accordance with the present invention. In this embodiment, the link 1390 comprises an injection molded ring having a pair of oppositely opposed arcuate recesses 1392 on its rear surface and correspondingly shaped, forwardly extending arcuate tabs 1394 on its front surface. The tabs 1394 on the front surface are orthogonally arranged with respect to the arcuate recesses 1392 on a rear surface. Aligned with the inside surface of each of the arcuate tabs 1394 is an integrally formed control cable lumen 1396 that restrains movement of a control cable in the link 1390.

Because the link 1390 is molded of a thermoplastic material, the arcuate tabs 1394 can be press fit into the arcuate recesses 1392 of an adjacent link, thereby permitting the adjacent links to rock back and forth with respect to each other. FIG. 23X shows links 1390a, 1390b, and 1390c connected together.

In some embodiments, the articulation joint is designed to exert a restoring force so that the endoscope will tend to straighten upon the release of tension from the control cables. In other cases, it may be desirable to maintain the position of the distal tip in a certain direction. In that case, a construction as shown in FIG. 24 can be used. Here, the shaft of the imaging endoscope includes an inner sleeve 1450 that is overlaid with two or more plastic spiral wraps 1452, 1454, and 1456. Wrap 1452 is wound in the clockwise direction while wrap 1454 is wound in the counter-clockwise direction over the wrap 1452 and the wrap 1456 is wound in the same direction as the first wrap 1452. The wraps are formed of a relatively coarse plastic material such that friction is created between the alternatingly wound layers of the wrap. A suitable material for the plastic wrap includes a braided polyester or polyurethane ribbon. Upon tension of the endoscope by any of the control cables, the plastic spiral wraps will move with respect to each other and the friction between the overlapping wraps will tend to maintain the orientation of the endoscope in the desired direction. The endoscope will remain in the desired direction until it is pulled in a different direction by the control cables. Covering the alternatingly wound spiral wraps 1452, 1454, and 1456 is a braid 1458. The braid is formed of one or more plastic, glass fiber or wire threads wound in alternate directions. An outer sleeve 1460 covers the braid 1458 to complete the shaft.

FIG. 25 shows another alternative embodiment of a shaft construction for use in an endoscope according to the present invention. The shaft includes a cover sheath 1470 having bands of a high durometer material 1472 and a low durometer material 1474 that alternate around the circumference of the sheath 1470. The high durometer material and low durometer materials form longitudinal strips that extend along the length of the shaft. Within the sheath 1470 is a plastic spiral wrap 1475 that prevents the shaft 1470 from crushing as it is bent in a patient's anatomy. The high durometer materials add to the torque fidelity characteristics of the shaft. The width of the high durometer material strips compared to the low durometer material may be adjusted in accordance with the torque fidelity characteristics desired.

Figure 26:
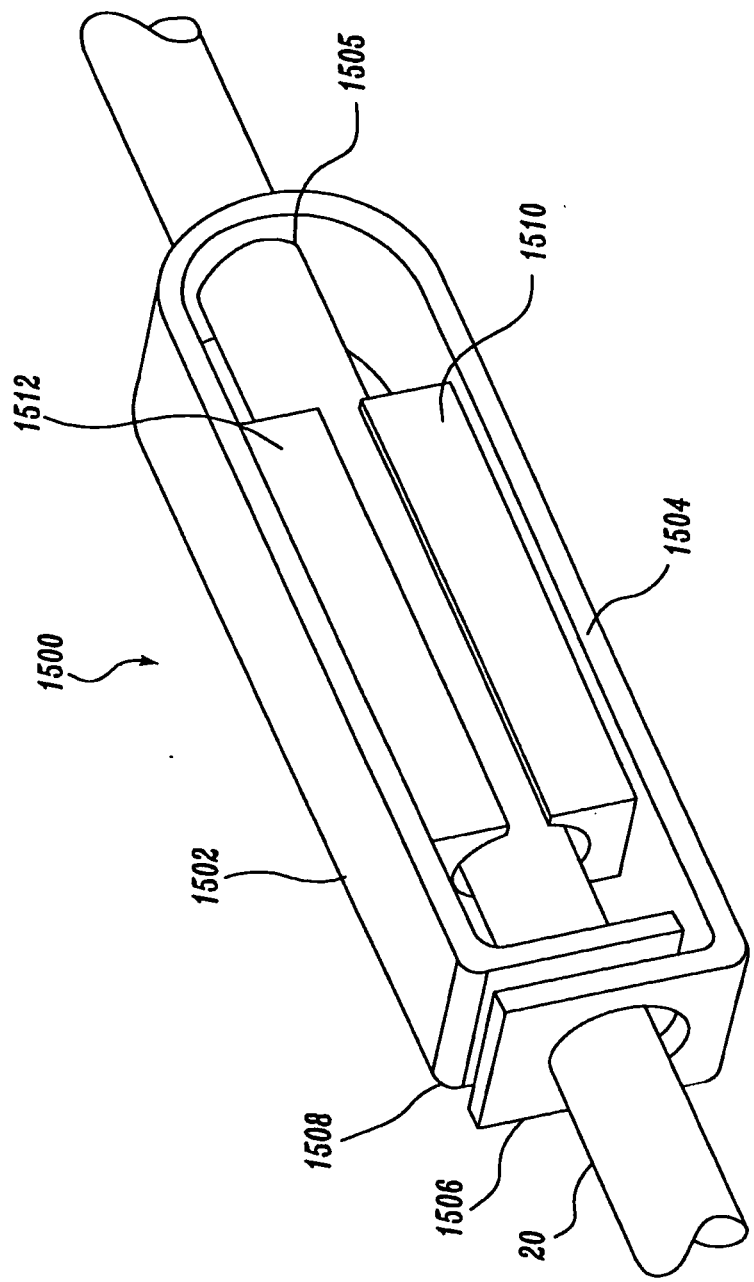
FIGS. 26-29 illustrate alternative embodiments of a gripping mechanism that rotates an endoscope in accordance with the present invention.

During examination with the imaging endoscope, the physician may need to twist the endoscope in order to guide it in the desired direction. Because the outer surface of the endoscope is preferably coated with a lubricant and it is round, it can be difficult for the physician to maintain an adequate purchase on the shaft in order to rotate it. As such, the imaging endoscope of the present invention may include a gripper mechanism that aids the physician in grasping the shaft for either rotating it or moving the shaft longitudinally. One embodiment of a shaft gripping device is shown in FIG. 26. Here, a gripper 1500 comprises a U-shaped member having a pair of legs 1502, 1504 that are aligned with the longitudinal axis of an imaging endoscope 20. At the distal end of the legs 1502, 1504 are two 90° bends 1506, 1508. The gripper 1500 includes a hole 1505 positioned at the curved, bent portion of the gripper that joins the legs as well as holes in each of the 90° sections 1506, 1508. The imaging endoscope passes through the holes such that the gripper 1500 is slideable along the length of the shaft portion of the endoscope. The spring nature of the material used to fashion the gripper causes the legs 1502, 1504 to be biased away from the shaft of the endoscope. Only the friction of the opposing holes at the bent portions 1506, 1508 prevent the gripper 1500 from freely sliding along the length of the shaft. On the inner surface of the legs 1502, 1504 are a pair of touch pads 1510, 1512, having an inner surface that is shaped to match the outer circumference of the shaft portion of the endoscope. When the physician squeezes the legs 1502, 1504 radially inward, the touch pads 1510, 1512 engage the shaft such that the physician can push or pull the endoscope or rotate it. Upon release of the legs 1502, 1504, the touch pads 1510, 1512 release from the surface of the shaft and the gripper 1500 can be moved along the length of the shaft to another location if desired.

Figure 27:
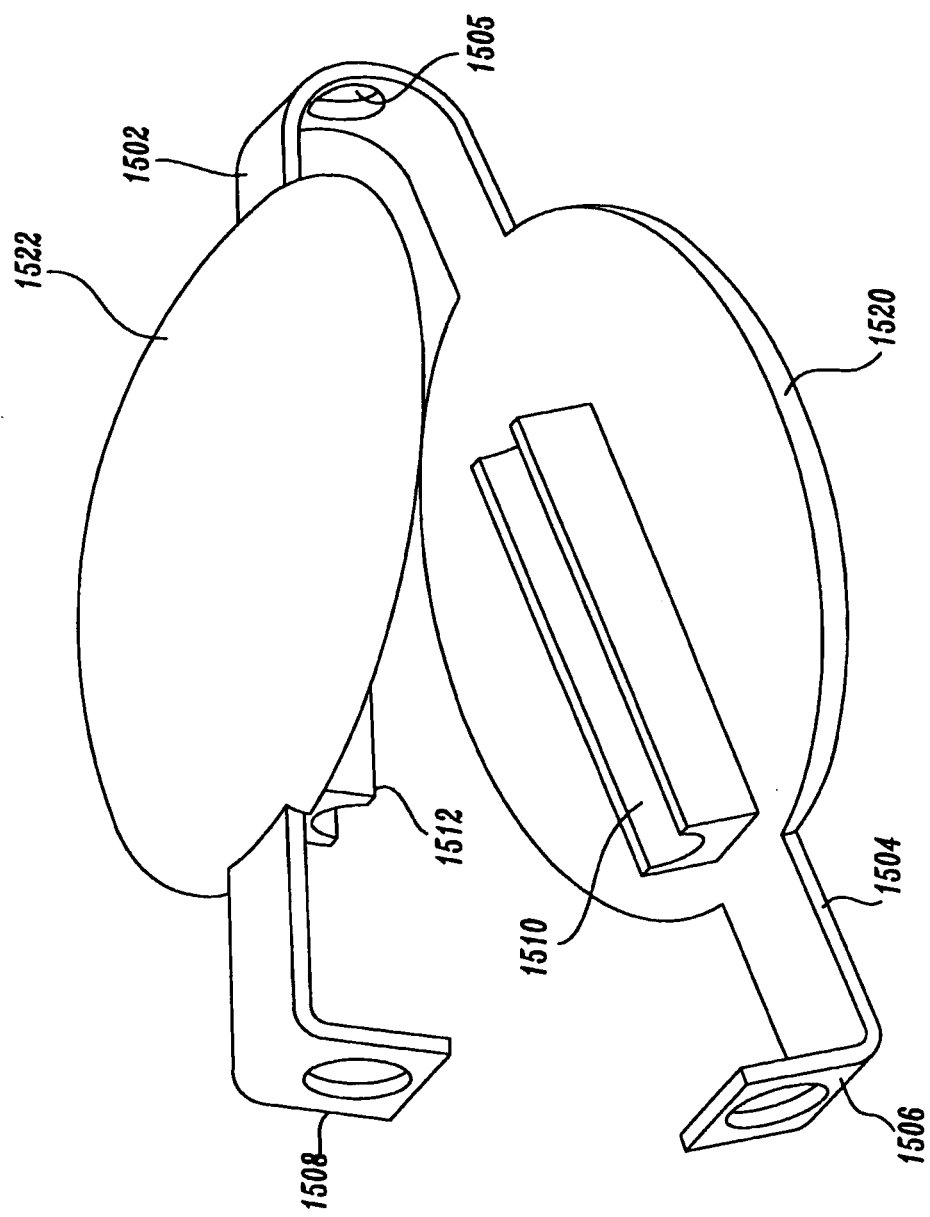

FIG. 27 shows a gripper similar to that of FIG. 26 with like parts being identified with the same reference numbers. In this embodiment, the gripper includes two hemispherical discs 1520, 1522, positioned on the outside surface of the legs 1502, 1504. The hemispherical surfaces 1520, 1522 are designed to fit within the hand of the physician and increase the radial distance from the gripper to the shaft such that it is easier to twist the shaft, if desired.

Figure 28:
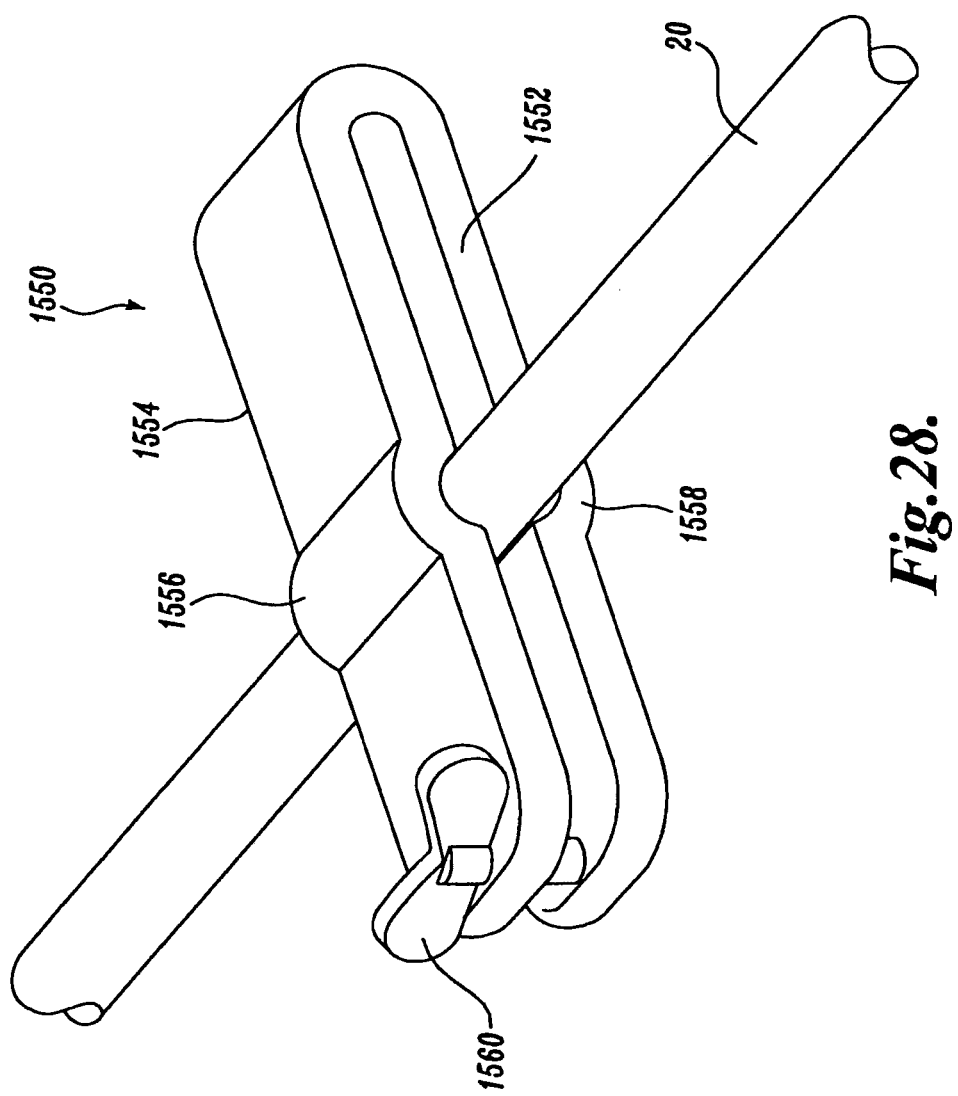

FIG. 28 shows yet another alternative embodiment of a shaft gripper. In this example, a gripper 1550 comprises a U-shaped member having a pair of legs 1552, 1554, that are oriented perpendicularly to the longitudinal axis of the imaging endoscope. The legs 1552, 1554 include a recessed section 1556, 1558 that is shaped to receive the outer diameter of the shaft portion of the endoscope. A thumbscrew 1560 is positioned at the distal end of the legs such that the legs can be drawn together and cause the legs 1554, 1556 to securely engage the shaft of the endoscope. Upon release of the thumbscrew 1560, the legs 1554, 1552 are biased away from the shaft such that the gripper 1550 can be moved. The shaft can be twisted by rotating the legs 1552, 1554, with respect to the longitudinal axis of the shaft.

Figure 29:
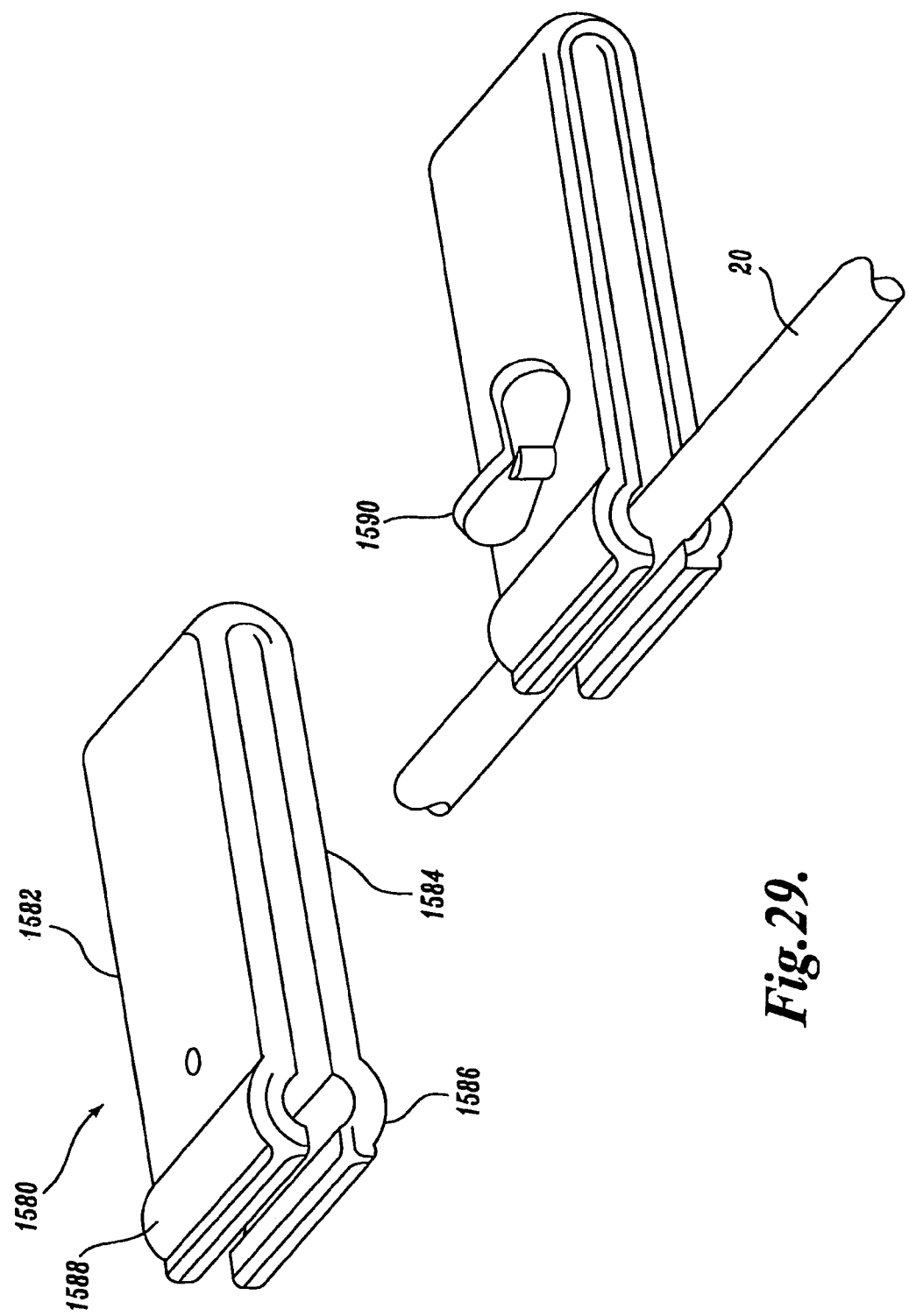

FIG. 29 shows an alternative embodiment of the gripper 1550 shown in FIG. 28. In this example, the gripper 1580 includes a U-shaped member having a pair of legs 1582, 1584. At the distal end of each leg is a recess 1586, 1588 that is shaped to receive the outer diameter of the shaft. The shaft is placed in the recesses 1586, 1588, and a thumbscrew is positioned between the ends of the legs 1582, 1584, and the U-shaped bend in the gripper 1580. By tightening the thumbscrew 1590, the legs are compressed against the shaft of the imaging endoscope 20, thereby allowing the physician to rotate the endoscope by moving the gripper 1580.

In one embodiment of the invention the endoscope has a movable sleeve that operates to keep the distal end of the endoscope clean prior to use and covers the end of the endoscope that was in contact with a patient after the endoscope has been used.

FIGS. 30A and 30B illustrate one embodiment of an endoscope 1594 having a sponge 1596 at its distal end. The sponge fits over the endoscope and has a peel off wrapper that may be removed and water or other liquid can be applied to the sponge. The water activates a hydrophilic coating so that the distal end of the endoscope has an increased lubricity. In addition, the sponge functions as a gripper when compressed allowing the physician to pull and/or twist the endoscope.

A collapsible sleeve 1598 is positioned over the distal end of the endoscope and can be retracted to expose the lubricated distal tip of the probe. In one embodiment, the sleeve 1598 is secured at its distal end to the sponge 1596 and at its proximal end to the breakout box. Moving the sponge proximally retracts the sleeve so that the endoscope is ready for use. After a procedure, the sponge 1596 is moved distally to extend the sleeve over the distal end of the endoscope. With the sleeve extended, any contaminants on the probe are less likely to contact the patient, the physician or staff performing the procedure.

Figure 31:
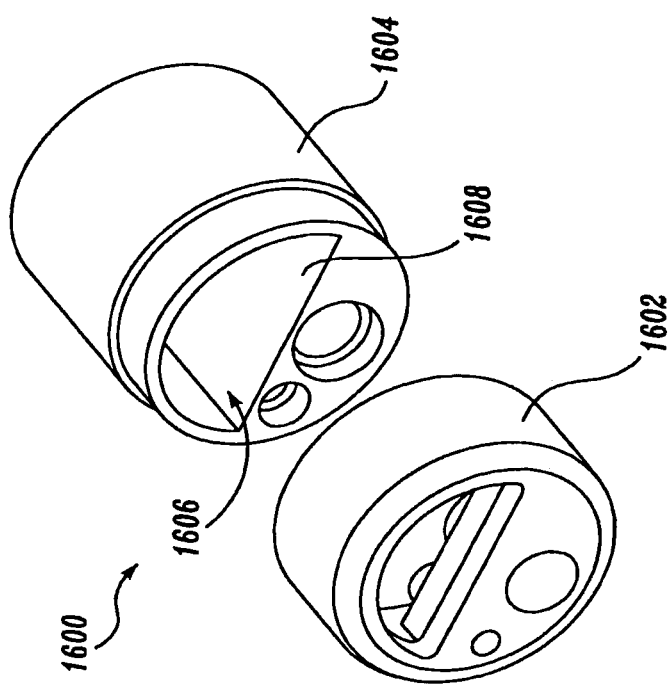
FIG. 31 illustrates an embodiment of a passive heat dissipating distal tip of an endoscope in accordance with the present invention.

In some instances, it may be desirable to limit the amount of heat that is dissipated at the distal end of the imaging endoscope. If light emitting diodes are used, they generate heat in the process of producing light for illumination. Similarly, the image sensor generates some heat during operation. In order to limit how hot the distal end of the endoscope may become and/or to provide for increased life for these components, it is necessary to dissipate the heat. One technique for doing so is to fashion a passive heat sink at the distal tip of the imaging endoscope. As shown in FIG. 31, a distal tip 1600 includes a cap 1602 and a heat dissipating section 1604 that is made of a heat dissipating material such as a biocompatible metal. The heat dissipating section 1604 includes a semicircular opening 1606 having a relatively flat base 1608 that extends approximately along the diameter of the heat dissipating section 1604. The flat base 1608 forms a pad upon which electrical components such as the LEDs and image sensor can be mounted with a thermally conductive adhesive or other thermally conductive material. The heat generating devices will transfer heat generated during operation to the heat dissipating section 1604. The distal cover 1602 covers the distal end of the heat dissipating section 1604 in order to prevent the heat dissipating section 1604 from touching the tissue in the body as well as to protect the body as the imaging catheter is moved in the patient. Prisms, lenses, or other light bending devices may be needed to bend light entering the distal end of the endoscope to any imaging electronics that are secured to the relatively flat base 1608 of the heat dissipating section 1604.

Figure 32:
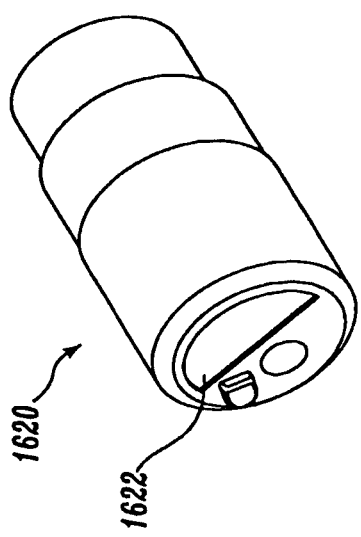

FIG. 32 shows a heat dissipating distal tip of an endoscope wherein the distal tip does not include a cover but is molded from a single piece of heat dissipating material such as a biocompatible metal. The heat dissipating section 1620 again includes a semicircular opening with a relatively flat surface 1622 that extends along the diameter of the section and on which heat generating electronic devices can be mounted. With a semicircular opening formed in the distal end of the heat dissipating distal tip 1620, the illumination mechanism and image sensor are mounted on the flat surface 1622. The irrigation port is oriented to direct water over the hemispherical cutout in order to clean the illumination mechanism and image sensor or image sensor lenses.

In yet another embodiment of the invention, the imaging devices at the distal end of the endoscope can be cooled by air or water passed through a lumen to the end of the endoscope and vented outside the body. For example, air under pressure may be vented through an orifice near the imaging electronics. The expansion of the air lowers its temperature where it cools the imaging electronics. The warmed air is then forced to the proximal end of the endoscope through an exhaust lumen. Alternatively, the endoscope may include a water delivery lumen that delivers water to a heat exchanger at the distal tip. Water warmed by the electronic components in the distal tip is removed in a water return lumen. Air or water can be alternatively be released directly to the patient lumen if the volumes and temperatures are physiologically acceptable.

Figure 33:
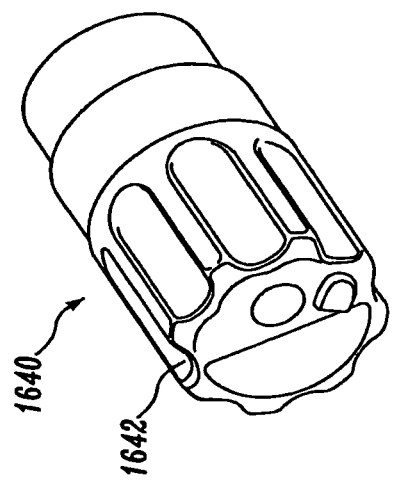
FIGS. 32 and 33 illustrate alternative embodiments of a passive heat dissipating distal tip in accordance with the present invention.

FIG. 33 shows an alternative embodiment of the passive heat dissipating distal tip shown in FIG. 31. In this example, the heat dissipating distal tip 1640 has a number of scalloped channels 1642 positioned around the circumference of the distal tip. The scalloped channels 1642 increase the surface area of the heat dissipating distal tip, thereby further increasing the ability of the tip to dissipate heat from the illumination and imaging electronic devices.

Although the present endoscope system has many uses, it is particularly suited for performing colonoscopic examinations. In one embodiment, a 10-13 mm diameter prototype having a 0.060 inner spiral wrap with a pitch of ¼ inch and coated with a hydrophilic coating was found to have a coefficient of friction of 0.15 compared to 0.85 for conventional endoscopes. In addition, the endoscope of the present invention required 0.5 lbs. of force to push it through a 2-inch U-shaped bend where a conventional endoscope could not pass through such a tight bend. Therefore, the present invention allows colonoscopes to be made inexpensively and lightweight so that they are more comfortable for the patient due to their lower coefficient of friction and better trackability.

In addition to performing colonoscopies, the endoscope system of the present invention is also useful with a variety of surgical devices including: cannulas, guide wires, sphincterotomes, stone retrieval balloons, retrieval baskets, dilatation balloons, stents, cytology brushes, ligation devices, electro hemostasis devices, sclerotherapy needles, snares and biopsy forceps.

Cannulas are used with the endoscope system to cannulate the sphincter of Oddi or papilla to gain access to the bile or pancreatic ducts. Guide wires can be delivered down the working channel of the endoscope and used as a rail to deliver a surgical device to an area of interest. Sphincterotomes are used to open the papilla in order to place a stent or remove a stone from a patient. Stone retrieval balloons are used along with a guide wire to pull a stone out of a bile duct. Retrieval baskets are also used to remove stones from a bile duct or other tract. Dilatation balloons are used to open up strictures in the gastrointestinal, urinary or pulmonary tracts. Stents are used to open up strictures in the GI, urinary or pulmonary tracts. Stents can be metal or plastic, self-expanding or mechanically expanded, and are normally delivered from the distal end of a catheter. Cytology brushes are used at the end of guide wires to collect cell samples. Ligation devices are used to ligate varices in the esophagus. Band ligators employ elastic bands to cinch varices. Electrohemostasis devices use electrical current to cauterize bleeding tissue in the GI tract. Sclerotherapy needles are used to inject coagulating or sealing solutions into varices. Snares are used to remove polyps from the GI tract, and biopsy forceps are used to collect tissue samples.

Examples of specific surgical procedures that can be treated with the endoscopic system of the present invention include the treatment of gastroesophageal reflux disease (GERD) by the implantation of bulking agents, implants, fundoplication, tissue scarring, suturing, or replacement of valves or other techniques to aid in closure of the lower esophageal sphincter (LES).

Another example of a surgical procedure is the treatment of morbid obesity by deploying implants or performing reduction surgery, gastric bypass and plication or creating tissue folds to help patients lose weight.

Endoscopic mucosal resection (EMR) involves the removal of sessile polyps or flat lesions by filling them with saline or the like to lift them prior to resection. The endoscope of the present invention can be used to deliver needles, snares and biopsy forceps useful in performing this procedure.

In addition, the video endoscope system of the present invention can be used to perform full-thickness resection (FTRD) in which a portion of a GI tract wall is excised and the wounds healed with staplers or fasteners. Finally, the endoscope system of the present invention can be used to deliver sclerosing agents to kill tissues or drug delivery agents to treat maladies of internal body tissues.

While the preferred embodiment of the invention has been illustrated and described, it will be appreciated that various changes can be made therein without departing from the scope of the invention. For example, although some of the disclosed embodiments use the pull wires to compress the length of the endoscope, it will be appreciated that other mechanisms such as dedicated wires could be used. Alternatively, a spring can be used to bias the endoscope distally and wires used to compress the spring thereby shortening the length of the endoscope. Furthermore, although the disclosed embodiments use rotary servo motors to drive the control cables, other actuators such as linear actuators could be used. Similarly, although the endoscope discussed in connection with the preferred embodiment includes a working channel, it will be appreciated that such a channel may be omitted and the resulting catheter used to deliver a special purpose tool such as a snare, RF ablation tip, etc., to a desired location. Alternatively, the catheter could be used solely for imaging. Finally, although the disclosed components are described as being used in a video endoscope, it will be appreciated that many components may have separate utility by themselves or in other medical devices. Therefore, the scope of the invention is to be determined from the following claims and equivalents thereof.

The embodiments of the invention which an exclusive property or privilege is claimed are defined as follows:

1. An endoscope having a distal end, comprising:
   an illumination source positioned at the distal end of the endoscope;
   an irrigation lumen at the distal end for irrigating a lumen of a patient;
   an imaging lens for capturing images within the patient;
   a working channel terminating at the distal end;
   a first fluid supply lumen disposed along the endoscope;
   a second fluid supply lumen disposed along the endoscope; and
   a third fluid supply lumen disposed along the endoscope, wherein the first fluid supply lumen is configured to deliver fluid to the illumination source from a source of fluid completely external the first fluid supply lumen, the second fluid supply lumen is configured to deliver fluid to the irrigation lumen, and the third fluid supply lumen is configured to deliver fluid to the imaging lens, wherein the first fluid supply lumen delivers fluid to a heat exchanger coupled to the illumination source at the distal end.

2. The endoscope of claim 1, further comprising a fourth fluid supply lumen in fluid communication with the working channel and configured to deliver fluid through the working channel.

3. The endoscope of claim 1, wherein the second fluid supply lumen is configured to deliver fluid through the irrigation lumen.

4. The endoscope of claim 1, wherein the third fluid supply lumen is configured to deliver fluid across the imaging lens.

5. The endoscope of claim 4, wherein the third fluid supply lumen includes a flush port configured to direct fluid across a distal face of the imaging lens.

6. The endoscope of claim 2, wherein the fourth fluid supply lumen is in communication with a vacuum source to provide suction through the working channel.

7. The endoscope of claim 1, wherein each of the first, second, and third fluid supply lumens is controlled by a valve to selectively control the delivery of fluid to the illumination source, the irrigation lumen, and the imaging lens.

8. An endoscope having a distal face, comprising:
an illumination source internal the endoscope and positioned at an illumination source port disposed on the distal face;
an imaging lens for capturing images within the patient and terminating at an imaging lens port disposed on the distal face;
an imaging lens wash port disposed on the distal face and adjacent the imaging lens port;
a working channel terminating at the distal face; and
a plurality of fluid supply lumens disposed along the endoscope, each in separate fluid communication with one of the illumination source, the imaging lens wash port, and the working channel, wherein the fluid supply lumen in communication with the illumination source is configured to deliver fluid only internal the endoscope to a heat exchanger adjacent to the illumination source at the distal end face.

9. The endoscope of claim 8, wherein the imaging lens wash port directs fluid from one of the plurality of fluid supply lumens and across the imaging lens, the imaging lens wash port including a flush cap configured to deflect fluid exiting the imaging lens wash port to a front face of the image lens port.

10. The endoscope of claim 9, wherein the fluid supply lumen in fluid communication with the working channel is configured to deliver fluid through the working channel.

11. The endoscope of claim 1, wherein the first fluid supply lumen is configured to deliver fluid to only the illumination source, the second fluid supply lumen is configured to deliver fluid to only the irrigation lumen, and the third fluid supply lumen is configured to deliver fluid to only the imaging lens.

12. The endoscope of claim 1, wherein the first fluid supply lumen is configured to deliver fluid to the illumination source internal the endoscope.

13. An endoscope having a distal end, comprising:
an illumination source positioned at the distal end of the endoscope;
an irrigation lumen at the distal end for irrigating a lumen of a patient;
an imaging lens for capturing images within the patient;
a working channel terminating at the distal end;
a plurality of fluid supply lumens disposed along the endoscope, each configured to deliver fluid to one of the illumination source, the irrigation lumen, and the imaging lens, wherein a first supply lumen of the plurality of supply lumens is configured to deliver fluid from a fluid source to the illumination source and only internal the endoscope, wherein the first supply lumen delivers fluid to a heat exchanger coupled to the illumination source at the distal end; and
a fluid return lumen disposed along the endoscope and configured to return fluid delivered by the first supply lumen from only internal the endoscope to the fluid source.

14. The endoscope of claim 13, wherein the fluid return lumen is configured to return fluid from the heat exchanger to the fluid source.

15. The endoscope of claim 13, wherein the heat exchanger is disposed internal the endoscope.

16. The endoscope of claim 13, wherein the fluid return lumen is configured to return fluid from adjacent the illumination source.

17. The endoscope of claim 13, wherein fluid is continuously delivered to the illumination source and returned to the fluid source.

* * * * *